(12) United States Patent
Abramovitch et al.

(10) Patent No.: US 11,617,740 B2
(45) Date of Patent: Apr. 4, 2023

(54) **CHEMICAL INHIBITORS OF *MYCOBACTERIUM TUBERCULOSIS* DOSRST SIGNALING AND PERSISTENCE**

(71) Applicant: Board of Trustees of Michigan State University, East Lansing, MI (US)

(72) Inventors: Robert Abramovitch, East Lansing, MI (US); Edmund Ellsworth, Vicksburg, MI (US)

(73) Assignee: Board of Trustees of Michigan State University, East Lansing, MI (US)

( * ) Notice: Subject to any disclaimer, the term of this patent is extended or adjusted under 35 U.S.C. 154(b) by 0 days.

(21) Appl. No.: 16/955,385

(22) PCT Filed: Dec. 21, 2018

(86) PCT No.: PCT/US2018/067025
§ 371 (c)(1),
(2) Date: Jun. 18, 2020

(87) PCT Pub. No.: WO2019/126613
PCT Pub. Date: Jun. 27, 2019

(65) Prior Publication Data
US 2021/0000799 A1    Jan. 7, 2021

Related U.S. Application Data

(60) Provisional application No. 62/609,874, filed on Dec. 22, 2017.

(51) Int. Cl.
| | |
|---|---|
| *A61K 31/422* | (2006.01) |
| *A61P 31/04* | (2006.01) |
| *A61K 31/357* | (2006.01) |
| *A61K 31/42* | (2006.01) |
| *C07D 261/14* | (2006.01) |
| *C07D 413/12* | (2006.01) |

(52) U.S. Cl.
CPC .......... *A61K 31/422* (2013.01); *A61K 31/357* (2013.01); *A61K 31/42* (2013.01); *A61P 31/04* (2018.01); *C07D 261/14* (2013.01); *C07D 413/12* (2013.01)

(58) Field of Classification Search
CPC ........ C07D 261/14; A61K 31/42; A61P 31/04
See application file for complete search history.

(56) References Cited

U.S. PATENT DOCUMENTS

| 7,750,160 B2 | 7/2010 | Milanov et al. |
| 8,361,482 B2 | 1/2013 | Shafferman et al. |
| 2017/0362284 A1 | 12/2017 | Anantha et al. |

FOREIGN PATENT DOCUMENTS

| WO | WO-2019/126613 A1 | 6/2019 |

OTHER PUBLICATIONS

Patani et al. (Chemical Reviews, 1996, vol. 96, 3147-3176).*
International Search Report and Written Opinion for International Application No. PCT/US2018/067025 dated Apr. 1, 2019.
Zheng et al., "Inhibitors of *Mycobacterium tuberculosis* DosRST signaling and persistence," Nature Chemical Biology, 13: 218-225 (2017).

* cited by examiner

*Primary Examiner* — Kamal A Saeed
(74) *Attorney, Agent, or Firm* — Foley Hoag LLP

(57) ABSTRACT

Provides herein are novel compounds, compositions, and methods useful for inhibiting bacteria, such as *Mycobacterium tuberculosis*. These compositions and methods find many uses in medicine and research, e.g., treating subjects afflicted with active or latent bacterial infections.

11 Claims, 27 Drawing Sheets
Specification includes a Sequence Listing.

ated on Feb. 7, 2019, is named MSS-02225 (31742

SEQUENCE LISTING

```
<160> NUMBER OF SEQ ID NOS: 5

<210> SEQ ID NO 1
<211> LENGTH: 36
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1
tttcatatgg tggtaaaggt cttcttggtc gatgac                                 36

<210> SEQ ID NO 2
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 2
tttggatcct catggtccat caccgggtgg                                        30

<210> SEQ ID NO 3
<211> LENGTH: 6
<212> TYPE: PRT
<213> ORGANISM: Artificial Sequence
<220> FEATURE:
<223> OTHER INFORMATION: Description of Artificial Sequence: Synthetic
      6xHis tag

<400> SEQUENCE: 3

His His His His His His
1               5

<210> SEQ ID NO 4
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 4
```

```
caactgcacc gcgctcttga tg                                              22

<210> SEQ ID NO 5
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 5
catctcgtct tccagccgca tcaac                                           25
```

CHEMICAL INHIBITORS OF *MYCOBACTERIUM TUBERCULOSIS* DOSRST SIGNALING AND PERSISTENCE

CROSS-REFERENCE TO RELATED APPLICATIONS

This application is a national-stage application based on PCT/US18/67025, filed Dec. 21, 2018, which claims the benefit of U.S. Provisional Application No. 62/609,874, filed on Dec. 22, 2017; each of which is hereby incorporated by reference in its entirety.

SEQUENCE LISTING

The instant application contains a Sequence Listing which has been submitted electronically in ASCII format and is hereby incorporated by reference in its entirety. Said ASCII copy, created on Feb. 7, 2019, is named MSS-02225 (31742 02225) SL.txt and is 2000 bytes in size.

BACKGROUND

*Mycobacterium tuberculosis* (Mtb) is the causative agent of tuberculosis (TB). Mtb is an intracellular pathogen that can latently infect the host without any disease symptoms. During chronic infection, it can establish a dormant state known as non-replicating persistence (NRP) where Mtb modulates its metabolism in response to environmental and host immune system cues, such as hypoxia, acidic pH, and nutrient starvation. DosRST is a two-component regulatory system involved in Mtb persistence. It consists of two histidine kinase sensors, DosS and DosT, and the cognate response regulator DosR, which regulates expression of about 50 genes in the DosRST regulon. The pathway can be induced by host intracellular stimuli, such as nitric oxide (NO), carbon monoxide (CO) and hypoxia, through DosS and DosT. DosS is oxygen and redox sensor, whereas DosT acts an oxygen sensor. Both kinases sense ligands via the heme group, and are inactive when the heme exists as either the Met ($Fe^{3+}$) form (DosS) or the oxy ($Fe^{2+}$—$O_2$) form (DosT) in the presence of $O_2$. However, hypoxic conditions activate the kinases by inducing the conversion of DosS to the ferrous form and DosT to the deoxy form. Therefore, DosS/T play overlapping and distinct roles in sensing the redox status and oxygen level of the environment to turn on the DosR pathway.

Non-replicating bacilli are naturally tolerant to many anti-mycobacterial drugs, such as isoniazid (INH) that only kills replicating bacilli. During TB infection, the disease presents as a spectrum of replicating and non-replicating bacteria; the NRP population of bacteria are thought to be responsible, in part, for the 6-month long course of TB treatment. This long antibiotic regimen makes controlling the TB epidemic challenging and has likely contributed to the evolution of drug-resistant Mtb strains. Therefore, it is an urgent to identify new strategies and targets to treat the disease, with a particular focus on discovering new ways to shorten the course of TB therapy. Targeting the DosRST pathway is a promising strategy, because dosRST mutants have been shown highly attenuated in in vitro Wayne model of hypoxia-driven NRP and in several animal models that generate hypoxic granulomas, including non-human primates, guinea pigs, C3Heb/FeJ mouse models of TB infection (cite more). Furthermore, deletion of DosR-regulated gene tgs1 involved in triacylglycerol (TAG) synthesis causes reduced antibiotic tolerances. Therefore, inhibiting DosRST pathway and limiting the reservoir of NRP bacteria may function to narrow the spectrum of TB disease and shorten the course of TB therapy.

SUMMARY

In an effort to discover new chemical probes that inhibit Mtb persistence, whole cell phenotypic high throughput screening (HTS) of a >540,000 compound library using the DosRST regulon reporter strain CDC1551 (hspX'::GFP) was performed. Six compounds were discovered that inhibited the DosR-dependent, hypoxia-induced GFP fluorescence. Previously, it was shown that the HC101, HC102 and HC103 series, functioned to inhibit NRP associated physiologies, including TAG accumulation, survival during hypoxia and isoniazid tolerance. Mechanism of action studies showed that the HC101 series, composed on artemisinin and related analogs, functioned by oxidizing an alkylating DosS and DosT heme. HC102 and HC103 did not modulate DosS/T heme, and were instead found to inhibit sensor kinase autophosphorylation. Here we describe the characterization of two additional compounds, HC104A and HC106A. Transcriptional and biochemical analysis demonstrate that both compounds function to downregulate the DosRST pathway and inhibit persistence associated physiologies. Biochemical studies support that HC104A and HC106A function by new mechanisms of action, with HC104A inhibiting DosR DNA binding and HC106A interacting with DosS and DosT heme to block environmental sensing. Studies examining the pair-wise interactions between five DosRST inhibitors, revealed synergistic interactions, including strong potentiating interactions of artemisinin and HC106A. Structure activity relationship studies of HC106 identified functional groups of HC106A that are required for activity and enabled optimization of HC106 potency to nanomolar effective concentrations against whole cell Mtb.

*Mycobacterium tuberculosis* (Mtb) possesses a two-component regulatory system, DosRST, that enables Mtb to sense host immune cues and establish a state of non-replicating persistence (NRP). NRP bacteria are tolerant to several anti-mycobacterial drugs and are thought to play a role in the long course of tuberculosis (TB) therapy. Therefore, small molecules that inhibit Mtb from establishing or maintaining NRP could reduce the reservoir of drug tolerant bacteria and function as an adjunct therapy to reduce treatment time. Previously, a discovery of six novel chemical inhibitors of DosRST, including HC101A-106A, from a whole cell, reporter-based phenotypic high-throughput screen was reported. RNAseq transcriptional profiling shows that the compounds downregulate the dosR regulon. Furthermore, the inhibitors reduced hypoxia-induced triacylglycerol synthesis by ~50%. HC106A inhibits Mtb survival during NRP, however, surprisingly, HC104A did not inhibit survival in vitro. An electrophoretic mobility assay shows that HC104A inhibits DosR DNA binding in a dose-dependent manner, supporting that HC104A may function by directly targeting DosR. In contrast, UV-visible spectroscopy studies support that HC106A directly targets the histidine kinase heme, via a mechanism that is distinct from the oxidation and alkylation of heme previously observed with artemisinin (HC101A). Synergistic interactions were observed when several DosRST inhibitors were used in combinations with artemisinin, with the strongest potentiation observed between artemisinin and HC102A, HC103A, or HC106A. This data collectively shows that the DosRST pathway can be inhibited using multiple distinct mechanisms.

In some aspects, the invention relates to compounds having the structure of Formula (I), or a pharmaceutically acceptable salt thereof:

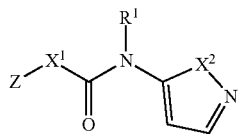

I wherein $X^1$, $X^2$, $R^1$, and Z are defined herein.

In another aspect, the invention relates to pharmaceutical compositions of a compound disclosed herein (e.g., a compound of Formula I) and a pharmaceutically acceptable carrier.

In some aspects, provided herein are methods for inhibiting growth of one or more bacterial cells by contacting the one or more bacterial cells with an effective amount of a compound disclosed herein (e.g., a compound of Formula I) to thereby inhibit the growth of the one or more bacterial cells. Also provided herein are methods of preventing or reducing the likelihood of a productive bacterial infection in a subject by administering to a subject an effective amount of a compound disclosed herein (e.g., a compound of Formula I), to thereby prevent or reduce the likelihood of a productive bacterial infection in the subject, wherein the subject has been identified as being at risk of developing an infection with bacterial cells.

In some aspects, provided herein are methods for treating a subject who is infected with bacterial cells by administering to the subject an effective amount of a compound disclosed herein (e.g., a compound of Formula I) to thereby treat the infection. In some aspects, also provided herein are methods for ameliorating the signs or symptoms of an infection of a subject by bacterial cells by administering to the subject an effective amount of a compound that inhibits the at least two-component regulatory system to thereby ameliorate the signs and symptoms of the infection. In some embodiments, the infection may be tuberculosis or non-tuberculosis *Mycobacterium*.

Unless otherwise defined, all technical and scientific terms used herein have the same meaning as commonly understood by one of ordinary skill in the art to which this disclosure pertains. In case of conflict, the present document, including definitions, will control. Preferred methods and materials are described below, although methods and materials similar or equivalent to those described herein can also be used in the practice or testing of the presently disclosed methods and compositions. All publications, patent applications, patents, and other references mentioned herein are incorporated by reference in their entirety.

Other features and advantages of the present disclosure, e.g., methods for treating bacterial infections, will be apparent from the following description, the examples, the drawings, and from the claims.

Figure 1:
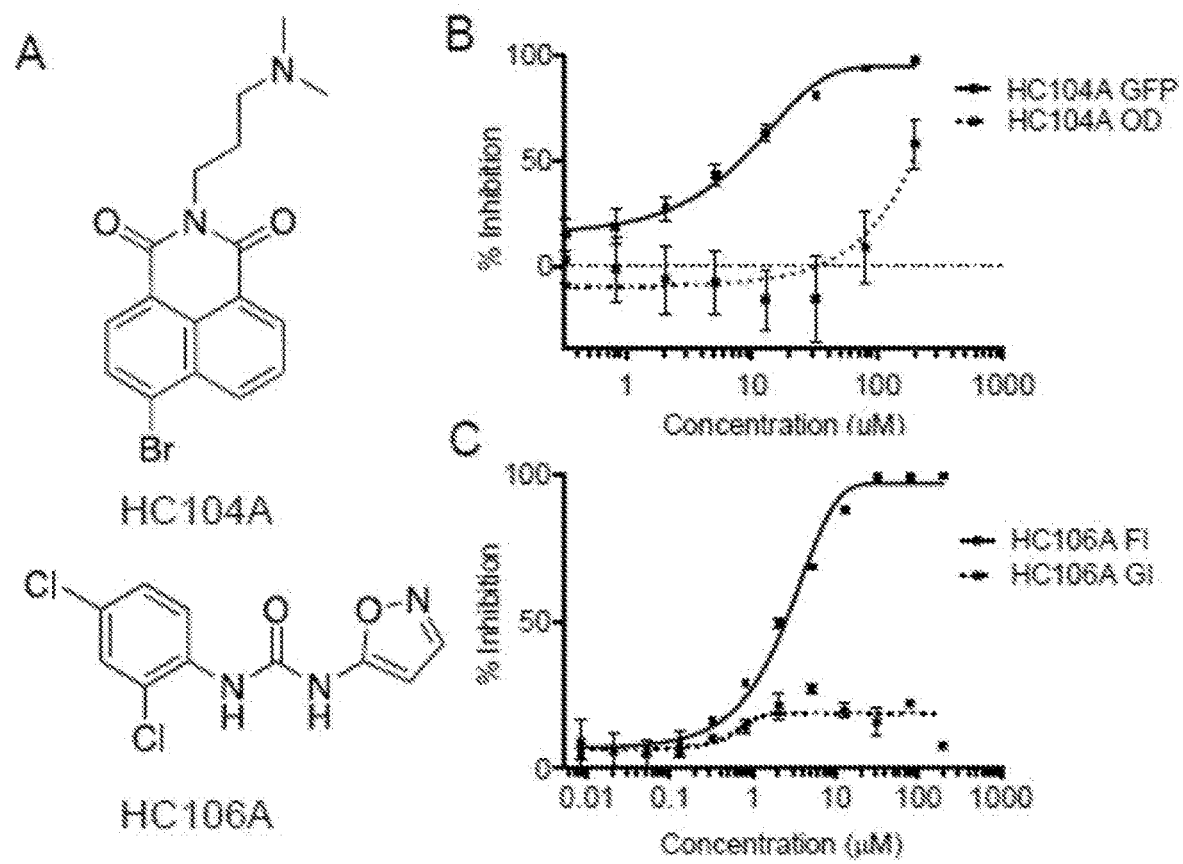
FIG. 1 has three parts, A-C, and shows HC104A and HC106A inhibit DosRST reporter fluorescence. (A) Chemical structures of HC104A and HC106A. HC104A (B) and HC106A (C) inhibited DosR-driven GFP fluorescence signal in a dose-dependent manner, while having minimal impact of Mtb growth. The $EC_{50}$ values of fluorescence inhibition (FI) for HC104A and HC106A are 9.8 µM and 2.48 µM, respectively.

Note that for every figure containing a histogram, the bars from left to right for each discreet measurement correspond to the figure boxes from top to bottom in the figure legend as indicated.

DETAILED DESCRIPTION

In certain aspects, the invention provides 1,2-oxazole substituted urea derivatives, and pharmaceutical compositions thereof. Also, provided herein are methods of treating a bacterial infection or inhibiting the growth of bacteria in a subject in need thereof.

I. Compounds

In certain embodiments, the invention relates to compounds having the structure of Formula (I), or a pharmaceutically acceptable salt thereof:

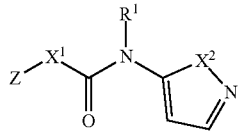

I wherein
$X^1$ is selected from $NR^2$, O, and $CR^4R^5$;
$X^2$ is selected from O and $NR^3$;
$R^1$, $R^2$, $R^3$, $R^4$, and $R^5$ are each independently selected from H and alkyl; and
Z is selected from optionally substituted alkyl, heteroalkyl, cycloalkyl, aryl, heteroaryl, aralkyl, heteroaralkyl, and carbamate or $R^2$ and Z together with the N to which they are bound combine to form an optionally substituted 4-, 5-, or 6-membered heterocyclic ring.

In some embodiments, $X^1$ is selected from $NR^2$ and O, preferably $X^1$ is $NR^2$. In some embodiments, $X^2$ is O.

In some embodiments, $R^1$ is H or $C_1$-$C_6$ alkyl, preferably H. In some embodiments, $R^2$ is H or $C_1$-$C_6$ alkyl. In some embodiments, $R^3$ is H or $C_1$-$C_6$ alkyl, preferably H. In some embodiments, $R^4$ is H or $C_1$-$C_6$ alkyl. In some embodiments, $R^5$ is H or $C_1$-$C_6$ alkyl, preferably H.

In some embodiments, Z is optionally substituted with alkyl, cycloalkyl, alkoxy, aryl, heteroaryl, acyl, halo, sulfone, sulfonate, hydroxy, amide, and amino. In some embodiments, Z is substituted with halo, alkyl, alkoxy, or aryl. For example, in some embodiments, Z is substituted with bromo, chloro, or fluoro. In some embodiments, Z is substituted with hydroxyl and alkoxycarbonyl.

In some embodiments, Z is optionally substituted aryl or heteroaryl. For example, in some embodiments, is optionally substituted phenyl. In some embodiments, is optionally substituted pyridyl. In some embodiments, Z is optionally substituted alkyl. For example, in some embodiments, Z is optionally substituted $C_1$-$C_6$ alkyl. In some embodiments, Z is optionally substituted cycloalkyl having 3 to 8 carbon atoms.

In some embodiments, Z is

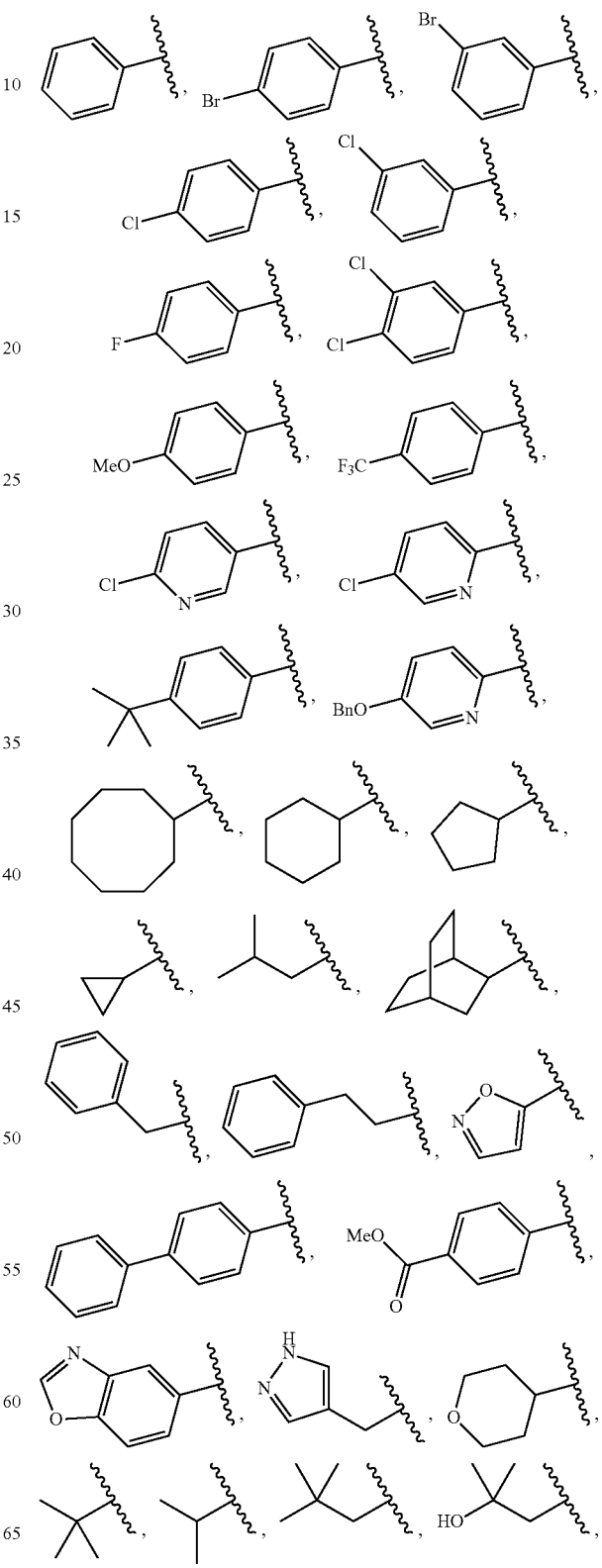

-continued

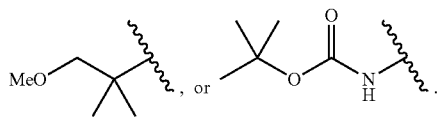

In some embodiments, R² and Z together with the N to which they are bound combine to form an optionally substituted 5-membered heterocyclic ring. In some embodiments, the 5-membered heterocyclic ring is substituted with an aryl moiety. For example, in some embodiments, R² and Z together with the N to which they are bound combine to form

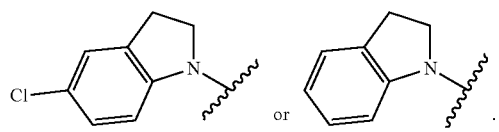 [SMILES: *N1CCc2cc(Cl)ccc21 ; *N1CCc2ccccc21]

In some embodiments, the compound is selected form a compound set forth in Table 1

TABLE 1

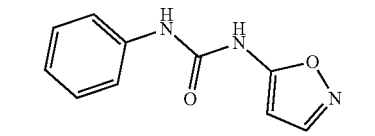 [SMILES: O=C(Nc1ccccc1)Nc1ccno1]

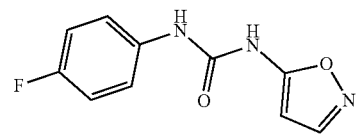 [SMILES: O=C(Nc1ccc(F)cc1)Nc1ccno1]

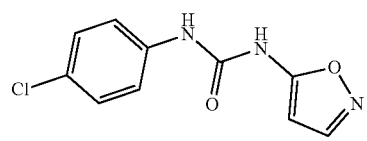 [SMILES: O=C(Nc1ccc(Cl)cc1)Nc1ccno1]

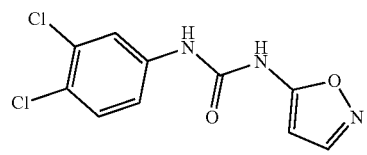 [SMILES: O=C(Nc1ccc(Cl)c(Cl)c1)Nc1ccno1]

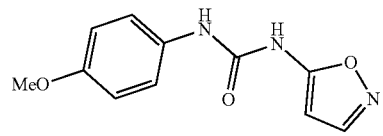 [SMILES: COc1ccc(NC(=O)Nc2ccno2)cc1]

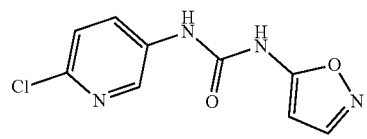 [SMILES: O=C(Nc1ccc(Cl)nc1)Nc1ccno1]

TABLE 1-continued

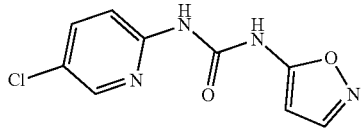 [SMILES: O=C(Nc1ccc(Cl)cn1)Nc1ccno1]

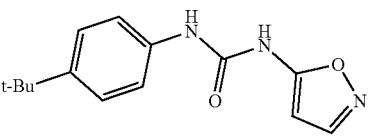 [SMILES: CC(C)(C)c1ccc(NC(=O)Nc2ccno2)cc1]

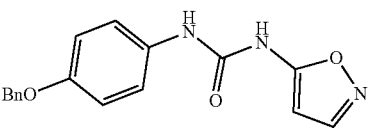 [SMILES: O=C(Nc1ccc(OCc2ccccc2)cc1)Nc1ccno1]

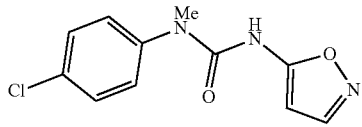 [SMILES: CN(C(=O)Nc1ccno1)c1ccc(Cl)cc1]

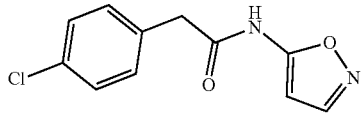 [SMILES: O=C(Cc1ccc(Cl)cc1)Nc1ccno1]

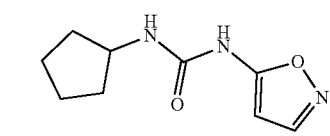 [SMILES: O=C(Nc1ccno1)NC1CCCC1]

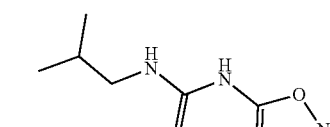

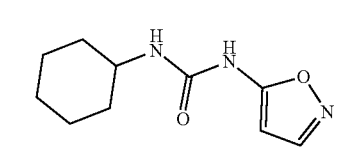 [SMILES: O=C(Nc1ccno1)NC1CCCCC1]

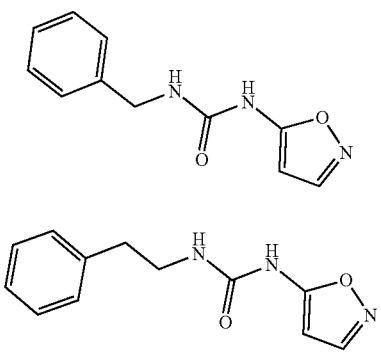

TABLE 1-continued

TABLE 1-continued

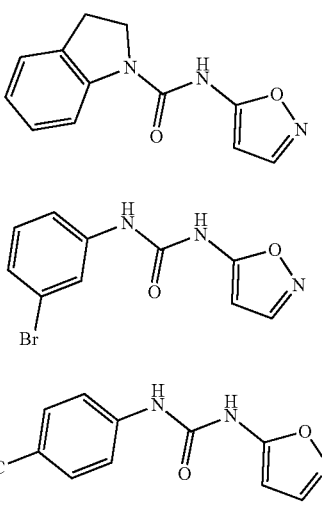

In some embodiments, the compound is selected form a compound set forth in Table 2.

TABLE 2

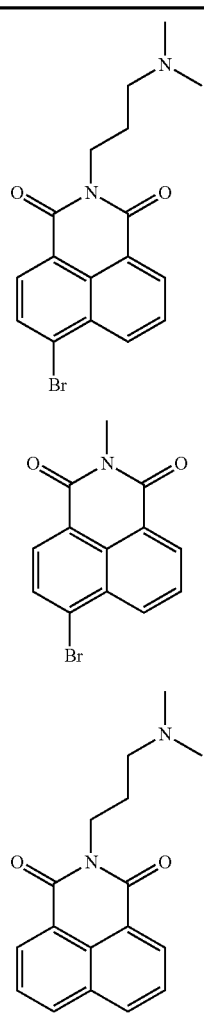

TABLE 2-continued

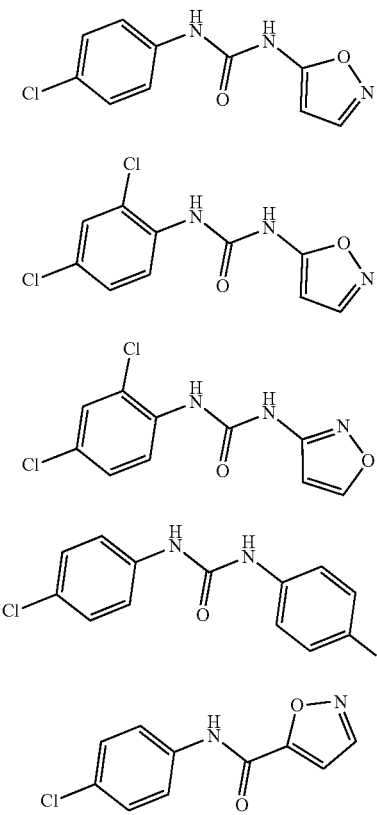

II. Pharmaceutical Compositions

In certain embodiments, the present invention provides pharmaceutical compositions comprising a compound disclosed herein (e.g., a compound of Formula I) and a pharmaceutically acceptable carrier.

The compounds disclosed herein may be delivered in a pharmaceutical composition. For example, the compositions or agents disclosed herein may be administered with a pharmaceutically acceptable carrier. Pharmaceutical compositions can be formulated for a variety of loads of administration, including systemic and topical or localized administration. Techniques and formulations generally may be found in *Remmington's Pharmaceutical Sciences*, Meade Publishing Co., Easton, Pa.

For administration by inhalation, the agents may be conveniently delivered in the form of an aerosol spray presentation from pressurized packs or a nebuliser, with the use of a suitable propellant, e.g., dichlorodifluoromethane, trichlorofluoromethane, dichlorotetrafluoroethane, carbon dioxide or other suitable gas. In the case of a pressurized aerosol the dosage unit may be determined by providing a valve to deliver a metered amount. Capsules and cartridges of e.g., gelatin, for use in an inhaler or insufflator may be formulated containing a powder mix of the agent and a suitable powder base such as lactose or starch.

For systemic administration, injection is preferred, including intramuscular, intravenous, intraperitoneal, and subcutaneous. For injection, the agents can be formulated in liquid solutions, preferably in physiologically compatible buffers such as Hank's solution or Ringer's solution. In addition, the agents may be formulated in solid form and redissolved or suspended immediately prior to use. Lyophilized forms are also included.

For oral administration, the pharmaceutical compositions may take the form of, for example, tablets, lozanges, or capsules prepared by conventional means with pharmaceutically acceptable excipients such as binding agents (e.g., pregelatinised maize starch, polyvinylpyrrolidone or hydroxypropyl methylcellulose); fillers (e.g., lactose, microcrystalline cellulose or calcium hydrogen phosphate); lubricants (e.g., magnesium stearate, talc or silica); disintegrants (e.g., potato starch or sodium starch glycolate); or wetting agents (e.g., sodium lauryl sulphate). The tablets may be coated by methods well known in the art. Liquid preparations for oral administration may take the form of, for example, solutions, syrups or suspensions, or they may be presented as a dry product for constitution with water or other suitable vehicle before use. Such liquid preparations may be prepared by conventional means with pharmaceutically acceptable additives such as suspending agents (e.g., sorbitol syrup, cellulose derivatives or hydrogenated edible fats); emulsifying agents (e.g., lecithin or acacia); non-aqueous vehicles (e.g., ationd oil, oily esters, ethyl alcohol or fractionated vegetable oils); and preservatives (e.g., methyl or propyl-p-hydroxybenzoates or sorbic acid). The preparations may also contain buffer salts, flavoring, coloring and sweetening agents as appropriate. Preparations for oral administration may be suitably formulated to give controlled release of the active compound. The pH of the formulations ranges from about 3 to about 11, but is ordinarily about 7 to 10.

Pharmaceutical agents that may oxidize and lose biological activity, especially in a liquid or semisolid form, may be prepared in a nitrogen atmosphere or sealed in a type of capsule and/or foil package that excludes oxygen.

The pharmaceutical agents may be formulated for parenteral administration by injection, e.g., by bolus injection or continuous infusion. Formulations for injection may be presented in unit dosage form, e.g., in ampoules or in multi-dose containers, with an added preservative. The agents may take such forms as suspensions, solutions or emulsions in oily or aqueous vehicles, and may contain formulatory agents such as suspending, stabilizing and/or dispersing agents. Alternatively, the active ingredient may be in powder form for constitution with a suitable vehicle, e.g., sterile pyrogen-free water, before use.

Pharmaceutical compositions may comprise from about 0.00001 to 100% such as from 0.001 to 10% or from 0.1% to 5% by weight of one or more agents described herein.

In one embodiment, a pharmaceutical agent described herein, is incorporated into a topical formulation containing a topical earner that is generally suited to topical drug administration and comprising any such material known in the art. The topical carrier may be selected so as to provide the composition in the desired form, e.g., as an ointment, lotion, cream, microemulsion, gel, oil, solution, or the like, and may be comprised of a material of either naturally occurring or synthetic origin. It is preferable that the selected carrier not adversely affect the active agent or other components of the topical formulation. Examples of suitable topical carriers for use herein include water, alcohols and other nontoxic organic solvents, glycerin, mineral oil, silicone, petroleum jelly, lanolin, fatty acids, vegetable oils, parabens, waxes, and the like.

Pharmaceutical agents may be incorporated into ointments, which generally are semisolid preparations which are typically based on petrolatum or other petroleum derivatives. The specific ointment base to be used, as will be appreciated by those skilled in the art, is one that will provide for optimum drug delivery, and, preferably, will provide for other desired characteristics as well, e.g., emolliency or the like. As with other carriers or vehicles, an ointment base should be inert, stable, nonirritating and nonsensitizing. As explained in Remington's, ointment bases may be grouped in four classes: oleaginous bases; emulsifiable bases; emulsion bases; and water-soluble bases. Oleaginous ointment bases include, for example, vegetable oils, fats obtained from animals, and semisolid hydrocarbons obtained from petroleum. Emulsifiable ointment bases, also known as absorbent ointment bases, contain little or no water and include, for example, hydroxystearin sulfate, anhydrous lanolin and hydrophilic petrolatum. Emulsion ointment bases are either water-in-oil (W/O) emulsions or oil-in-water (O/W) emulsions, and include, for example, cetyl alcohol, glyceryl monostearate, lanolin and stearic acid. Exemplary water-soluble ointment bases are prepared from polyethylene glycols (PEGs) of varying molecular weight; again, reference may be had to Remington's, supra, for further information.

Pharmaceutical agents may be incorporated into lotions, which generally are preparations to be applied to the skin surface without friction, and are typically liquid or semiliquid preparations in which solid particles, including the active agent, are present in a water or alcohol base. Lotions are usually suspensions of solids, and may comprise a liquid oily emulsion of the oil-in-water type. Lotions are preferred formulations for treating large body areas, because of the ease of applying a more fluid composition. It is generally necessary that the insoluble matter in a lotion be finely divided. Lotions will typically contain suspending agents to produce better dispersions as well as compounds useful for localizing and holding the active agent in contact with the skin, e.g., methylcellulose, sodium carboxymethylcellulose, or the like. An exemplary lotion formulation for use in conjunction with the present method contains propylene glycol mixed with a hydrophilic petrolatum.

Pharmaceutical agents may be incorporated into creams, which generally are viscous liquid or semisolid emulsions, either oil-in-water or water-in-oil. Cream bases are water-washable, and contain an oil phase, an emulsifier and an aqueous phase. The oil phase is generally comprised of petrolatum and a fatty alcohol such as cetyl or stearyl alcohol; the aqueous phase usually, although not necessarily, exceeds the oil phase in volume, and generally contains a humectant. The emulsifier in a cream formulation, as explained in Remington's, supra, is generally a nonionic, anionic, cationic or amphoteric surfactant.

Pharmaceutical agents may be incorporated into microcmulsions, which generally are thermodynamically stable, isotropically clear dispersions of two immiscible liquids, such as oil and water, stabilized by an interfacial film of surfactant molecules (*Encyclopedia of Pharmaceutical Technology* (New York: Marcel Dekker, 1992), volume 9). For the preparation of microemulsions, surfactant (emulsifier), co-surfactant (co-emulsifier), an oil phase and a water phase are necessary. Suitable surfactants include any surfactants that are useful in the preparation of emulsions, e.g., emulsifiers that are typically used in the preparation of creams. The co-surfactant (or "co-emulsifier") is generally selected from the group of poly glycerol derivatives, glycerol derivatives and fatty alcohols. Preferred emulsifier/co-emulsifier combinations are generally although not necessarily selected from the group consisting of: glyceryl monostearate and polyoxyethylene stearate; polyethylene glycol and ethylene glycol palmitostearate; and caprilic and capric triglycerides and oleoyl macrogolglycerides. The water phase includes not only water but also, typically, buffers, glucose, propylene glycol, polyethylene glycols, preferably lower molecular weight polyethylene glycols (e.g., PEG 300 and PEG 400), and/or glycerol, and the like, while the oil phase will generally comprise, for example, fatty acid esters, modified vegetable oils, silicone oils, mixtures of mono- di- and triglycerides, mono- and di-esters of PEG (e.g., oleoyl macrogol glycerides), etc.

Pharmaceutical agents may be incorporated into gel formulations, which generally are semisolid systems consisting of either suspensions made up of small inorganic particles (two-phase systems) or large organic molecules distributed substantially uniformly throughout a carrier liquid (single phase gels). Single phase gels can be made, for example, by combining the active agent, a carrier liquid and a suitable gelling agent such as tragacanth (at 2 to 5%), sodium alginate (at 2-10%), gelatin (at 2-15%), methylcellulose (at 3-5%), sodium carboxymethylcellulose (at 2-5%), carbomer (at 0.3-5%) or polyvinyl alcohol (at 10-20%) together and mixing until a characteristic semisolid product is produced. Other suitable gelling agents include methylhydroxycellulose, polyoxyethylene-polyoxypropylene, hydroxyethylcellulose and gelatin. Although gels commonly employ aqueous carrier liquid, alcohols and oils can be used as the carrier liquid as well.

Various additives, known to those skilled in the art, may be included in formulations, e.g., topical formulations. Examples of additives include, but are not limited to, solubilizers, skin permeation enhancers, opacifiers, preservatives (e.g., anti-oxidants), gelling agents, buffering agents, surfactants (particularly nonionic and amphoteric surfactants), emulsifiers, emollients, thickening agents, stabilizers, humectants, colorants, fragrance, and the like. Inclusion of solubilizers and/or skin permeation enhancers is particularly preferred, along with emulsifiers, emollients and preservatives. An optimum topical formulation comprises approximately: 2 wt. % to 60 wt. %, preferably 2 wt. % to 50 wt. %, solubilizer and/or skin permeation enhancer; 2 wt. % to 50 wt. %, preferably 2 wt. % to 20 wt. %, emulsifiers; 2 wt. % to 20 wt. % emollient; and 0.01 to 0.2 wt. % preservative, with the active agent and carrier (e.g., water) making of the remainder of the formulation. A skin permeation enhancer serves to facilitate passage of therapeutic levels of active agent to pass through a reasonably sized area of unbroken skin. Suitable enhancers are well known in the art and include, for example: lower alkanols such as methanol ethanol and 2-propanol; alkyl methyl sulfoxides such as dimethylsulfoxide (DMSO), decylmethylsulfoxide and tetradecylmethyl sulfoxide; pyrrolidones such as 2-pyrrolidone, N-methyl-2-pyrrolidone and N-(-hydroxyethyl)pyrrolidone; urea; N,N-diethyl-m-toluamide; $C_2$-$C_6$ alkanediols; miscellaneous solvents such as dimethyl formamide (DMF), N,N-dimethylacetamide (DMA) and tetrahydrofurfuryl alcohol; and the 1-substituted azacycloheptan-2-ones, particularly 1-n-dodecylcyclazacycloheptan-2-one (laurocapram; available under the trademark Azone® from Whitby Research Incorporated, Richmond, Va.).

Examples of solubilizers include, but are not limited to, the following: hydrophilic ethers such as diethylene glycol monoethyl ether (ethoxydiglycol) and diethylene glycol monoethyl ether oleate; polyethylene castor oil derivatives such as polyoxy 35 castor oil, polyoxy 40 hydrogenated castor oil, etc.; polyethylene glycol, particularly lower molecular weight polyethylene glycols such as PEG 300 and PEG 400, and polyethylene glycol derivatives such as PEG-8 caprylic/capric glycerides; alkyl methyl sulfoxides such as DMSO; pyrrolidones such as 2-pyrrolidone and N-methyl-2-pyrrolidone; and DMA. Many solubilizers can also act as absorption enhancers. A single solubilizer may be incorporated into the formulation, or a mixture of solubilizers may be incorporated therein.

Suitable emulsifiers and co-emulsifiers include, without limitation, those emulsifiers and co-emulsifiers described with respect to microemulsion formulations. Emollients include, for example, propylene glycol, glycerol, isopropyl myristate, polypropylene glycol-2 (PPG-2) myristyl ether propionate, and the like.

In an alternative embodiment, a pharmaceutical formulation is provided for oral or parenteral administration, in which case the formulation may comprise an activating compound-containing microemulsion as described above, and may contain alternative pharmaceutically acceptable carriers, vehicles, additives, etc. particularly suited to oral or parenteral drug administration. Alternatively, an activating compound-containing microemulsion may be administered orally or parenterally substantially as described above, without modification.

Effective dose of a pharmaceutical agent and or the compounds described herein depends at least on the nature of the condition being treated, toxicity, whether the compound is being used prophylactically (lower doses), the method of delivery, and the pharmaceutical formulation will be determined by the clinician using conventional dose escalation studies. It can be expected to be from about 0.0001 to about 100 mg/kg body weight per day; typically, from about 0.01 to about 10 mg/kg body weight per day; more typically, from about 0.01 to about 5 mg/kg body weight per day; most typically, from about 0.05 to about 0.5 mg/kg body weight per day. For example, the daily candidate dose for a human may range from about 0.001 mg to 1000 mg (e.g., at least 0.001 mg, at least 0.01 mg, at least 0.1 mg; at least 1 mg, at least 10 mg, at least 20 mg, at least 50 mg, at least 100 mg, at least 150 mg, at least 200 mg, at least 250 mg, at least 300 mg, at least 400 mg, at least 500 mg, at least 600 mg, at least 700 mg, at least 900 mg, at least 1000 mg, at least 1100 mg or at least 1200 mg per dose) and may take the form of single or multiple doses. A dose may be given, for example, continuously, daily, twice a day twice a week, three times a week, every other day, weekly, or twice a monthly. The length of treatment may depend on patient heath or severity of infection. Artemisinin may be administered at any therapeutically effective dose, including, but not limited to, at least 0.001 mg, at least 0.01 mg, at least 0.1 mg, at least 1 mg, at least 10 mg, at least 20 mg, at least 50 mg, at least 100 mg, at least 150 mg, at least 200 mg, at least 250 mg, at least 300 mg, at least 400 mg, at least 500 mg, at least 600 mg, at least 700 mg, at least 900 mg, at least 1000 mg, at least 1100 mg or at least 1200 mg per (lose.

III. Methods

In some aspects, provided herein are methods for inhibiting growth of one or more bacterial cells by contacting the one or more bacterial cells with an effective amount of a compound disclosed herein (e.g., a compound of Formula I) to thereby inhibit the growth of the one or more bacterial cells. Also provided herein are methods of preventing or reducing the likelihood of a productive bacterial infection in a subject by administering to a subject an effective amount of a compound disclosed herein (e.g., a compound of Formula I), to thereby prevent or reduce the likelihood of a productive bacterial infection in the subject, wherein the subject has been identified as being at risk of developing an infection with bacterial cells.

In some aspects, provided herein are methods for treating a subject who is infected with bacterial cells by administering to the subject an effective amount of a compound disclosed herein (e.g., a compound of Formula I) to thereby treat the infection. In some aspects, also provided herein are methods for ameliorating the signs or symptoms of an infection of a subject by bacterial cells, the method comprising administering to the subject an effective amount of a compound that inhibits the at least two-component regulatory system to thereby ameliorate the signs and symptoms of the infection. The infection may be tuberculosis or non-tuberculosis *Mycobacterium*.

In some embodiments, the DorRST two component regulatory system is conserved in the bacterial cells. In no way wishing to be bound by theory, the compounds disclosed herein may directly target the DorRST regulon. For example, the compounds may inhibit DosRST signaling, inhibit DosST sensor kinase activity, modulate DosST heme, or inhibit DosR DNA binding. In some embodiments, the compounds described herein are DosRST inhibitors. In some embodiments, the compounds described herein down-regulate genes in the DosR regulon. The compounds described herein may inhibit TAG biosynthesis. In some embodiments, the compounds described here reduce bacterial survival during NPR. In some embodiments, the compounds described herein interact and/or bind with heme of sensor kinase DosS. In some embodiments, the compounds described herein prevent or inhibit heme from sensing signals and disrupts signal transduction of a two-component regulatory system.

In some embodiments, the bacterial cells described herein may be any bacteria that utilizes heme in sensing environmental signals.

In some embodiments, the bacterial cells are *Mycobacterium*. The *Mycobacterium* may be *Mycobacterium tuberculosis*. The *Mycobacterium* may be any *Mycobacterium* species that causes tuberculosis or belongs to the *Mycobacterium tuberculosis* complex. Species in this complex include *M. africanum M. bovis, M. canetti, M. caprae. M. microti, M. mungi, M. orygis, M. pinnipedii, M. suricattae* and *M. tuberculosis*.

The *Mycobacterium* may be any other species of *Mycobacterium* (e.g., any species disclosed herein), such as nontuberculous mycobacteria. Nontuberculous mycobacteria are commonly present in soil and water and are usually much less virulent in humans than is *Mycobacterium tuberculosis*. Infections with these organisms have been called atypical, environmental, and nontuberculous mycobacterial infections.

Exposures and infections by these organisms often requires a defect in local or systemic host defenses; the frail elderly and immunocompromised people are at the highest risk. *M. avium* complex (MAC), including the closely related species of *M. avium* and *M. intracellulare*, accounts for many of nontuberculosis mycobacterial diseases. Other causative species include *M. kansasii, M. xenopi, M. marinum, M. ulcerans, M. fortuitum, M. abscessus*, and *M. chelonae*.

Other species of *Mycobacterium* include *M. asiaticum, M. gordonae, M. gastri, M. kansasii, M. hiberniae, M. icosiumassiliensis, M. nonchromogenicum, M. terrae, M. triviale, M. ulcerans, M. pseudoshottsii, M. shottsii, M. florentinum, M. geiavense, M. heidelbergense, M. interjectum, M. kubicae, M. lentiflavum, M. montefiorense, M. palustre, M. parascrofulaceum, M. simiae, M. triplex, M. arabiense, M. aromaticivorans, M. aquaticum, M. bacteremicum, M. bohemicum, M. botniense, M. branderi, M. celatum, M. chimaera, M. conspicuum, M. cookii, M. doricum, M. farcinogenes, M. haemophilum, M. heckeshornense, M. intracellulare, M. lacus, M. leprae, M. lepraemurium, M. lepromatosis, M. liflandii, M. llatzerense, M. malmoense, M. marinum*, causes a rare disease called Aquarium granuloma, *M. neoaurum, M. monacense, M. murale, M. nebraskense, M. saskatchewanense, M. sediminis, M. scrofulaceum, M. shimoidei, M. szulgai, Mycobacterium talmoniae, M. tusciae, M. xenopi, M. yongonense, M. intermedium, M. abscessus, M. bolletii, M. massiliense, M. chelonae, M. immunogenum, M. stephanolepidis, M. boenickei, M. brisbanense, M. cosmeticum, M. fortuitum, M. fortuitum* subsp. *acetamidolyticum, M. houstonense, M. mageritense, M. neworleansense, M. peregrinum, M. porcinum, M. senegalense, M. septicum, Mycobacterium aubagnese, M. mucogenicum, Mycobacterium phocaicum, M. austroafricanum, M. diernhoferi, M. frederiksbergense, M. hodleri, M. neoaurum, M. parafortuitum, M. aurum, M. vaccae, M. chitae, M. fallax, M. agri, M. aichiense, M. alvei, M. arupense, M. barrassiae, M. brumae, M. canariasense, M. chubuense, M. conceptionense, M. confluentis, M. duvalii, M. elephantis, M. flavescens, M. gadium, M. gilvum, M. hassiacum, M. holsaticum, M. iranicum, M. komossense, M. madagascariense. M. massilipolynesiensis, M. moriokaense, M. obuense, M. phlei, M. psychrotolerans, M. pulveris, M. pyrenivorans, M. smegmatis, M. goodii, M. wolinskyi, M. sphagni, M. thermoresistibile, M. vanbaalenii, M. arosiense, M. aubagnense, M. chlorophenolicum, M. fluoroantlhenivorans, M. kumamotonense, M. novocastrense, M. parmense, M. poriferae, M. rhodesiae, M. seoulense* or *M. tokaiense*.

In some embodiments, the *Mycobacterium* are tolerant to one or more anti-mycobacterial drugs. Anti-mycobacterial compounds include, but are not limited to, Clofazimine, Dapsone, Capreomycin, Cycloserine, Ethambutol, Ethionamide, Isoniazid, Pyrazinamide, Rifampicin, Rifabutin, Rifapentine, and Streptomycin. In some embodiments, the compounds described herein (e.g., a compound of Formula I) are administered in combination with at least one anti-mycobacterial drug (e.g., Clofazimine, Dapsone, Capreomycin. Cycloserine, Ethambutol, Ethionamide, Isoniazid, Pyrazinamide, Rifampicin, Rifabutin, Rifapentine, and/or Streptomycin).

The methods described herein further comprise administering at least two compounds (e.g., at least three compounds, at least four compounds, at least five compounds, at least six compounds) of Formula I to a subject. In some embodiments, the methods described herein further comprise administering artemisinin in combination with a compound of Formula I. In some embodiments, artemisinin in combination with a compound of Formula I has a potentiation effect.

IV. Definitions

For convenience, certain terms employed in the specification, examples, and appended claims are collected here.

The articles "a" and "an" are used herein to refer to one or to more than one (i.e., to at least one) of the grammatical object of the article.

As used herein, the term "administering" means providing an agent or composition to a subject, and includes, but is not limited to, administering by a medical professional and self-administering.

As used herein, an "effective amount" is an amount effective in treating or preventing a disease associated with a pathological immune response, including, for example, inflammatory bowel disease.

As used herein, the phrase "pharmaceutically-acceptable carrier" means a pharmaceutically-acceptable material, composition or vehicle, such as a liquid or solid filler, diluent, excipient, or solvent encapsulating material, involved in carrying or transporting an agent from one organ, or portion of the body, to another organ, or portion of the body. Each carrier must be "acceptable" in the sense of being compatible with the other ingredients of the formulation and not injurious to the patient. Some examples of materials which can serve as pharmaceutically-acceptable carriers include: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) pH buffered solutions; (21) polyesters, polycarbonates and/or polyanhydrides; and (22) other non-toxic compatible substances employed in pharmaceutical formulations.

As used herein, the term "subject" means a human or non-human animal selected for treatment or therapy. In certain embodiments, of the methods and compositions described herein the subject is a human subject.

The phrases "therapeutically-effective amount" and "effective amount" as used herein means the amount of an agent which is effective for producing the desired therapeutic effect in at least a sub-population of cells in a subject at a reasonable benefit/risk ratio applicable to any medical treatment.

"Treating" a disease in a subject or "treating" a subject having a disease refers to subjecting the subject to a pharmaceutical treatment, e.g., the administration of a drug, such that at least one symptom of the disease is decreased or prevented from worsening. As used herein, the terms "treat," "treating," and "treatment" include: (1) preventing a pathological condition, disorder, or disease, i.e. causing the clinical symptoms of the pathological condition, disorder, or disease not to develop in a subject that may be predisposed to the pathological condition, disorder, or disease but does not yet experience any symptoms of the pathological condition, disorder, or disease; (2) inhibiting the pathological condition, disorder, or disease, i.e. arresting or reducing the development of the pathological condition, disorder, or disease or its clinical symptoms; or (3) relieving the pathological condition, disorder. or disease, i.e. causing regression of the pathological condition, disorder, or disease or its clinical symptoms. These terms encompass also prophylaxis, therapy, and cure. Treatment means any manner in which the symptoms of a pathological condition, disorder, or disease are ameliorated or otherwise beneficially altered. Preferably, the subject in need of such treatment is a mammal, more preferable a human.

The term "acyl" is art-recognized and refers to a group represented by the general formula hydrocarbylC(O)—, preferably alkylC(O)—.

The term "acylamino" is art-recognized and refers to an amino group substituted with an acyl group and may be represented, for example, by the formula hydrocarbylC(O)NH—.

The term "acyloxy" is art-recognized and refers to a group represented by the general formula hydrocarbylC(O)O—, preferably alkylC(O)O—.

The term "alkoxy" refers to an alkyl group, preferably a lower alkyl group, having an oxygen attached thereto. Representative alkoxy groups include methoxy, —OCF$_3$, ethoxy, propoxy, tert-butoxy and the like.

The term "cycloalkyloxy" refers to a cycoakyl group having an oxygen attached thereto.

The term "alkoxyalkyl" refers to an alkyl group substituted with an alkoxy group and may be represented by the general formula alkyl-O-alkyl.

The term "alkylaminoalkyl" refers to an alkyl group substituted with an alkylamino group.

The term "alkenyl", as used herein, refers to an aliphatic group containing at least one double bond and is intended to include both "unsubstituted alkenyls" and "substituted alkenyls", the latter of which refers to alkenyl moieties having substituents replacing a hydrogen on one or more carbons of the alkenyl group. Such substituents may occur on one or more carbons that are included or not included in one or more double bonds. Moreover, such substituents include all those contemplated for alkyl groups, as discussed below, except where stability is prohibitive. For example, substitution of alkenyl groups by one or more alkyl, carbocyclyl, aryl, heterocyclyl, or heteroaryl groups is contemplated.

An "alkyl" group or "alkane" is a straight chained or branched non-aromatic hydrocarbon which is completely saturated. Typically, a straight chained or branched alkyl group has from 1 to about 20 carbon atoms, preferably from 1 to about 10 unless otherwise defined. Examples of straight chained and branched alkyl groups include methyl, ethyl, n-propyl, iso-propyl, n-butyl, sec-butyl, tert-butyl, pentyl, hexyl, pentyl and octyl. A $C_1$-$C_6$ straight chained or branched alkyl group is also referred to as a "lower alkyl" group.

Moreover, the term "alkyl" (or "lower alkyl") as used throughout the specification, examples, and claims is intended to include both "unsubstituted alkyls" and "substituted alkyls", the latter of which refers to alkyl moieties having substituents replacing a hydrogen on one or more carbons of the hydrocarbon backbone. Such substituents, if not otherwise specified, can include, for example, a halogen, a hydroxyl, a carbonyl (such as a carboxyl, an alkoxycarbonyl, a formyl, or an acyl), a thiocarbonyl (such as a thioester, a thioacetate, or a thioformate), an alkoxyl, a phosphoryl, a phosphate, a phosphonate, a phosphinate, an amino, an amido, an amidine, an imine, a cyano, a nitro, an azido, a sulfhydryl, an alkylthio, a sulfate, a sulfonate, a sulfamoyl, a sulfonamido, a sulfonyl, a heterocyclyl, an aralkyl, or an aromatic or heteroaromatic moiety. It will be understood by those skilled in the art that the moieties substituted on the hydrocarbon chain can themselves be substituted, if appropriate. For instance, the substituents of a substituted alkyl may include substituted and unsubstituted forms of amino, azido, imino, amido, phosphoryl (including phosphonate and phosphinate), sulfonyl (including sulfate, sulfonamido, sulfamoyl and sulfonate), and silyl groups, as well as ethers, alkylthios, carbonyls (including ketones, aldehydes, carboxylates, and esters), —CF$_3$, —CN and the like. Exemplary substituted alkyls are described below. Cycloalkyls can be further substituted with alkyls, alkenyls, alkoxys, alkylthios, aminoalkyls, carbonyl-substituted alkyls, —CF$_3$, —CN, and the like.

The term "C$_{x-y}$" when used in conjunction with a chemical moiety, such as, acyl, acyloxy, alkyl, alkenyl, alkynyl, or alkoxy is meant to include groups that contain from x to y carbons in the chain. For example, the term "C$_{x-y}$alkyl" refers to substituted or unsubstituted saturated hydrocarbon groups, including straight-chain alkyl and branched-chain alkyl groups that contain from x to y carbons in the chain, including haloalkyl groups such as trifluoromethyl and 2,2,2-trifluoroethyl, etc. Co alkyl indicates a hydrogen where the group is in a terminal position, a bond if internal. The terms "C$_{2-y}$alkenyl" and "C$_{2-y}$alkynyl" refer to substituted or unsubstituted unsaturated aliphatic groups analogous in length and possible substitution to the alkyls described above, but that contain at least one double or triple bond respectively.

The term "alkylamino", as used herein, refers to an amino group substituted with at least one alkyl group.

The term "alkylthio", as used herein, refers to a thiol group substituted with an alkyl group and may be represented by the general formula alkylS—.

The term "alkynyl", as used herein, refers to an aliphatic group containing at least one triple bond and is intended to include both "unsubstituted alkynyls" and "substituted alkynyls", the latter of which refers to alkynyl moieties having substituents replacing a hydrogen on one or more carbons of the alkynyl group. Such substituents may occur on one or more carbons that are included or not included in one or more triple bonds. Moreover, such substituents include all those contemplated for alkyl groups, as discussed above, except where stability is prohibitive. For example, substitution of alkynyl groups by one or more alkyl, carbocyclyl, aryl, heterocyclyl, or heteroaryl groups is contemplated.

The term "amide", as used herein, refers to a group

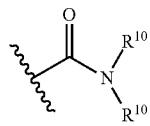

wherein each R$^{10}$ independently represent a hydrogen or hydrocarbyl group, or two R$^{10}$ are taken together with the N atom to which they are attached complete a heterocycle having from 4 to 8 atoms in the ring structure.

The terms "amine" and "amino" are art-recognized and refer to both unsubstituted and substituted amines and salts thereof, e.g., a moiety that can be represented by

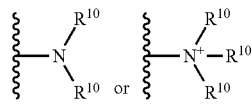

wherein each R$^{10}$ independently represents a hydrogen or a hydrocarbyl group, or two R$^{10}$ are taken together with the N atom to which they are attached complete a heterocycle having from 4 to 8 atoms in the ring structure.

The term "aminoalkyl", as used herein, refers to an alkyl group substituted with an amino group.

The term "aralkyl", as used herein, refers to an alkyl group substituted with an aryl group.

The term "aryl" as used herein include substituted or unsubstituted single-ring aromatic groups in which each atom of the ring is carbon. Preferably the ring is a 5- to 7-membered ring, more preferably a 6-membered ring. The term "aryl" also includes polycyclic ring systems having two or more cyclic rings in which two or more carbons are common to two adjoining rings wherein at least one of the rings is aromatic, e.g., the other cyclic rings can be cycloalkyls, cycloalkenyls, cycloalkynyls, aryls, heteroaryls, and/or heterocyclyls. Aryl groups include benzene, naphthalene, phenanthrene, phenol, aniline, and the like.

The term "carbamate" is art-recognized and refers to a group

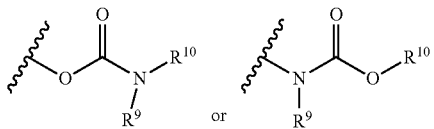

wherein R$^9$ and R$^{10}$ independently represent hydrogen or a hydrocarbyl group, such as an alkyl group, or R$^9$ and R$^{10}$ taken together with the intervening atom(s) complete a heterocycle having from 4 to 8 atoms in the ring structure.

The terms "carbocycle", and "carbocyclic", as used herein, refers to a saturated or unsaturated ring in which each atom of the ring is carbon. The term carbocycle includes both aromatic carbocycles and non-aromatic carbocycles. Non-aromatic carbocycles include both cycloalkane rings, in which all carbon atoms are saturated, and cycloalkene rings, which contain at least one double bond. "Carbocycle" includes 5-7 membered monocyclic and 8-12 membered bicyclic rings. Each ring of a bicyclic carbocycle may be selected from saturated, unsaturated and aromatic rings. Carbocycle includes bicyclic molecules in which one, two or three or more atoms are shared between the two rings. The term "fused carbocycle" refers to a bicyclic carbocycle in which each of the rings shares two adjacent atoms with the other ring. Each ring of a fused carbocycle may be selected from saturated, unsaturated and aromatic rings. In an exemplary embodiment, an aromatic ring, e.g., phenyl, may be fused to a saturated or unsaturated ring, e.g., cyclohexane, cyclopentane, or cyclohexene. Any combination of saturated, unsaturated and aromatic bicyclic rings, as valence permits, is included in the definition of carbocyclic. Exemplary "carbocycles" include cyclopentane, cyclohexane, bicyclo[2.2.1]heptane, 1,5-cyclooctadiene, 1,2,3,4-tetrahydronaphthalene, bicyclo[4.2.0]oct-3-ene, naphthalene and adamantane. Exemplary fused carbocycles include decalin, naphthalene, 1,2,3,4-tetrahydronaphthalene, bicyclo[4.2.0]octane, 4,5,6,7-tetrahydro-1H-indene and bicyclo[4.1.0]hept-3-ene. "Carbocycles" may be substituted at any one or more positions capable of bearing a hydrogen atom.

A "cycloalkyl" group is a cyclic hydrocarbon which is completely saturated. "Cycloalkyl" includes monocyclic and bicyclic rings. Typically, a monocyclic cycloalkyl group has from 3 to about 10 carbon atoms, more typically 3 to 8 carbon atoms unless otherwise defined. The second ring of a bicyclic cycloalkyl may be selected from saturated, unsaturated and aromatic rings. Cycloalkyl includes bicyclic molecules in which one, two or three or more atoms are shared between the two rings. The term "fused cycloalkyl" refers to a bicyclic cycloalkyl in which each of the rings shares two adjacent atoms with the other ring. The second ring of a fused bicyclic cycloalkyl may be selected from saturated, unsaturated and aromatic rings. A "cycloalkenyl" group is a cyclic hydrocarbon containing one or more double bonds.

The term "carbocyclylalkyl", as used herein, refers to an alkyl group substituted with a carbocycle group.

The term "carbonate" is art-recognized and refers to a group —OCO$_2$—R$^{10}$, wherein R$^{10}$ represents a hydrocarbyl group.

The term "carboxy", as used herein, refers to a group represented by the formula —CO$_2$H.

The term "ester", as used herein, refers to a group —C(O)OR$^{10}$ wherein R$^{10}$ represents a hydrocarbyl group.

The term "ether", as used herein, refers to a hydrocarbyl group linked through an oxygen to another hydrocarbyl group. Accordingly, an ether substituent of a hydrocarbyl group may be hydrocarbyl-O—. Ethers may be either symmetrical or unsymmetrical. Examples of ethers include, but are not limited to, heterocycle-O-heterocycle and aryl-O-heterocycle. Ethers include "alkoxyalkyl" groups, which may be represented by the general formula alkyl-O-alkyl.

The terms "halo" and "halogen" as used herein means halogen and includes chloro, fluoro, bromo, and iodo.

The terms "hetaralkyl" and "heteroaralkyl", as used herein, refers to an alkyl group substituted with a hetaryl group.

The term "heteroalkyl", as used herein, refers to a saturated or unsaturated chain of carbon atoms and at least one heteroatom, wherein no two heteroatoms are adjacent.

The term "heteroalkylamino", as used herein, refers to an amino group substituted with a heteralkyl group.

The terms "heteroaryl" and "hetaryl" include substituted or unsubstituted aromatic single ring structures, preferably 5- to 7-membered rings, more preferably 5- to 6-membered rings, whose ring structures include at least one heteroatom, preferably one to four heteroatoms, more preferably one or two heteroatoms. The terms "heteroaryl" and "hetaryl" also include polycyclic ring systems having two or more cyclic rings in which two or more carbons are common to two adjoining rings wherein at least one of the rings is heteroaromatic, e.g., the other cyclic rings can be cycloalkyls, cycloalkenyls, cycloalkynyls, aryls, heteroaryls, and/or heterocyclyls. Heteroaryl groups include, for example, pyrrole, furan, thiophene, imidazole, oxazole, thiazole, pyrazole, pyridine, pyrazine, pyridazine, and pyrimidine, and the like.

The term "heteroatom" as used herein means an atom of any element other than carbon or hydrogen. Preferred heteroatoms are nitrogen, oxygen, and sulfur.

The terms "heterocyclyl", "heterocycle", and "heterocyclic" refer to substituted or unsubstituted non-aromatic ring structures, preferably 3- to 10-membered rings, more preferably 3- to 7-membered rings, whose ring structures include at least one heteroatom, preferably one to four heteroatoms, more preferably one or two heteroatoms. The terms "heterocyclyl" and "heterocyclic" also include polycyclic ring systems having two or more cyclic rings in which two or more carbons are common to two adjoining rings wherein at least one of the rings is heterocyclic, e.g., the other cyclic rings can be cycloalkyls, cycloalkenyls, cycloalkynyls, aryls, heteroaryls, and/or heterocyclyls. Heterocyclyl groups include, for example, piperidine, piperazine, pyrrolidine, morpholine, lactones, lactams, and the like. Heterocyclyl groups can also be substituted by oxo groups. For example, "heterocyclyl" encompasses both pyrrolidine and pyrrolidinone.

The term "heterocycloalkyl", as used herein, refers to an alkyl group substituted with a heterocycle group.

The term "heterocycloalkylamino", as used herein refers to an amino group substituted with a heterocycloalkyl group.

The term "hydrocarbyl", as used herein, refers to a group that is bonded through a carbon atom that does not have a =O or =S substituent, and typically has at least one carbon-hydrogen bond and a primarily carbon backbone, but may optionally include heteroatoms. Thus, groups like methyl, ethoxyethyl, 2-pyridyl, and trifluoromethyl are considered to be hydrocarbyl for the purposes of this application, but substituents such as acetyl (which has a =O substituent on the linking carbon) and ethoxy (which is linked through oxygen, not carbon) are not. Hydrocarbyl groups include, but are not limited to, aryl, heteroaryl, carbocycle, heterocyclyl, alkyl, alkenyl, alkynyl, and combinations thereof.

The term "hydroxyalkyl", as used herein, refers to an alkyl group substituted with a hydroxy group.

The term "lower" when used in conjunction with a chemical moiety, such as, acyl, acyloxy, alkyl, alkenyl, alkynyl, or alkoxy is meant to include groups where there are ten or fewer non-hydrogen atoms in the substituent, preferably six or fewer. A "lower alkyl", for example, refers to an alkyl group that contains ten or fewer carbon atoms, preferably six or fewer. In certain embodiments, acyl, acyloxy, alkyl, alkenyl, alkynyl, or alkoxy substituents defined herein are respectively lower acyl, lower acyloxy, lower alkyl, lower alkenyl, lower alkynyl, or lower alkoxy, whether they appear alone or in combination with other substituents, such as in the recitations hydroxyalkyl and aralkyl (in which case, for example, the atoms within the aryl group are not counted when counting the carbon atoms in the alkyl substituent).

As used herein, the term "oxo" refers to a carbonyl group. When an oxo substituent occurs on an otherwise saturated group, such as with an oxo-substituted cycloalkyl group (e.g., 3-oxo-cyclobutyl), the substituted group is still intended to be a saturated group. When a group is referred to as being substituted by an "oxo" group, this can mean that a carbonyl moiety (i.e., —C(=O)—) replaces a methylene unit (i.e., —CH$_2$—).

The terms "polycyclyl", "polycycle", and "polycyclic" refer to two or more rings (e.g., cycloalkyls, cycloalkenyls, cycloalkynyls, aryls, heteroaryls, and/or heterocyclyls) in which two or more atoms are common to two adjoining rings, e.g., the rings are "fused rings". Each of the rings of the polycycle can be substituted or unsubstituted. In certain embodiments, each ring of the polycycle contains from 3 to 10 atoms in the ring, preferably from 5 to 7.

The term "silyl" refers to a silicon moiety with three hydrocarbyl moieties attached thereto.

The term "substituted" refers to moieties having substituents replacing a hydrogen on one or more carbons of the backbone. It will be understood that "substitution" or "substituted with" includes the implicit proviso that such substitution is in accordance with permitted valence of the substituted atom and the substituent, and that the substitution results in a stable compound, e.g., which does not spontaneously undergo transformation such as by rearrangement, cyclization, elimination, etc. As used herein, the term "substituted" is contemplated to include all permissible substituents of organic compounds. In a broad aspect, the permissible substituents include acyclic and cyclic, branched and unbranched, carbocyclic and heterocyclic, aromatic and non-aromatic substituents of organic compounds. The permissible substituents can be one or more and the same or different for appropriate organic compounds. For purposes of this invention, the heteroatoms such as nitrogen may have hydrogen substituents and/or any permissible substituents of organic compounds described herein which satisfy the valences of the heteroatoms. Substituents can include any substituents described herein, for example, a halogen, a hydroxyl, a carbonyl (such as a carboxyl, an alkoxycarbonyl, a formyl, or an acyl), a thiocarbonyl (such as a thioester, a thioacetate, or a thioformate), an alkoxyl, a phosphoryl, a phosphate, a phosphonate, a phosphinate, an amino, an amido, an amidine, an imine, a cyano, a nitro, an azido, a sulfhydryl, an alkylthio, a sulfate, a sulfonate, a sulfamoyl, a sulfonamido, a sulfonyl, a heterocyclyl, an aralkyl, or an aromatic or heteroaromatic moiety. It will be understood by those skilled in the art that substituents can themselves be substituted, if appropriate. Unless specifically stated as "unsubstituted," references to chemical moieties herein are understood to include substituted variants. For example, reference to an "aryl" group or moiety implicitly includes both substituted and unsubstituted variants.

The term "sulfate" is art-recognized and refers to the group —OSO$_3$H, or a pharmaceutically acceptable salt thereof.

The term "sulfonamide" is art-recognized and refers to the group represented by the general formulae

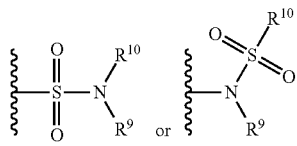

wherein R$^9$ and R$^{10}$ independently represents hydrogen or hydrocarbyl, such as alkyl, or R$^9$ and R$^{10}$ taken together with the intervening atom(s) complete a heterocycle having from 4 to 8 atoms in the ring structure.

The term "sulfoxide" is art-recognized and refers to the group —S(O)—R$^{10}$, wherein R$^{10}$ represents a hydrocarbyl.

The term "sulfonate" is art-recognized and refers to the group SO$_3$H, or a pharmaceutically acceptable salt thereof.

The term "sulfone" is art-recognized and refers to the group —S(O)$_2$—R$^{10}$, wherein R$^{10}$ represents a hydrocarbyl.

The term "thioalkyl", as used herein, refers to an alkyl group substituted with a thiol group.

The term "thioester", as used herein, refers to a group —C(O)SR$^{10}$ or —SC(O)R$^{10}$ wherein R$^{10}$ represents a hydrocarbyl.

The term "thioether", as used herein, is equivalent to an ether, wherein the oxygen is replaced with a sulfur.

The term "urea" is art-recognized and may be represented by the general formula

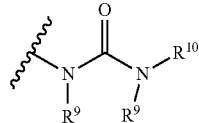

wherein R$^9$ and R$^{10}$ independently represent hydrogen or a hydrocarbyl, such as alkyl, or either occurrence of R$^9$ taken together with R$^{10}$ and the intervening atom(s) complete a heterocycle having from 4 to 8 atoms in the ring structure.

"Protecting group" refers to a group of atoms that, when attached to a reactive functional group in a molecule, mask, reduce or prevent the reactivity of the functional group. Typically, a protecting group may be selectively removed as desired during the course of a synthesis. Examples of protecting groups can be found in Greene and Wuts, *Protective Groups in Organic Chemistry*, 3$^{rd}$ Ed., 1999, John Wiley & Sons, NY and Harrison et al., *Compendium of Synthetic Organic Methods*, Vols. 1-8, 1971-1996, John Wiley & Sons, NY. Representative nitrogen protecting groups include, but are not limited to, formyl, acetyl, trifluoroacetyl, benzyl, benzyloxycarbonyl ("CBZ"), tert-butoxycarbonyl ("Boc"), trimethylsilyl ("TMS"), 2-trimethylsilyl-ethanesulfonyl ("TES"), trityl and substituted trityl groups, allyloxycarbonyl, 9-fluorenylmethyloxycarbonyl ("FMOC"), nitro-veratryloxycarbonyl ("NVOC") and the like. Representative hydroxylprotecting groups include, but are not limited to, those where the hydroxyl group is either acylated (esterified) or alkylated such as benzyl and trityl ethers, as well as alkyl ethers, tetrahydropyranyl ethers, trialkylsilyl ethers (e.g., TMS or TIPS groups), glycol ethers, such as ethylene glycol and propylene glycol derivatives and allyl ethers.

EXEMPLIFICATION

Example 1: Inhibition of the DosR Regulon by HC104A and HC106A

Figure 7:
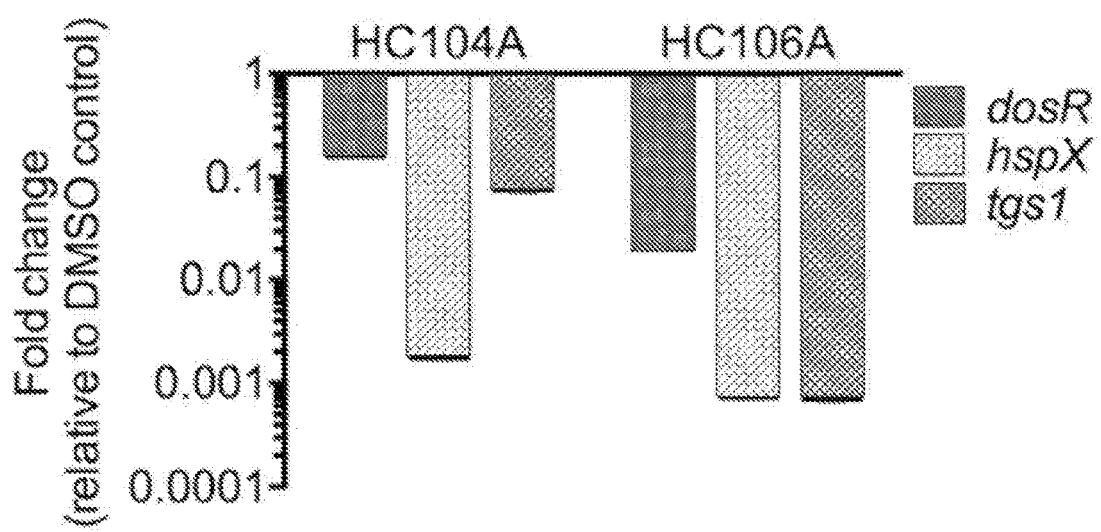
FIG. 7 shows inhibition of DosR regulon by HC104 and HC106A during hypoxia. Mtb cells were treated with 40 μM compounds for 6 d, and total bacterial RNA was isolated. The DosR regulated genes, dosR, hspX, and tgs1 were quantified in qRT-PCR. The error bars represent the s.d. of three replicates. The experiment was repeated at least twice with similar results.

Characterization studies were undertaken with two putative DosRST regulon inhibitors, HC104A and HC106A (FIG. 1, Part A). Half-maximal effective concentration (EC$_{50}$) studies using the CDC1551 (hspX'::GFP) DosRST-dependent fluorescent reporter strain, show that HC106A and HC106A inhibit DosRST-dependent GFP florescence with a EC$_{50}$ values of 9.8 μM and 2.48 μM, respectively (FIG. 1, Parts B and C). The compounds have minimal impact on Mtb growth, suggesting they are also potential DosRST inhibitors, as DosRST is not required for survival under the conditions of mild hypoxia used in the reporter-based assay. RNA-seq-based transcriptional profiling was undertaken to determine if the DosRST regulon was inhibited by the compounds. Mtb was treated with 40 μM HC104A, HC106A or DMSO control for 6 days in a standing flask, and following incubation RNA was extracted, sequenced and analyzed for differential gene expression relative to the DMSO control. As a control for the DosR regulon, transcriptional profiling was also previously conducted on a DMSO treated CDC1551(ΔdosR) mutant strain. The transcriptional profiles showed that the genes strongly repressed by HC104A and HC106A (>2-fold; q<0.05) are from dosR regulon, including Rv1738, hspX, Rv2028c, Rv2030, pfkB inhibited by HC104A, and tgs1, narX, fdxA, and Rv3131 by HC106A (FIG. 2, Parts A, B and C, Supplementary Dataset 1, 3). HC106A exhibited a remarkably strong reduction of gene expression, with transcripts for tgs1 and hspX being almost undetectably by RNA-seq following HC106A treatment. Interestingly, while HC106A broadly inhibited genes of the DosRST regulon, HC104A only strongly inhibited part of the DosR regulon, with the strongest inhibition reserved for hspX, the reporter promoter used to drive reporter fluorescence in the screen. These RNA-seq results were validated by semi-quantitative RT-PCR, with HC104A causing downregulation of dosR, hspX, and tgs1 in vitro by 6-, 570- and 13-fold, respectively; whereas HC106A downregulated these three genes by 49-, 1360-, and 1424-fold, respectively (FIG. 7), with hspX and tgs1 transcripts being below the level of detection by qRT-PCR.

Figure 2:
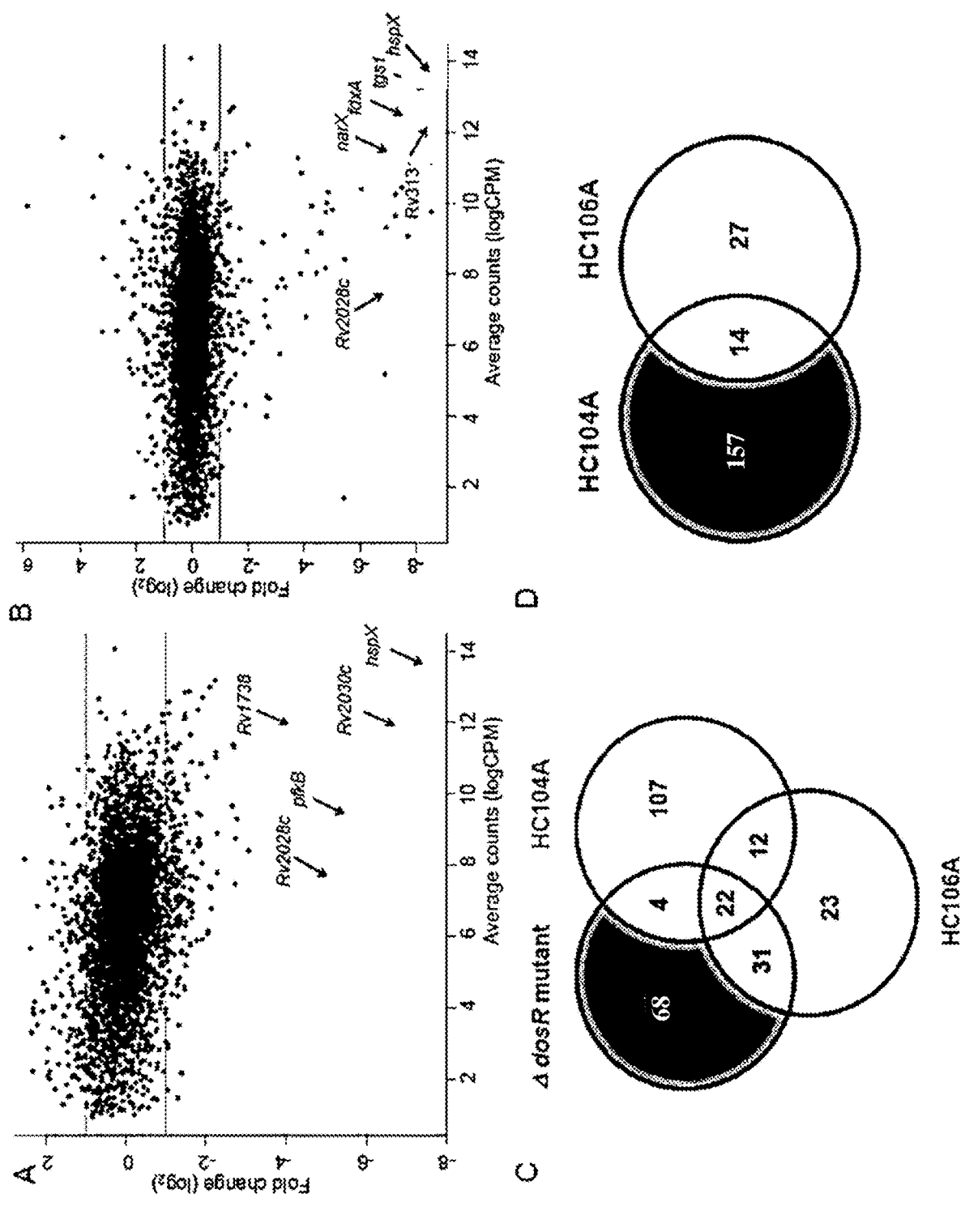
FIG. 2 has four parts, A-D, and shows transcriptional profiling shows HC104A and HC106A inhibited DosR regulon by during hypoxia. Magnitude-amplitude plots showing that Mtb cells treated with 40 µM HC104A (A) or HC106A (B). The labeled genes represent selected genes that belong to the DosRST regulon. The red dots represent genes with significant differential expression, q<0.05. (C) A Venn diagram for the downregulated genes (>2-fold; q<0.05) of WT CDC1551 treated with HC104A or HC106A compared to that of CDC1551 (ΔdosR). (D) Venn diagram for downregulated genes (>2-fold; q<0.05) of CDC1551 (ΔdosR) treated with HC104A or HC106A.

Comparisons of transcriptional profiles from the inhibitor treated WT Mtb strain to a CDC1551(ΔdosR) mutant strain showed that there are total 26 genes and 53 genes from dosR regulon inhibited by HC104A and HC106A, respectively. Notably, HC104A and HC106A have additional 119 genes and 35 genes repressed that were not repressed in the CDC1551(ΔdosR) mutant strain (FIG. 2, Part C). This observation suggested that these two compounds exhibit some DosR-independent activities. To confirmed the specificity of the compounds, RNA-seq was also performed on CDC1551(ΔdosR) mutant background (Supplementary Dataset 2-3) treated with HC104A or HC106A. This analysis identified 171 genes, and 51 genes that are downregulated (>2-fold; q<0.05) by HC104A, and HC106A, respectively (FIG. 2, Part D). This finding supports that HC104A and HC106A impact other targets beside DosR regulon, with HC106A showing greater on-target specificity than HC104A. Based on these findings, it was concluded that: 1) HC106A strongly and specifically inhibits the DosRST regulon; and 2) HC104A strongly inhibits a portion of the DosRST regulon, with serval notable off-target activities.

Figure 3:
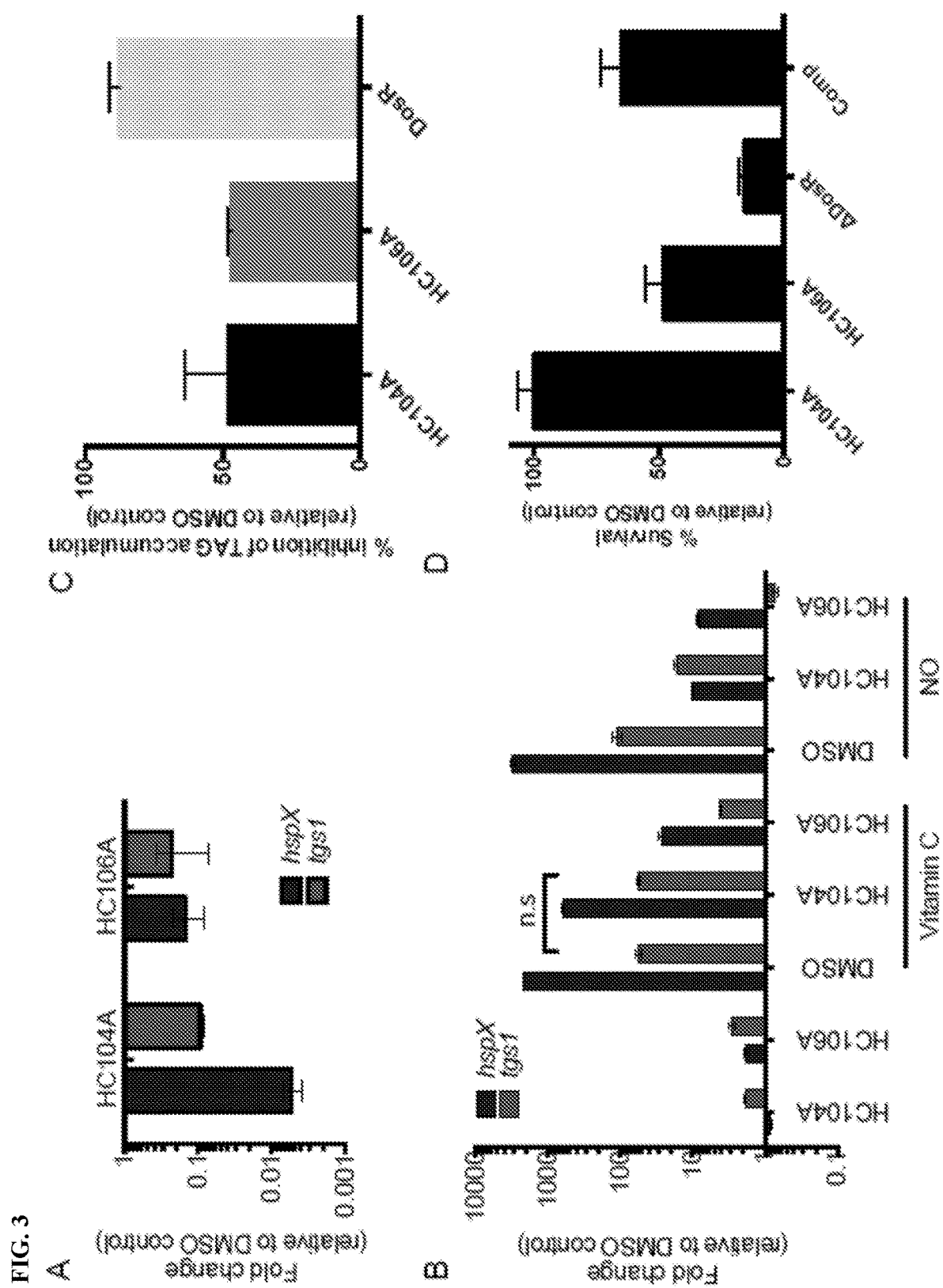
FIG. 3 has four parts, A-D, and shows inhibition of DosR regulon and persistence-associated physiologies by HC104A and HC106A. (A) Inhibition of DosR regulon in murine macrophages infected with Mtb and treated with HC104A and HC106A for 48 h. Bacterial RNA was isolated after incubation, and the differential gene expression of hspX and tgs1 bone-marrow derived were quantified in qRT-PCR. The error bar represents the s.d. of three biological replicates. (B) HC104A and HC106A inhibit DosR regulon induction by vitamin C and NO. Cells were pre-treated with the compounds or DMSO for 24 h, and induced with vitamin C or NO for 2 h. Total bacterial RNA was isolated, and the transcripts of DosR-regulated genes, hspX and tgs1, were quantified in qRT-PCR. The difference in the drug treated samples compared to DMSO treated samples in response to vitamin C or NO are significant with a p-value<0.001 based on T-test, except the one marked as non-significant (n.s.). The error bar represents the s.d. of three technical replicates. The experiment was repeated twice with similar results. (C) Inhibition of triacylglycerol (TAG) accumulation of Mtb treated with HC104A or HC106A. Mtb cells were treated with 40 µM of compounds and labeled with [1,2-$^{14}$C] sodium acetate for 6 d. Total lipid was isolated and analyzed in TLC. TAG accumulation was quantified from the TLC. The error bars represent the s.d. of two biological replicates. (D) Mtb cell survival during NRP when treated with HC104A or HC106A during NRP. Mtb cells were pretreated with 40 µM of compounds for 48 h in an anaerobic chamber, and continued incubation for 10 d. Survival bacteria were numerated on 7H10. The error bars represent the s.d. of three technical replicates. The experiment was repeated twice with similar results.

To access the impact of the inhibitors on the DosRST pathway on Mtb inside macrophages, murine bone marrow-derived mouse macrophages were infected with Mtb and treated with 40 μM HC104A and HC106A for 48 hours. Total bacterial total RNA was isolated and analyzed by RT-PCR for hspX and tgs1 gene differential expression. The results demonstrate that the induction of hspX and tgs1 were inhibited 185- and 10-fold by HC104A, and 6- and 4-fold by HC106A, respectively (FIG. 3, Part A). These finding support that HC104A and HC106A can access Mtb inside the macrophage, however, the reduced repression of the pathway by HC106A as compared to broth culture, supports that the molecule may not be able to efficiently target intracellular Mtb.

The DosRST pathway is also induced by redox signals such as vitamin C and NO. To examine whether these three compounds can repress the induction of DosRST pathway by vitamin C or NO, Mtb cells were pretreated with the compounds for 24 hours following by vitamin C or NO induction for 2 hours. The expression of DosR-regulated genes (hspX and tgs1) was examined by RT-PCR. Vitamin C and DETA-NONOate strongly induced hspX and tgs1 as previously reported (FIG. 3, Part B). For instance, vitamin C induced hspX and tgs1 by 2162- and 58-fold, respectively; whereas DETA-NONOate upregulated hspX and tgs1 3024-, and 113-fold, respectively (FIG. 3, Part B). Mtb cells pretreated with HC106A showed strongly inhibition of hspX and tgs1 induction by vitamin C and DETA-NONOate. For example, HC106A inhibited the hspX and tgs1 transcripts by 78- and 14-fold following vitamin C treatment, respectively, and 362- and 151-fold following DETA-NONOate treatment. Following vitamin C treatment, HC104 showed inhibition of hspX by 3.4-fold and no effect on tgs1, and 302- and 6.6-fold inhibition of hspX and tgs1 following DETA-NONOate treatment. These findings show that HC104A and HC106A act as an inhibitor of the DosRST pathway in response to hypoxia and redox signals.

Example 2: Inhibition of Mtb Persistence-Associated Physiologies

Figure 8:
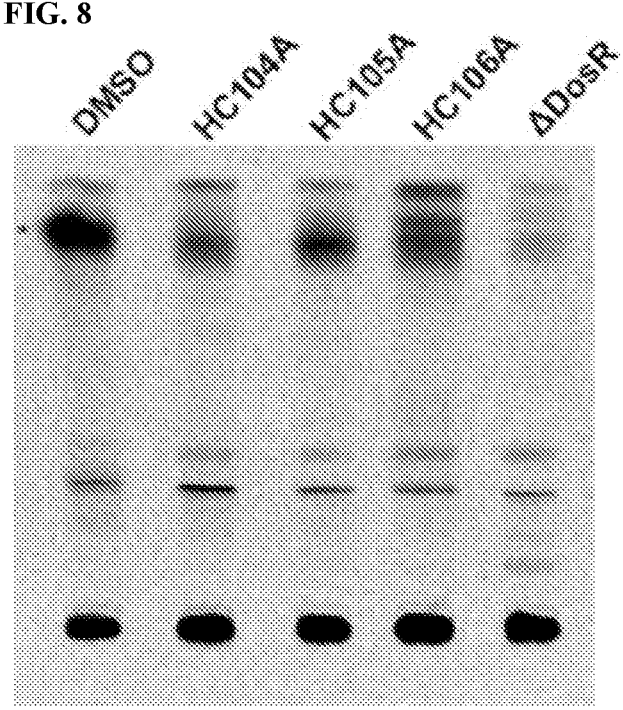
FIG. 8 shows TAG accumulation TLC of Mtb treated with HC104A and HC106A. Mtb cells were treated with 40 μM of compounds and labeled with [$1,2-^{14}C$] sodium acetate in T25 vented tissue culture flasks for 6 d. Total lipid was isolated and analyzed in TLC. The experiment was repeated twice with similar results.

Mtb accumulates triacylglycerol (TAG) during hypoxia. DosR directly regulates tgs1, which encodes a TAG synthase that is involved in the last step of TAG biosynthesis and is required for TAG accumulation during hypoxia. Transcriptional profiling showed that HC104A and HC106A repress tgs1. Based on this transcriptional profiling, it was hypothesized that these two compounds may inhibit TAG biosynthesis during NRP. To test this hypothesis, Mtb cells were radiolabeled with $^{14}C$-acetate and treated with HC104A or HC106A for 6 days. Lipids were isolated and analyzed by thin layer chromatography (TLC). As previously observed, DMSO treated CDC1551(ΔdosR) mutant displayed a strong 87% reduction of TAG accumulation as compared to DMSO treated WT (FIG. 3, Part C and FIG. 8). Mtb cells treated with HC104A or HC106A showed a significant, ~50% reduction of TAG accumulation, supporting this hypothesis that the compounds can inhibit TAG biosynthesis.

DosRST has been previously reported to be required for survival during NRP, where deletion of DosR causes greatly reduced survival during NRP. The impact of HC104A and HC106A on Mtb survival during NRP was examined using the hypoxic shift-down model. Mtb survival was examined following 10 days of treatment with the compounds at 40 μM. The ΔdosR mutant control had 15% survival relative to DMSO, and was partially complemented, supporting survival during hypoxia is DosR dependent. Mtb cells treated with HC106A displayed 50% survival relative to DMSO control (FIG. 3, Part D), whereas, HC104A had no impact on Mtb survival during NRP, an observation that suggests the portion of the DosR regulon inhibited by HC104A is not essential for survival during NRP.

Example 3: Inhibition of HC104A on DosR DNA Binding

Figure 9:
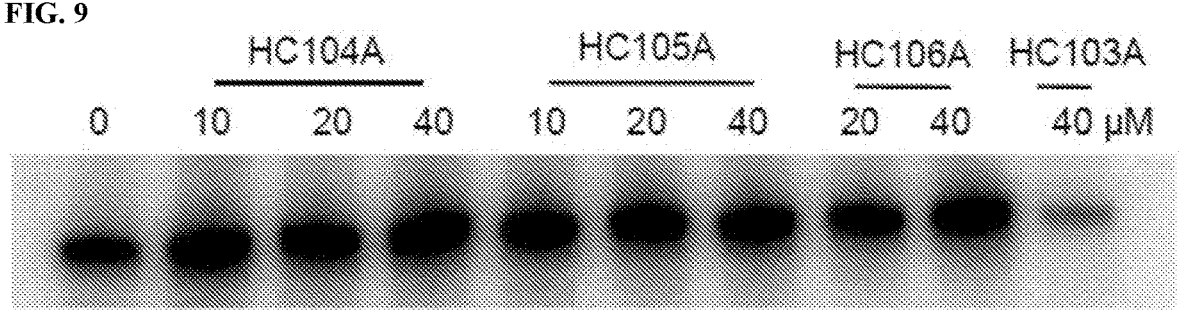
FIG. 9 shows an autoradiograph examining the impact of HC104A and HC106A on DosS autophosphorylation. DosS protein was treated with 10 μM, 20 μM or 40 μM of the compounds, with DMSO and HC103A as positive and negative controls, respectively. The results show that HC104A and HC106A have no effect on DosS autophosphorylation.

There are several potential targets of HC104A and HC06A to directly inhibit DosRST signaling, including: 1) direct inhibition of DosS/T sensor kinase activity, 2) modulation of the heme in the sensor, or 3) inhibition of DosR binding of DNA. To investigate biochemical mechanisms of action of HC104A and HC106A, inhibition of DosS autophosphorylation was initially evaluated. The DosS protein was treated with different concentrations of HC104A and HC106A from 10 μM to 40 μM, or 40 μM HC103A as a positive control, which previously was discovered as a DosS/T inhibitor. As previously observed, HC103A strongly inhibited DosS autophosphorylation, but HC104A and HC106A had no inhibitory activity (FIG. 9). This suggests HC104A and HC106A are not directly inhibiting sensor DosS/T autophosphorylation activity.

Figure 10:
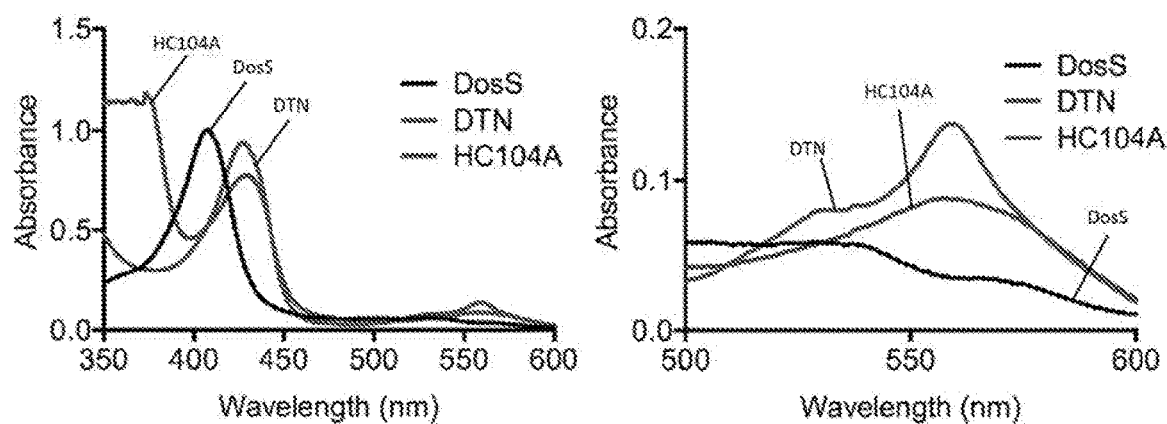
FIG. 10 shows an investigation of interaction between HC104A and DosS. WT DosS treated with 400 μM HC104A shows no impact on the position of the Soret peak in the UV-visible spectroscopy assay. The experiment was repeated at least twice with similar results.

Next, a UV-visible spectroscopy assay was employed to investigate if HC104A targets to the heme of sensor DosS. DosS protein reduced with dithionite (DTN) shifted the Soret peak to 430 nm as previously. However, addition of HC104A caused no change on to the overall spectrum, suggesting that HC104A does no modulate DosS heme redox (FIG. 10). Together, these data support that HC104A does not inhibit DosRST signaling by targeting these previously documented vulnerabilities in the sensor kinases.

Figure 4:
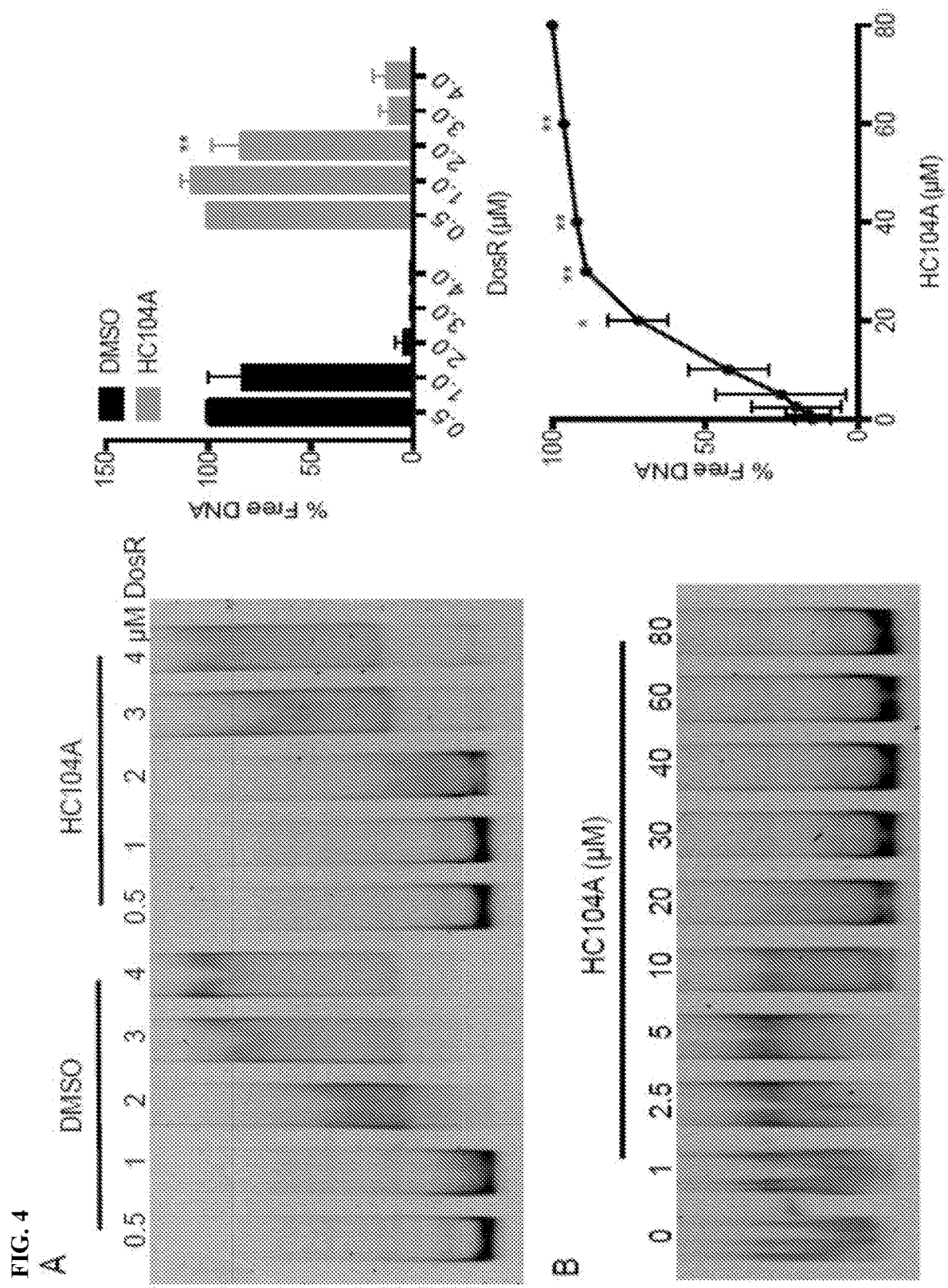
FIG. 4 has two parts, A-B, and shows inhibition of DosR DNA binding by HC104A. (A) DosR protein ranging from 0.5 µM to 4 µM was treated with DMSO or 40 µM HC104A and binding to the hspX promoter was examined by EMSA. HC04A inhibits DosR DNA binding at 2 µM concentration. The free DNA of each reaction was quantified in ImageJ, and the percentage of free DNA is normalized using reactions containing 0.5 µM DosR as 100% free DNA. Difference between reactions containing 2 µM DosR treated with DMSO or HC104A is significant (**P value<0.005 based on a t-test). The error bars represent the s.d. of two biological replicates. (B) Dose-response effect of HC104A on DosR DNA binding. DosR protein at 2 µM was treated across doses of HC104A from 1 µM to 80 µM. The free DNA of each reaction was also quantified in ImageJ, but the percentage of free DNA is normalized using the reaction containing 80 µM HC104A as 100% free DNA. The differences between treated reactions as compared to DMSO control are significant. (*P value<0.05 and **P value<0.005 based on a t-test). The error bars represent the s.d. of two biological reps.
Figure 5:
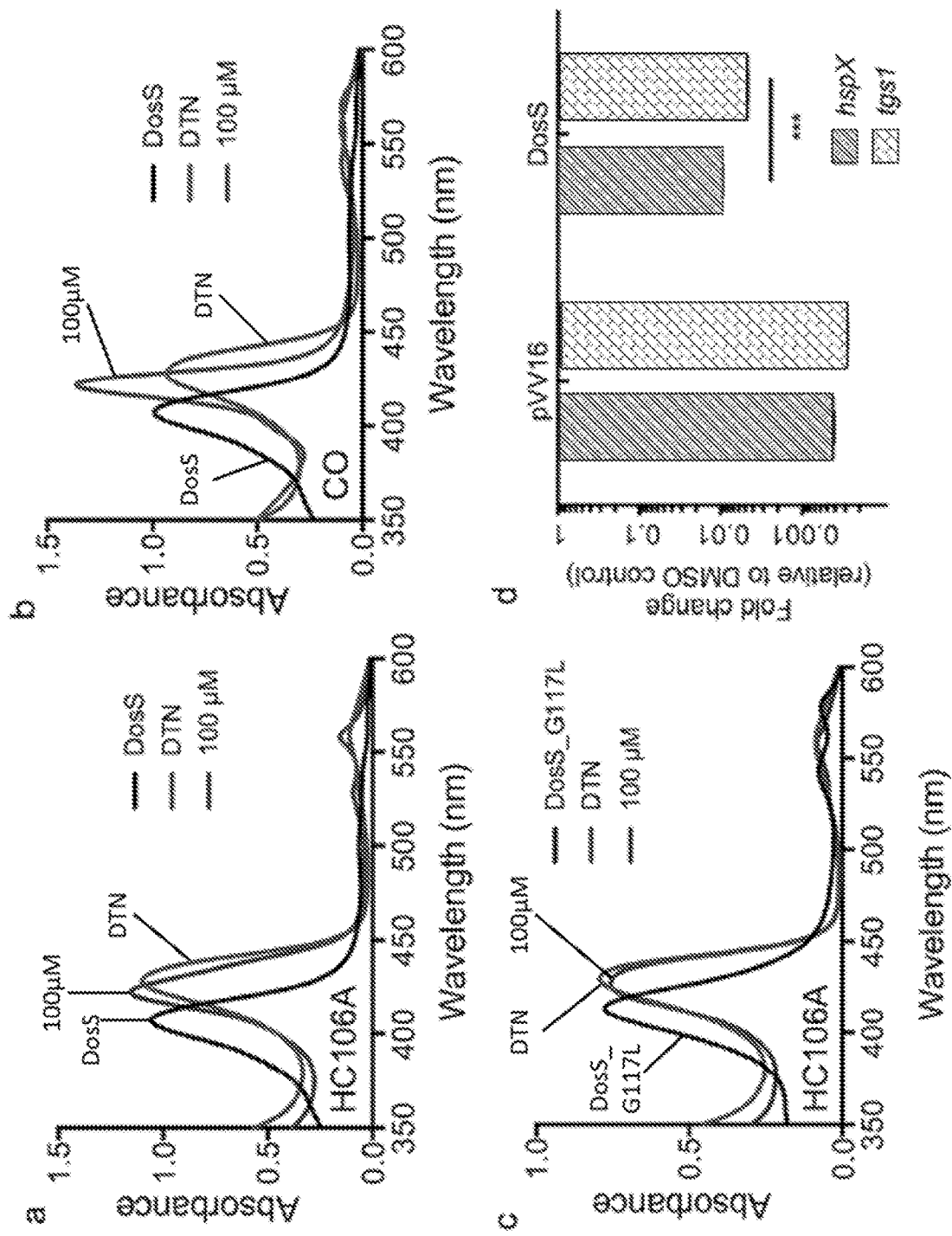
FIG. 5 has four parts, A-D, and shows interactions between HC106A and DosS heme. WT DosS protein was treated with 100 μM HC106A (A) or 100 μM tricarbonylchlororuthenium(II) dimer (CORM-2) (B), which is a CO donor. The UV-visible spectra between two treatments exhibited a shift of the Soret peak to a shared position of 422 nm. (C) DosS with a G117L substitution, that is predicted to block the heme exposing channel, provides resistance to HC106A. The spectrum of the mutant protein did not change, after HC106A treatment, indicating resistance to HC106A. (D) Overexpression of DosS protein promotes resistance to HC106A treatment in Mtb. Mtb cells with the pVV16 empty vector or the DosS overexpression plasmid were treated with 20 μM HC106A for 6 days. Bacterial RNA was isolated for analysis of the differential gene expression of hspX and tgs1 and analyzed by qRT-PCR. Overexpression of DosS caused 23- and 16.5-fold increase of hspX and tgs1 transcripts, respectively, compared to the empty vector control (***P value<0.0001 based on a t-test). The error bar represents the s. d. of the mean for three technical replicates. The experiments were repeated twice with a similar result.
Figure 11:
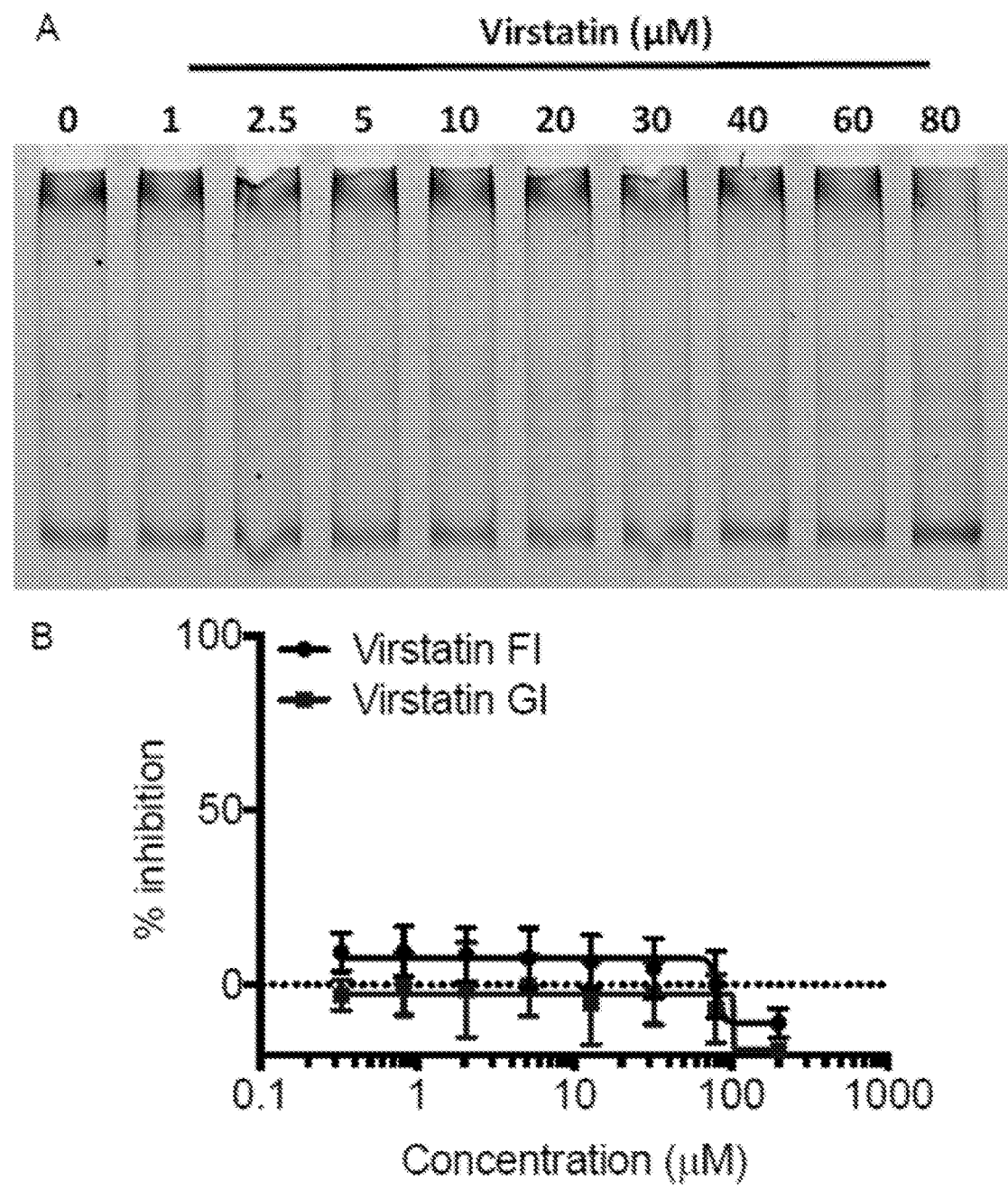
FIG. 11 has two parts, A-B, and shows the effect of virstatin on DosR DNA binding. (A) DosR protein at 2 μM were treated with 9 dose-point of virstatin from 1 μM to 80 μM. The reaction was analyzed on native PAGE gel. (B) Dose-response curve of virstatin shows not effect on inhibition of DosR-driven GFP fluorescence. The experiment was repeated at least twice with similar results.

Inspection of the HC104A structure revealed it had significant similarity to the compound virstatin. Virstatin is an anti-virulence compound that inhibits *Vibrio cholera* toxin production regulated by targeting the transcription regulator ToxT. Virstatin inhibits ToxT protein dimerization and subsequently interferes with DNA binding, thereby inhibiting the transcription of downstream genes involved in the toxin production. Based on the similarity of chemical structure between HC104A and virstatin, it was hypothesized that HC104A may be targeting DosR, and interfering with DNA binding. To test the hypothesis, an electrophoretic mobility shift assay (EMSA) was employed to investigate the effect of HC104A on DosR DNA binding. Recombinant DosR protein, ranging from 0.5 μM to 4 μM, was treated with 40 μM HC104A or a DMSO control and tested for binding of hspX promoter DNA. In the DMSO treated control, DosR bound promoter DNA beginning at a concentration 2 μM DosR protein (FIG. 5, Part A). Treated the reaction containing 2 μM DosR protein with HC104A significantly inhibited DNA binding by ~22-fold compared to DMSO control (FIG. 4, Part A). To further characterize the impact of HC104A on DosR binding of DNA, a dose-response study was performed. Reactions containing 2 μM recombinant DosR proteins were treated with different concentrations of HC104A or virstatin as control ranging from 1-80 μM. HC104A inhibited DosR binding of DNA beginning at 10 μM. The % of free DNA increased as HC104A concentration increased (FIG. 4, Part B). For example, the % free DNA was 72%, 89%. 92%, 96% and 100% for 20 μM, 30 μM, 40 μM, 60 μM and 80 μM HC104A, respectively, whereas DMSO control had 15% free DNA. This suggested HC104A significantly (*q<0.05, **q<0.005 based on T-test) inhibited DosR activity of DNA binding in a dose-dependent manner. Reactions treated with virstatin had no impact on DosR binding of DNA (FIG. 11, Part A). Consistent with these observations, virstatin did not have any impact on DosRST signaling in the whole cell Mtb fluorescence reporter assay (FIG. 11, Part B). These findings support the hypothesis that HC104A may function by inhibiting DosR DNA binding activity, and has an activity that is distinct form the related molecule virstatin.

Example 4: HC106A Modulates DosS Heme

DosS and DosT have a channel that exposes the heme to the environment and enables interactions with gases. This channel is an Achilles heel that can be targeted by small molecules. Previously, it was shown that the artemisinin could modulate DosS/T by oxidizing and alkylating heme carried by the kinases. UV-visible spectroscopy studies were conducted to examine if HC106A modulated DosST heme. Recombinant DosS was purified from *E. coli*, degassed and heme redox was monitored under anaerobic conditions by UV-visible spectroscopy. Treating DosS with the reducing agent DTN caused the Soret peak to shift to 430 nm as shown previously. HC106A was added to the reaction following DTN treatment to observe the impact on the DosS heme UV-visible spectrum. HC106A caused the DosS Soret peak to immediately shift to 422 nm, where the peak was stably maintained for 2 h (FIG. 5, Part A). This spectrum shift is different from artemisinin, where under identical conditions, artemisinin causes the DosS Soret peak to gradually shift back to the oxidized state at 403 nm. These findings show that HC106A may also interact with the sensor kinase heme, but via a mechanism that is distinct from artemisinin-heme interactions.

The Soret peak at 422 nm is consistent with previously described spectra that are observed when DosS heme interacts with NO or CO. To confirm this observation, DosS treated with 100 μM CO which caused a shift of the Soret peak to 422 nm, similar to HC106A (FIG. 5, Part B). This finding supports that HC106A may be directly binding to the heme, in a similar manner to CO. Notably, CO activates DosS kinase function, whereas HC106A functions to inactivate the regulon, demonstrating that the impact of heme binding by CO or HC106A has differing impacts on the sensor kinase switch.

Figure 12:
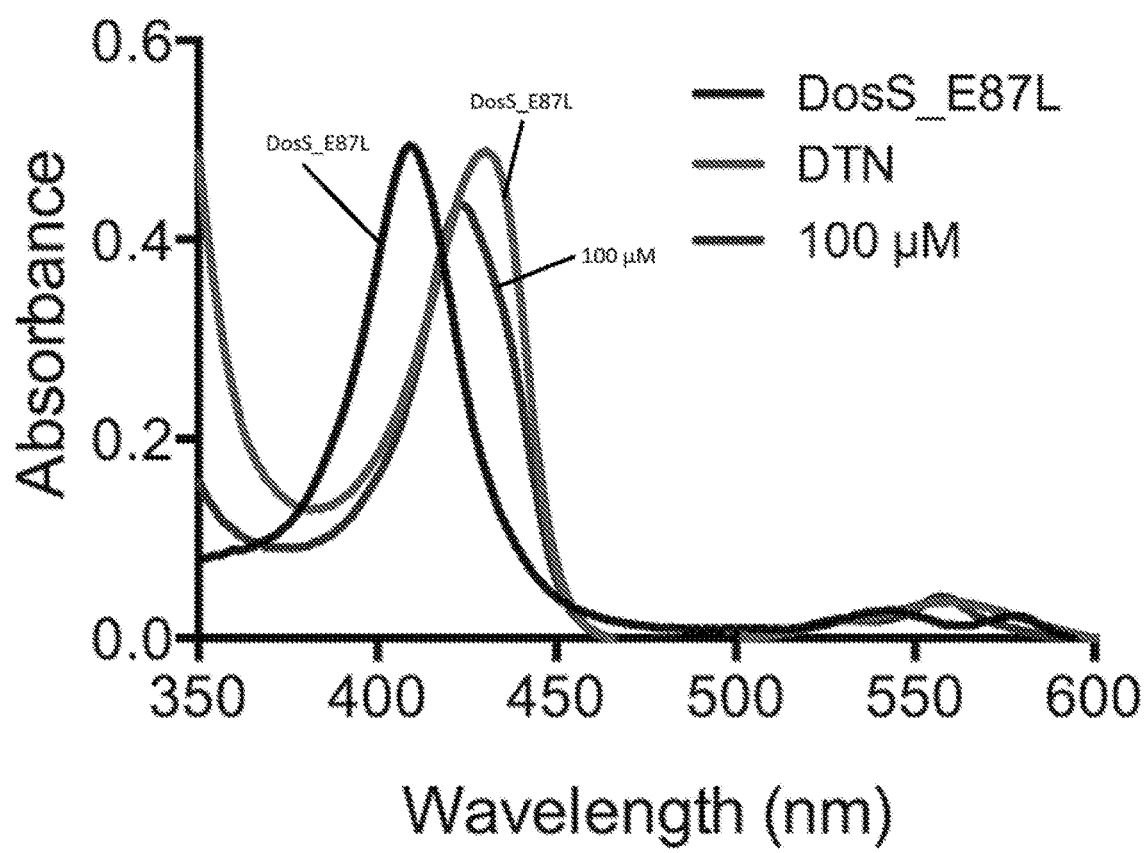
FIG. 12 shows an investigation of the interaction between HC106A and DosS heme. DosS E87L protein was treated with 100 μM HC106A after reduced with DTN. The UV-visible spectra were recorded after each treatment, and showed no change on overall spectrum. The experiment was repeated at least twice with similar results.

Amino acid substitutions in the channel exposing the DosS heme to the environment, such as DosS E87L or G117L, can limit access of artemisinin to modulate heme. To support the hypothesis that HC106A directly targets DosS heme, the impact of these amino acid substitutions on HC106A/DosS heme interactions was tested. Treating DosS (E87L) with HC106A exhibited a profile similar to wild type DosS with the Soret peak shifting to 422 nm (FIG. 12). However, DosS(G117L) had no change to the overall spectrum after HC106A treatment (FIG. 5, Part C). This finding supports that DosS(G117L) is resistant to HC106A, and supports that HC106A accesses the heme via a similar mechanism as artemisinin.

To confirm DosS is the target of HC106A in Mtb, the impact of overexpressing DosS protein in Mtb was examined. If DosS is the target of HC106A, overexpression may reduce the effectiveness of HC106A. WT DosS protein was constitutively expressed from the hsp60 promoter in Mtb. The vector control showed that both hspX and tgs1 genes were downregulated by HC106A by 2331- and 3470-fold, respectively (FIG. 5, Part D). Overexpressing DosS provided significant resistance to HC106A, with hspX and tgs1 inhibited only 23- and 16.5-fold, respectively. This observation of resistance in Mtb is consistent with the biochemical data supporting that DosS is a direct target of HC106A.

Example 5: Synergistic Effects Between DosRST Inhibitors

Figure 6:
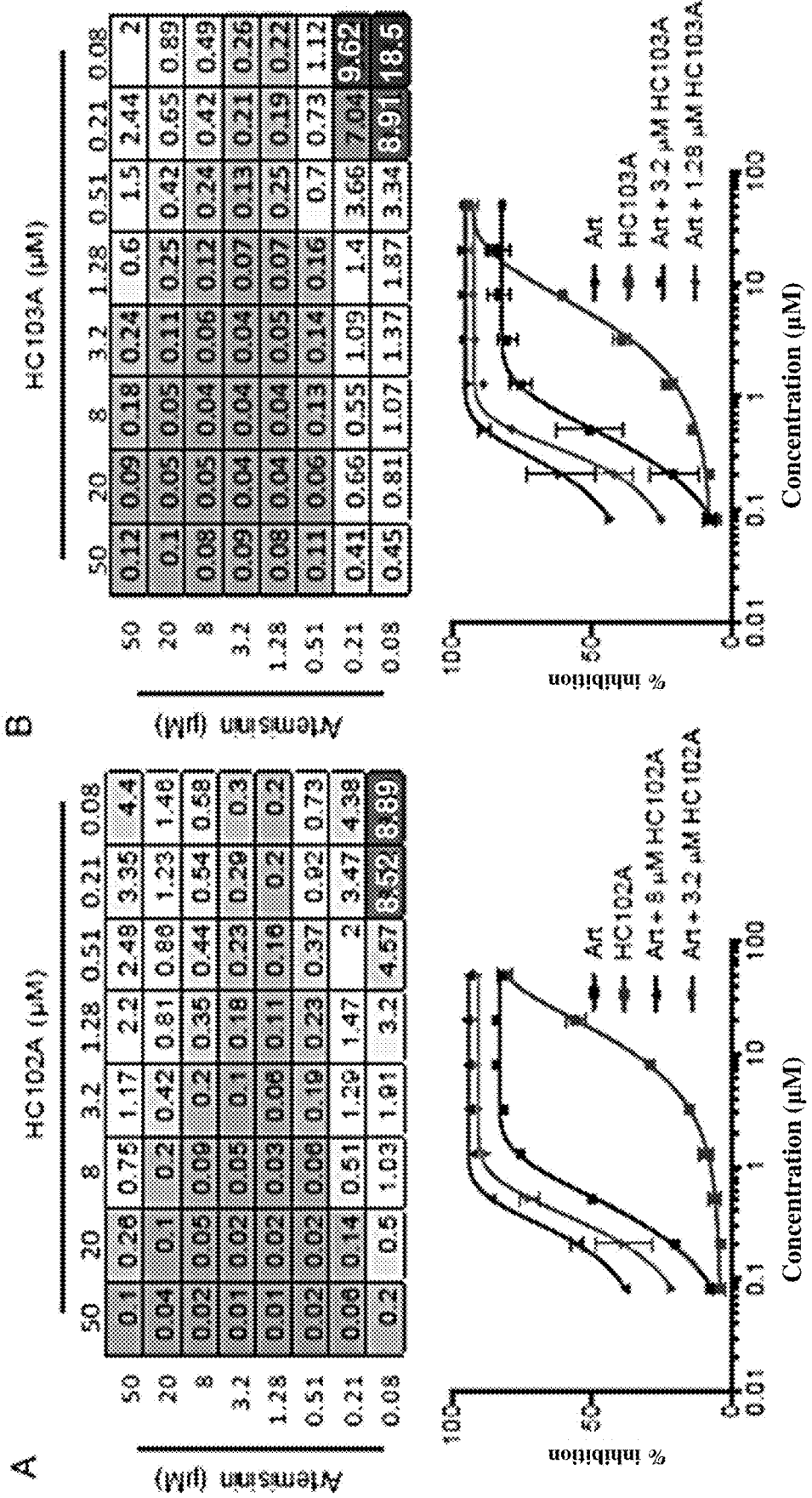
FIG. 6 has four parts, A-D, and shows synergistic effects between DosRST inhibitors. CDC1551 (hspX'::GFP) was treated with pairwise combinations of two compounds at concentrations of 50 μM to 0.08 μM. GFP fluorescence was measured and used to calculate percentage inhibition. The data were analyzed in the CompuSyn software to determine the combination index (CI) for the panel of each drug combination, including (A) artemisinin and HC102A; (B) artemisinin and HC103A; (C) artemisinin and HC104A; and (D) artemisinin and HC106A. Example $EC_{50}$ curves are presented with individual compounds or a selected synergistic combination to illustrate the potentiating interactions.
Figure 6:
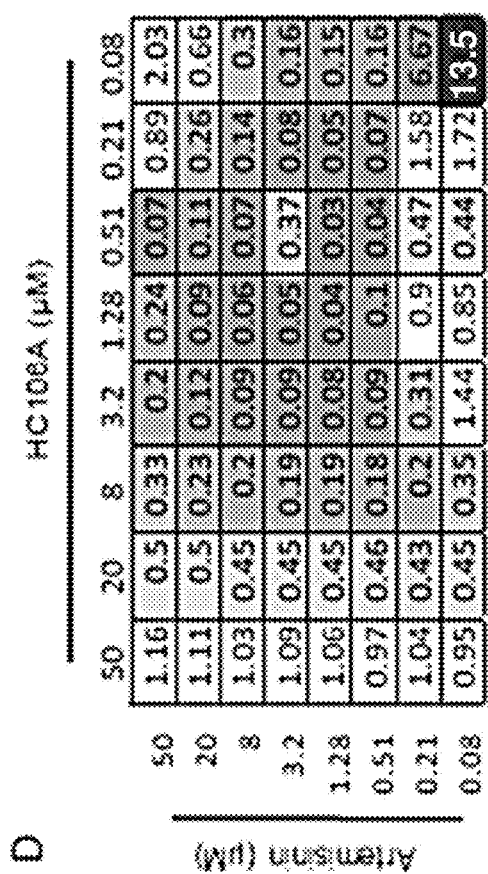
Figure 6:
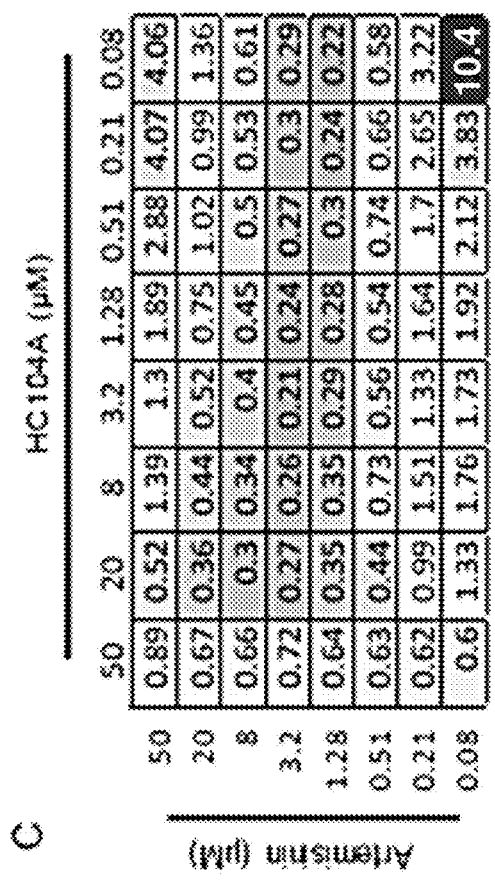
Figure 6:
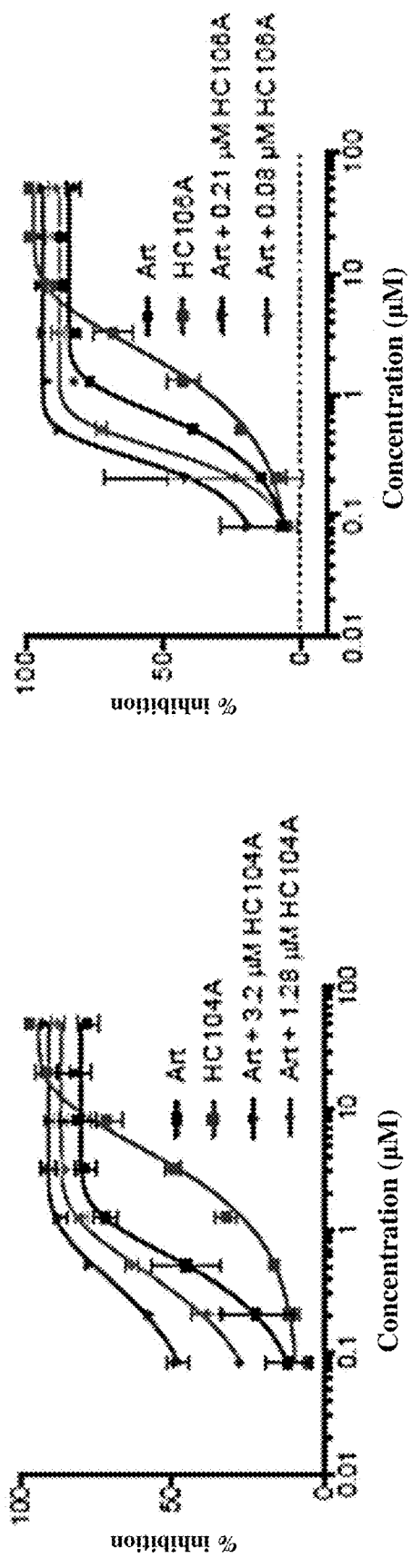
Figure 13:
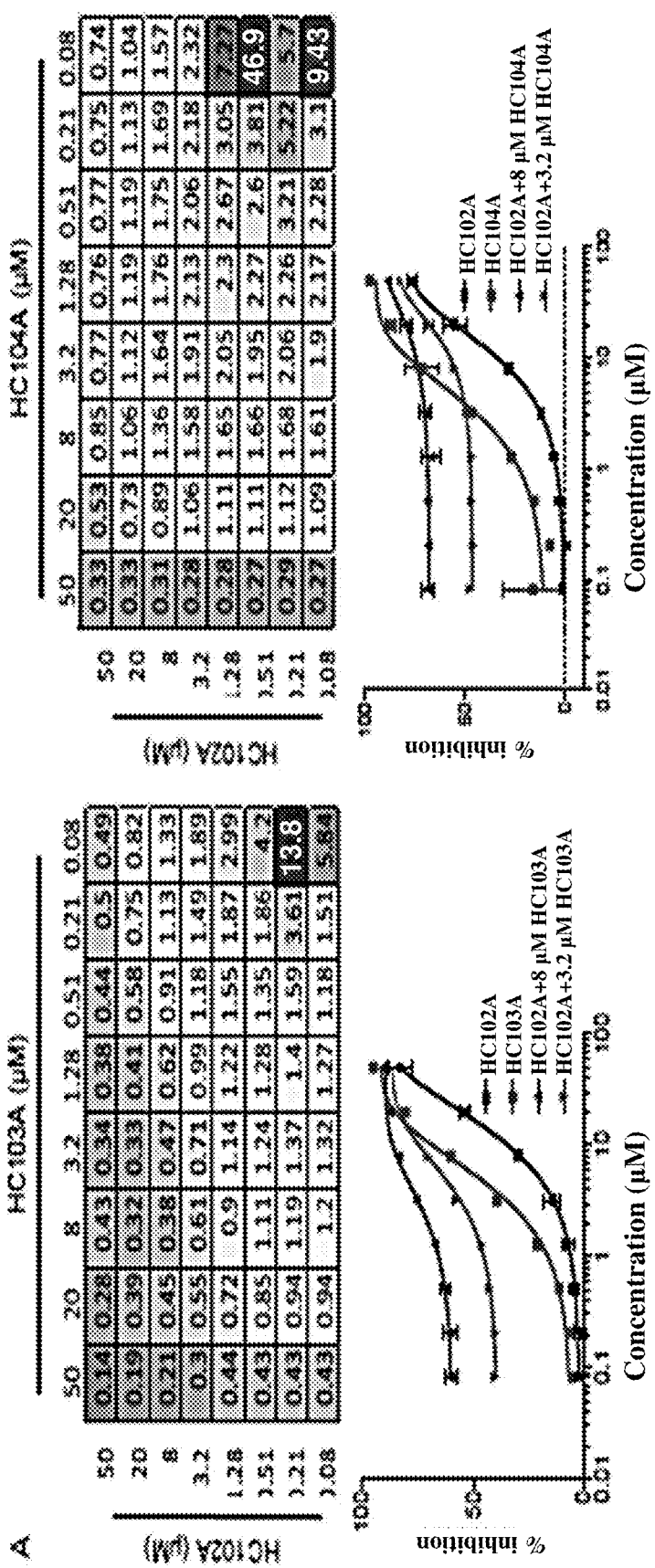
FIG. 13 has seven parts, A-G, and shows checkerboard assays examining paired interactions of DosRST inhibitors. CDC1551 (hspX'::GFP) was treated with different combination of two compounds from 50 μM to 0.08 μM. GFP fluorescence was measured and used to calculate percentage inhibition. The data were analyzed in the CompuSyn software to determine the combination index (CI) for the panel of each drug combination, including (A) artemisinin and HC104A; (B) HC102A and HC103A; (C) HC102A and HC104A; (D) HC102A and HC106A; (E) HC103A and HC104A; (F) HC103A and HC106A; (G) HC104A and HC106A. Selected dose response curves are presented to illustrate synergistic interactions. The experiment was repeated twice with similar results.
Figure 13:
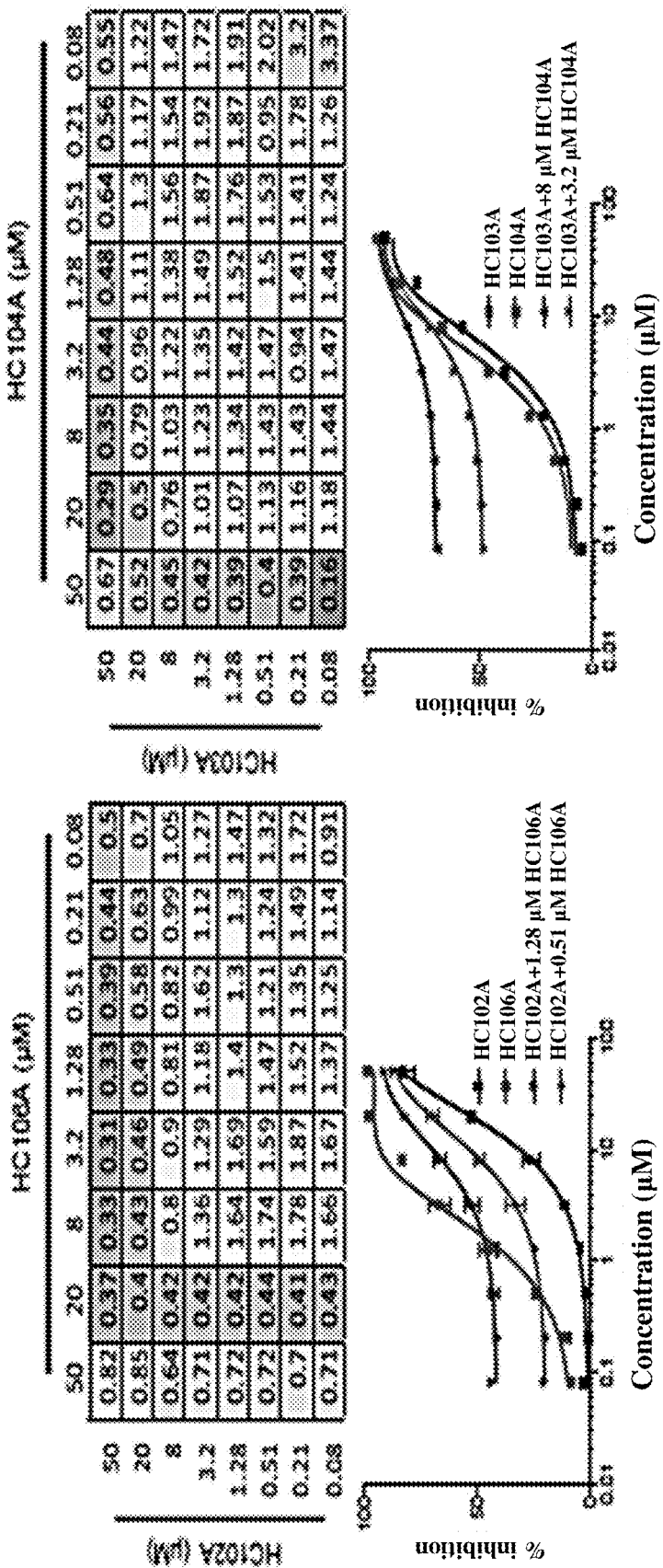
Figure 13:
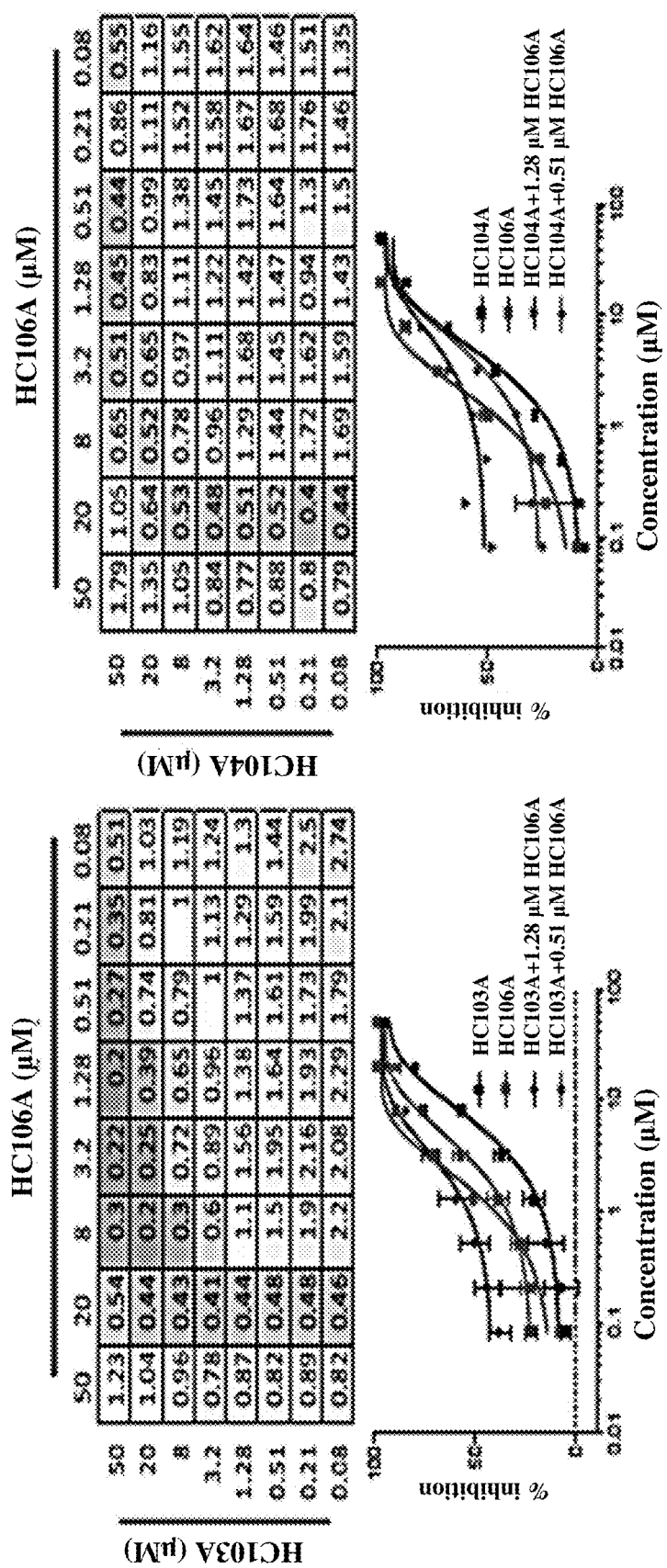
Figure 14:
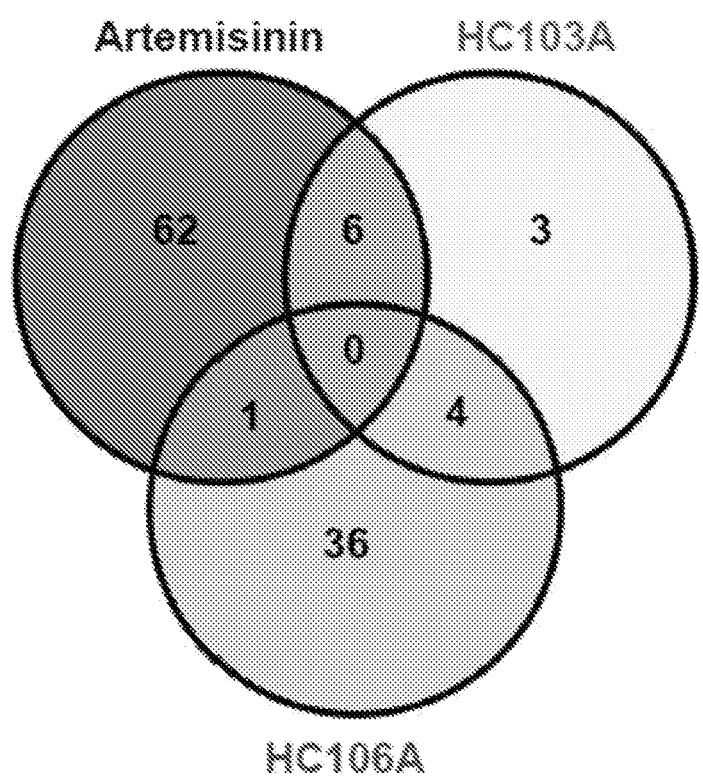
FIG. 14 shows the comparison between artemisinin, HC103 and HC106 for off-targets. A Venn diagram for the downregulated genes (>2-fold; q<0.05) of CDC1551 (ΔdosR) treated with artemisinin, HC103A, or HC106A.

With multiple distinct inhibitory activities of the HC101A, HC102A, HC103A, HC104A and HC106A, potentiating or antagonistic interactions existed between the molecules, when targeting the DosRST pathway, was examined. To examine these interactions, checkerboard assays were performed with pairwise comparisons of artemisinin (HC101A), HC102A, HC103A, HC104A and HC106A. CDC1551 (hspX'::GFP) was treated with combinations of two compounds ranging from 50 μM to 0.08 μM in 96-well plates. DosR-driven GFP fluorescence and optical density were measured following 6 days of treatment. The Combination Index (CI) was calculated for each drug pair based on the Chou-Talalay method in the CompuSyn software package, where CI values of <1, =1 and >1 indicate synergistic, additive or antagonistic interactions, respectively. Among all 64 compound pairs, artemisinin combined with HC102A, HC103A, HC104A and HC106, showed 46, 49, 41, and 50 combinations that have CI<1, respectively (FIG. 6). Notably, some CI values are below 0.1 when artemisinin was paired with HC102A, HC103A or HC106A combinations. Example dose response curves illustrate these synergistic interactions (FIG. 6). Several other pairwise comparisons also demonstrated synergy (FIG. 13), however, in general, these interactions had CI between 1 and 0.1, supporting weaker synergistic interactions, as compared to combinations with artemisinin. Overall, these studies provide the evidences that the inhibitors function by distinct mechanisms and may be combined to improve potency.

Example 6: Structure-activity Relationship Study for HC106

A catalog search for HC104 and HC106 analogs and obtained 10 commercial analogs for each series to define initial structure activity relationships (SAR) was conducted. For HC104A it was observed that a bromine in the 5-position of is required for activity and that the $R^2$ dimethylamine group is not required (Table 3). For example, HC104B is identical to HC104A except for the removal of the bromine ($R^1$), which results in a complete loss of activity in the whole cell assay. Whereas, replacement of the $R^2$ group with a methyl (HC104G) results in an active compound, although ~5-fold less active than HC104A. Although not highly potent, its ligand efficiency, c Log D and druglikeness are in the range of what would be considered acceptable to good as a starting point for further manipulation. For HC106A (Table 2), catalog SAR work led to new understandings of the nature of the series. Simple removal of an ortho chloro on the "A" ring of HC106A leads to ~ 2-fold enhanced activity, with an $EC_{50}$ in the whole cell Mtb assay for DosRST inhibition of 1.33 µM (HC106F). It was also found that the use of an alternative isomer of the isoxazole had no activity (HC106C). MSU-41424 fits outside the genus . . . . Remove?? Is this table really necessary, Not clear that we need to explain or demonstrate SAR to others.

TABLE 3

| | Compound | |
|---|---|---|
| ID# | HC104A | HC104G | HC104B |
| MW (g/mole) | 361.2 | 290.1 | 282.3 |
| $EC_{50}$ (µM) | 9.8 | 43.8 | >200 |
| Ligand Efficiency | 0.34 | 0.36 | 0.26 |
| CLogP (cLogD at pH 7.4) | 3.0 (0.55) | 2.3 (2.4) | 2.9 (−0.24) |
| Druglikeness | 4.4 | 0.55 | 6.2 |

TABLE 4

The Early SAR studies of HC106 series. The HC106 analogs with different R-groups were synthesized or purchased. The reporter strain CDC1551 (hspX'::GFP) was treated with across doses of each analog from 200 µM to 0.328 µM. The $EC_{50}$ values of fluorescence inhibition (FI) calculated for each analog to determine their potency.

| ID# | Compound | $EC_{50}$ (µM) |
|---|---|---|
| HC106F | | 1.33 |
| HC106A | | 2.48 |
| HC106C | | >200 |
| MSU-39450 | | 1.95 |
| MSU-39444 | | 1.7 |
| MSU-41324 | | >200 |
| MSU-39449 | | 5.2 |
| MSU-39451 | | 4.14 |
| MSU-39453 | | 16.62 |
| MSU-41422 | | >200 |

To further understand the SAR of the HC106 series, additional analogs were prepared to understand the need of the central urea functionality and whether modifications can be tolerated (Table 5). A pyridyl analog, designed to replace the isoxazole also demonstrated no activity as was the symmetrical 4-chloroaniline derived urea (MSU-41324). However, the bis-isoxazole urea (MSU-39444) provides an $EC_{50}$ of 1.7 μM, noting that the isoxazole is essential for binding. Isoxazoles are unique among heterocycles in that they exist in multiple tautomeric forms. This is supported by initial NMR studies, and will help define mechanistic insights. Next, the need of one of the —NHs of the urea, capping it with a methyl (MSU-39451), integrating it into a ring for conformational restriction (MSU-39453), and a —$CH_2$— (MSU-39449) was explored. In all cases, reduced activity (0.5-1 log) was observed but not all activity was lost. Thus, HC106A is a potent whole cell inhibitor of the DosRST pathway, with flexibility to be improved via SAR.

TABLE 5

Initial Topliss Tree evaluation of "A-ring" aniline of series HC106. The HC106 analogs with different R-groups were synthesized. The reporter strain CDC1551 (hspX'::GFP) was treated with across doses of each analog from 200 μM to 0.328 μM. The EC$_{50}$ values of fluorescence inhibition (FI) calculated for each analog to determine their potency. The other chemical properties of the analogs are also included.

| ID# | Compound R = | EC$_{50}$ (μM) | MW (g/mol) | TPSA (ang$^2$) | Ligand Efficiency (LE) | m.p. (°C) | cLogP | Solubility (μM) | Microsomes (% remaining @ 30 minutes) |
|---|---|---|---|---|---|---|---|---|---|
| H106F | 4-Cl-phenyl-NH-* | 1.33 | 237.6 | 63 | 0.50 | 183 | 2.2 | >200 | 115% |
| HC106A | 2,4-diCl-phenyl-NH-* | 2.48 | 272.1 | 63 | 0.41 | 164 | 2.7 | 110 | — |
| MSU-33189 | phenyl-NH-* | 0.63 | 203.1 | 63 | 0.56 | 183-184 | 1.6 | — | — |
| MSU-39447 | 4-MeO-phenyl-NH-* | 0.61 | 233.2 | 72 | 0.49 | 166-167 | 1.5 | >100 | — |
| MSU-39448 | 6-Cl-pyridin-3-yl-NH-* | 1.42 | 238.6 | 75 | 0.49 | 158-159 | 1.3 | — | — |
| MSU-39450 | 5-Cl-pyridin-2-yl-NH-* | 1.95 | 238.6 | 75 | 0.38 | 122-123 | 1.3 | — | — |
| MSU-39446 | 4-F-phenyl-NH-* | 0.54 | 221.2 | 63 | 0.52 | 176-177 | 1.7 | >100 | 70% |
| MSU-41464 | 4-Br-phenyl-NH-* | 1.2 | 282.1 | 67 | 0.51 | 183-184 | 2.3 | — | 109% |
| MSU-39445 | 3-Cl-phenyl-NH-* | 0.75 | 237.6 | 63 | 0.52 | 159 (dec) | 2.1 | >100 | — |

TABLE 5-continued

Initial Topliss Tree evaluation of "A-ring" aniline of series HC106. The HC106 analogs with different R-groups were synthesized. The reporter strain CDC1551 (hspX'::GFP) was treated with across doses of each analog from 200 μM to 0.328 μM. The $EC_{50}$ values of fluorescence inhibition (FI) calculated for each analog to determine their potency. The other chemical properties of the analogs are also included.

| ID# | Compound R = | $EC_{50}$ (μM) | MW (g/mol) | TPSA (ang$^2$) | Ligand Efficiency (LE) | m.p. (°C) | cLogP | Solubility (μM) | Microsomes (% remaining @ 30 minutes) |
|---|---|---|---|---|---|---|---|---|---|
| MSU-39452 | 3,4-dichlorophenyl | 2.47 | 272.1 | 63 | 0.45 | 164 | 2.8 | — | — |
| MSU-41442 | 4-t-Bu-phenyl | 2.08 | 259.3 | 63 | 0.41 | 163 | 3.1 | >100 | — |
| MSU-41443 | 4-biphenyl | 11.2 | 279.3 | 63 | 0.32 | 193 | 3.2 | 14 | — |
| MSU-41463 | 4-CF$_3$-phenyl | 1.67 | 271.2 | 67 | 0.42 | 178 | 2.4 | — | 84 |
| MSU-41465 | 4-(methoxycarbonyl)phenyl | 1.16 | 261.2 | 94 | 0.43 | 194 | 1.5 | — | 73 |
| MSU-41462 | benzyl | 1.12 | 217.2 | 67 | 0.45 | 128-130 | 1.3 | — | — |
| MSU-41542 | isobutyl | 1.34 | 183.2 | 67 | 0.62 | 187 | 0.9 | — | — |
| MSU-41545 | 4-(benzyloxy)phenyl | 4.75 | 309.3 | 76 | 0.32 | 164 | 2.9 | — | — |
| MSU-41546 | cyclopentyl | 2.15 | 195.2 | 67 | 0.56 | 182 | 1.1 | — | — |

TABLE 5-continued

Initial Topliss Tree evaluation of "A-ring" aniline of series HC106. The HC106 analogs with different R-groups were synthesized. The reporter strain CDC1551 (hspX'::GFP) was treated with across doses of each analog from 200 μM to 0.328 μM. The $EC_{50}$ values of fluorescence inhibition (FI) calculated for each analog to determine their potency. The other chemical properties of the analogs are also included.

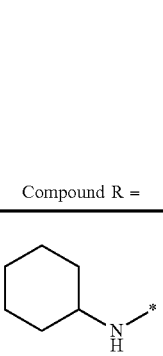

| ID# | Compound R = | $EC_{50}$ (μM) | MW (g/mol) | TPSA ($ang^2$) | Ligand Efficiency (LE) | m.p. (°C) | cLogP | Solubility (μM) | Microsomes (% remaining @ 30 minutes) |
|---|---|---|---|---|---|---|---|---|---|
| MSU-42002 | 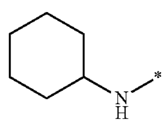 [SMILES: *NC1CCCCC1]  | 1.21 | 209.2 | 67 | 0.54 | 180 | 1.4 | — | — |
| MSU-42003 | 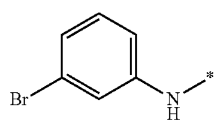 [SMILES: *Nc1cccc(Br)c1]  | 1.94 | 282.1 | 67 | 0.49 | 157 | 2.3 | — | — |
| MSU-42004 | 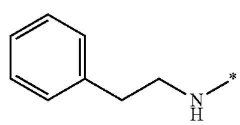 [SMILES: *NCCc1ccccc1]  | 2.36 | 231.3 | 67 | 0.45 | 165 | 1.7 | — | — |

To further test the SAR, a Topliss Tree evaluation of the "A-ring" aniline was performed. To reliably prepare the derivatives, a general preparation was established (Scheme 1). This route is preferred relative to alternative approaches for its cleanliness, yields and ease of purification, usually by trituration. It is also anticipated that it will also allow access into future derivatives. Using HC106F and HC106A as starting points, the 3,4-diclorochloro and 3-chloro derivatives (MSU-39452 and MSU-39445, respectively) were prepared. Both the 3- and 4-chloro derivatives demonstrated greater activity than 3,4-dichloro (MSU-39452). Replacing the 4-chlorophenyl ring with pyridyl analogs (MSU-39448 and MSU-39450) lead to increased activity. Focusing on 4-position derivatives, fluoro (MSU-39446), bromo (MSU-41464) and methoxy (MSU-39447), as electron p-orbital donating substituents, also lead towards increased activity. Para-t-butyl phenyl (MSU-41442), also did the same. Electron withdrawing substituents, such as 4-$CO_2$Me (MSU-4165), 4-trifluoromethyl (MSU-41463) and biphenyl (MSU-41 443) saw similar activity. Overall, several analogs were discovered with significantly ~4-fold enhanced potency, with several inhibitors having whole cell DosrRST inhibitory $EC_{50}$ below 1 μM, including $EC_{50}$ of 0.63 μM, 0.61 μM, 0.54 μM and 0.75 μM for MSU-33189, -39447, -39446, and -39455. The parent analog HC106A had an $EC_{50}$ of 2.3 μM.

Example 7: Discussion

DosRST is a two-component regulatory system required for Mtb environmental sensing, adaptation, and persistence. By using a fluorescence-based reporter strain CDC1551 (hspX'::GFP), previously small molecule inhibitors of DosRST, HC101A-HC106A were discovered from the whole-cell phenotypic HTS. The characterizations of HC104A and HC106A as DosRST inhibitors are reported herein. Both compounds downregulated genes in the DosR regulon, and inhibited TAG biosynthesis. HC106A also reduced Mtb survival during NPR.

In UV-visible spectroscopy assay, it was observed that HC106A is interacting with the heme of sensor kinase DosS. The UV-vis spectra of HC106A-treated DosS is similar to that of CO- or NO-treated DosS. The overlap between the CO and HC106A spectra supports that HC106A may bind to the heme of DosS similar to CO. Interestingly, CO activates sensor kinases, whereas HC106A inhibits them. This could be due to the difference in conformational changes induced by CO and HC106A, or binding of HC106A may lock the sensor kinases into an inactive state. Furthermore, the mutation G117L on DosS that blocks the channel provides resistance to HC106A. This means that similar to artemisinin, this channel is also important for the activity of HC106A. These findings provide additional evidence that the heme-exposing channel in DosS/T can be exploited by small molecules to prevent or inhibit the heme from sensing signals and to disrupt signal transduction of a two-component regulatory system. These two distinct mechanisms of actions are novel mechanisms to inhibit the pathway.

Mechanistic studies via EMSA support that HC104A may function by targeting DosR and inhibiting DosR DNA binding. Virstatin had no effect on DosR DNA binding and no impact on the DosRST signaling in whole cells, showing that although both compounds share a similar structure, they function by distinct mechanism. From the catalog SAR study, it was found that the bromine group is required for the compound activity because without it the activity was completely abolished. Virstatin does not have the bromine, and the R-group is butyric acid instead of dimethylamine. These two differences are enough to differentiate the compound activity. Moreover, the transcriptional profiling shows that the most repressed genes by HC104A are from DosR regulon, providing another evident that HC104A is specific to DosR. Interestingly, the most genes downregulated by HC104A, including hspX, Rv2030c, pfkB, and Rv2028c, are from the same operon under control of hspX promoter, which is strongly induced by DosR in hypoxia. This suggests that HC104A is more specific to target hspX operon genes compared to other DosR regulated genes. This leads to the speculation that HC104A may be more efficient to prevent DosR binding to the hspX promoter than the other DosR promoters. HC104A may fit better in the pocket in the interface of DosR-hspX' complex. This postulation also supports that HC104A may not impact on DosR protein dimerization, which would lead to universal downregulation of DosR-regulated genes. However, the detailed characterization of HC104A on inhibiting DosR dimerization needs further investigation.

This study together with the previous report reveals multiple distinct inhibitory mechanisms the five compounds, HC101A-104A, HC106A. Four out five compounds, HC101A-HC103A and HC106A, are proposed to function by targeting the sensor kinases DosRST. Furthermore, these four compounds are effective to decrease Mtb survival during NRP in hypoxic-shift down assay. In contrast, the compound targeting DosR, HC104A, had no impact on Mtb survival. This result is consisted with what was previously reported that only ΔdosS mutant exhibits survival defect in non-human primate model. Alternatively, HC104A only inhibits a portion of the DosR regulon, 26 genes. This finding suggests that the DosR regulated genes that are inhibited by HC104A (FIG. 2) are not required for persistence.

This observation further leads us to hypothesize that DosS/T may have DosR independent targets. Several recent studies have demonstrated occurrence of cross-interactions between histidine kinases and response regulators in Mtb. For instance, Lee et al shows that DosT can interact with the other non-cognate response regulators, including NarL and PrrA. The transcriptional profiling shows there are some genes downregulated by HC101A, HC103A and HC106A are DosR-independent (FIG. 2). Six genes are overlapped between artemisinin and HC103A, including Rv0260c that encodes a putative response regulator. HC106A shares 4 off-targeted genes, involved in arginine biosynthesis, with HC103A. Additionally, several transcriptional or response regulators are downregulated by HC101 and HC106A, such as Rv3246, Rv3648c, Rv3855 were repressed by HC101A (>2×, c<0.05), and Rv0081 and Rv0232 were repressed by HC106A. The data presented here and in the literature point to the possibility that DosST modulate gene expression independently of DosR.

The synergy studies generally show significant synergistic interactions between artemisinin and HC102A, HC103A, HC104, or HC106A among all drug combinations. Moreover, artemisinin had a greater synergism with HC102A, HC103A or HC106A compared to HC104A, supporting that inhibition of histidine kinases by second inhibitor can lead to synergistic inhibition of the DosRST pathway. This could be due to both sensor kinases are required for full induction of DosR regulon, where DosT responses early during hypoxia and DosS further induces the regulon in later time, and it is not efficiently to fully inhibit both DosS and DosT with one inhibitor. For instance, artemisinin shows maximum inhibition of hspX and tgs1 by 51- and 166-fold, respectively. The second inhibitor that has a different mechanism may cause completely blocking the sensors from sensing and transducing the signaling. Some compounds may work better to inhibit DosS than DosT, or vice versa. Combination of the two leads to synergistic inhibition of DosST, thus DosRST signaling. Furthermore, artemisinin shows the greatest synergism with HC106A. Both compounds are targeting to the heme of DosS/T through different mechanisms. This suggests that both compounds are not competitor. Both inhibitors can enter the channel of DosST to interact with the heme. Binding of one compound may enhance binding of second compound in a cooperative manner. For instance, binding of HC106A enhances artemisinin to modulate redox status of the heme and facility the alkylation of the heme. In term of mechanism of action, several possibilities could happen if both molecules enter the channel: 1) under the reducing condition, reduced iron of the heme first activates artemisinin to alkylate, then HC106A comes to bind to the iron. The heme-binding pocket may be big enough to contain additional two small molecules. Attaching of two molecules can completely lock DosST in an inactive form; 2) However, if the pocket is small, one molecule could enter the channel and successfully interact with the heme, while the other molecule is being stock in the channel, so the proteins are completely dead. However, the detail biochemical assays are required to determine the interactions between drugs and the proteins.

The identification of new antibacterial agents and tuberculosis drugs has been associated with the realization that these compounds can occupy a different region of chemical space relative to drugs in most other therapeutic areas. Series HC106 is easily in the range of the characteristics for compounds currently in use, in development and anti-TB compounds. Series HC104 needs further exploration to fully assess its suitability. The physicochemical properties of a drug, such as solubility and permeability, impact its oral bioavailability as these factors influence absorption, distribution, metabolism, and excretion. Series HC106 demonstrates reasonably good solubility (Table 5), with compounds generally having kinetic solubility >100 µM). The melting points of most of the compounds in the series and the corresponding c Log P are also supportive. The ability of an anti-TB drug to reach its target site is greatly hampered by the highly impermeable Mtb cell envelope. Both series (HC104 and HC106) demonstrate excellent whole cell $EC_{50}$ values suggesting adequate cell wall permeability.

Example 8: General Experimental Methods

Bacterial strains and growth conditions. Mtb CDC1551, CDC1551 (ΔdosR) strains were used in this study. All cultures were grown at 37° C. and 5% $CO_2$ in 7H9 Middlebrook medium supplemented with 10% OADC and 0.05% Tween-80 in standing, vented tissue culture flasks, unless stated otherwise.

$EC_{50}$ assays. The assay was performed as previously described. Briefly, CDC1551 (hspX'::GFP) reporter strain culture was diluted to an $OD_{600}$ of 0.05 in fresh 7H9 media, pH7.0, and 200 µL of diluted culture was aliquoted in clear-bottom, black, 96-well plates (Corning). Cells were treated with 8-point (2.5-fold) dilution series ranging from 200 µM-0.32 µM. For the structure relationship studies for HC106 series, 12-point (2.5-fold) dilution series of HC106 analogs ranging from 200 µM-8.4 nM were used. GFP fluorescence and optimal growth were measured following 6 d incubation. Percentage of fluorescence and growth inhibitions were normalized to a rifampin-positive control and DMSO-negative control. $EC_{50}$ values were calculated for each compound using GraphPad Prism software package (version 6). Each experiment was performed two technical replicates per plate and two biological replicates, and the error bar represents the s.d. of the biological replicates. Experiments were performed twice with similar results.

Transcriptional profiling and data analysis. Transcriptional profiling studies were conducted as previously described in Zheng et al. Briefly, CDC1551 or CDC1551 (ΔdosR) cultures were treated with 40 µM HC104A, HC106A or DMSO control for 6 d. The starting $OD_{600}$ was 0.1 in 8 mL of 7H9 medium in standing T25 vented tissue culture flasks. The total bacterial RNA from two biological replicates was isolated and prepared for sequencing as previously described. The RNA-seq data was processed and analyzed using the SPARTA software package.

Real time-PCR assays. The vitamin C and NO assays were performed as previously described. Briefly, cultures at an $OD_{600}$ of 0.6 were pretreated with 80 µM HC104A, HC106A or a DMSO control for 24 h, and induced with 50 µM DETA-NONOate or 20 mM vitamin C for 2 h. For the HC106A resistance assays, CDC1551 was transformed with the empty replicating pVV16 or the plasmid expressing dosS from the strong hsp60 promoter (pVV16-DosS), and treated with 20 µM HC106A for 6 d. Total bacterial RNA was isolated and differential gene expression of DosR-regulated genes, including hspX and tgs1, was quantified in semiquantitative RT-PCR. The experiment was performed in three technical replicates and error bars represent the s.d from the mean. The experiment was repeated twice with similar results.

Transcriptional profiling in macrophages. Murine bonemarrow derived macrophages were isolated as previously described and seeded in T75 vented, tissue culture flasks. Macrophages were infected with CDC1551 with MOI ratio of 1:20 as previously described. After infection, the flasks were treated with 40 µM HC104A or HC106A or DMSO for 48 h, with three individual flasks for each treatment. Total bacterial RNA was isolated after treatment, and the transcripts of DosR-controlled genes (hspX and tgs1) were quantified in RT-PCR. The experiment was conducted with three biological replicates. The error bar represents the s.d. of the biological replicates.

Triacylglycerol biosynthesis. The lipid labelling and TAG TLCs were performed as previously. Briefly, CDC1551 was cultured at an initial $OD_{600}$ of 0.1 and radiolabeled with 8 µCi of $[1,2-^{14}C]$ sodium acetate in T25 vented tissue culture flasks. The cultures were treated with 40 µM HC104A, HC106A or DMSO for 6 d at 37° C. CDC1551 (ΔdosR) and dosRS complement strains were also examined. Total lipids were extracted and $^{14}C$ incorporation was determined by scintillation counting. 20,000 c.p.m. of total lipids were analyzed by thin-layer chromatography (TLC) using silica gel 60 aluminum sheets (EMD Millipore). To determine triacylglycerol (TAG) accumulation, the lipids were developed in hexane-diethyl ether-acetic acid (80:20:1; vol/vol/vol) solvent system. The TLC was exposed to a phosphor screen for 3 d, and imaged on a Typhoon imager and TAG was quantified using ImageJ software. The experiment was repeated twice with similar results, and the error bar represents the s.d. of two biological replicates.

NRP survival assays. Survival during NRP was examined using the hypoxic shift down assays as previously described. Briefly, CDC1551 cells were treated with 40 µM HC104A, HC106A or DMSO control in a 24-well plate (1 mL/well). CDC1551 (ΔdosR) and dosRS complement strains were also examined. Plates were incubated in an anaerobic chamber (BD GasPak) for 12 d. It took 48 h for culture to become anaerobic, as monitored by a methylene blue control. The bacterial CFUs were numerated on 7H10 agar plates following incubation. The experiment was repeated twice with similar results.

DosR protein purification. DosR full length protein was purified as previously described. Briefly, the dosR gene (Rv3133c) was cloned into pET15b (Novagen Darmstadt, Germany) using the primer set (forward primer TTT-CATATGGTGGTAAAGGTCTTCTTGGTCGATGAC; reverse primer TTTGGATCCTCATGGTCCAT-CACCGGGTGG). The $His_6$-DosR protein was expressed in E. coli BL21(DE3) strain. The culture was grown to $OD_{600}$ 0.5-06, and induced with 1 mM IPTG for 6.5 h at 29° C. The cell pellet was suspended in lysis buffer (20 mM Tris-HCl, pH 8.0, 10% glycerol, 500 mM NaCl, 0.5 mg/ml lysozyme and 0.1 mg/ml PMSF), and incubated at 37° C. for 30 min. The soluble fraction of lysate was collected after centrifugation and applied to a TALON metal affinity $Co^{2+}$ column (Clontech). The column was washed twice with washing buffer (20 mM Tris-HCl, pH 8.0, 10% glycerol, 500 mM NaCl) without imidazole, then with 20 mM imidazole. The protein was eluted with the same buffer containing 300 mM imidazole. The fractions with the most DosR protein (as determined by SDS-PAGE) were pooled together for dialysis in 25 mM Tris-HCl, pH 8.0. The final protein concentration was determined using a Qubit kit (Invitrogen).

Electrophoretic mobility assay (EMSA). The assay is florescence-based using 6-carboxyfluorescein (6FAM) labeled 385 bp probe from the hspX promoter. In designing the primer set, 6FAM was added to the 5' ends of forward and reverse primers. The hspX probe was synthesized via PCR using the primer set (forward primer 6FAM-CAACTGCACCGCGCTCTTGATG; reverse primer 6FAM-CATCTCGTCTTCCAGCCGCATCAAC). The probe was purified by Qiagen PCR purification kit. The DosR protein was pre-phosphorylated in a 10 µL of phosphorylation buffer (40 mM Tris-HCl, pH 8.0, 5 mM $MgCl_2$, 50 mM lithium potassium acetyl phosphate), and incubated at RT for 30 min. The protein was then transferred to binding buffer to the final volume of 20 µL (final concentration, 25 mM Tris-HCl, pH 8.0, 0.5 mM EDTA, 20 mM KCl, 6 mM MgCl2, 10 nM probe, 1 µg poly-dI-dC (Sigma Aldrich)), and treated with HC104A or equal volume of DMSO or virstatin (Santa Cruz Biotech.). Two different assays were performed. Firstly, different DosR protein concentrations from 0.5 µM to 4 µM were treated with 40 µM to determine which concentration of DosR that HC104A had impact on. Then the close response assays were performed with 2 µM DosR treated with different concentrations of HC104A or virstatin from 1 µM to 80 µM. After incubating on ice for 30 min, the reaction was terminated by adding 1 µL 80% glycerol, and loaded on the native 5% TBE polyacrylamide gel. The gel was run at 50V, for 5-6 hours at 4° C. in 1×TBE buffer, and was imaged using a Typhoon scanner with appropriate filters that can detect florescence at Ex.=495 nm, Em.=520 nm. Binding of the unbound probe was quantified using ImageJ. The assay was repeated at least twice with similar results. The error bar represents the s.d. of two biological replicates.

UV-visible spectroscopy assay. DosS and mutant proteins were purified and were analyzed as previously described. Briefly, 7.5 µM of recombinant DosS protein was deoxygenated with argon gas in a sealed cuvette. The protein was reduced with 400 µM dithionite (DTN) for 20 min. The reaction was then treated with 100 µM HC106A, 400 µM HC104A, 100 µM tricarbonyldichlororuthenium (II) dimer or equal volume of DMSO. The UV-visible spectra were recorded for kinetic changes over 2 h. The experiment was repeated at least twice with similar results.

Checkboard synergy studies. The reporter strain CDC1551 (hspX: GFP) was treated with two DosRST inhibitors from 50 µM-0.08 µM in 96-well plates, including HC101A-HC104A and HC106A. GFP fluorescence and $OD_{600}$ were measured after 6 d incubation. The percentage of FI and GI were calculated for each drug pair. The FI data was utilized for further analysis in the CompuSyn. The Combination Index (CI) value was calculated for each drug pair according to the Chou-Talalay method, which is based on the Median-Effect equation derived from the Mass-Action Law principle. The resulting CI values provide quantitative determination of drug interactions, including synergism (CI<1), additive effect (C=1), and antagonism (C>1).

Autophosphorylation assay. The DosS autophosphorylation assay was performed as previously described. DosS protein was treated with 10 μM, 20 μM or 40 μM of HC104A, or HC106A. DMSO and 40 μM HC103A were also included as positive and negative controls, respectively.

Example 9: Experimental Procedure for Urea Formation

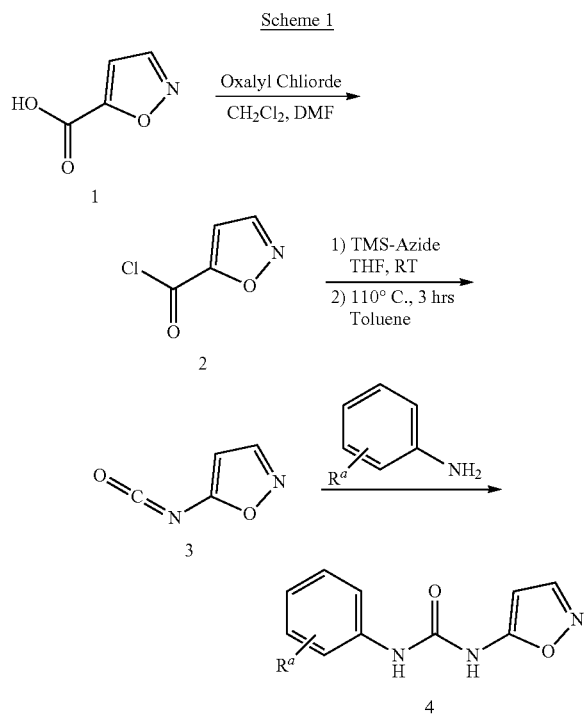

Scheme 1

Formation of acyl chloride 2. To a stirred solution of isoxazole acid 1 (1 eq.) in dry THF (0.4 M) under $N_2$ atmosphere was added oxalyl chloride (1.5 eq.) dropwise over 5-10 minutes followed by DMF (cat.) and the reaction mixture was continued to stir at r.t. Upon completion, the reaction mixture was concentrated into a residue in vacuo and the residue was dissolved in THF and concentrated again to ensure the removal of excess oxalyl chloride. The crude acyl chloride 2 was used directly in the next step without further purification.

Formation of acyl azide and rearrangement into isocyanate 3. The crude acyl chloride 2 was dissolved in THF (0.4 M) and stirred at r.t. under $N_2$ atmosphere. $TMSN_3$ (2 eq.) was added dropwise over 5 minutes and stirring was continued for two hours. Upon completion, the reaction mixture was diluted with EtOAc (0.4 M) and quenched with $H_2O$ (0.4 M). The two layers were separated, and the organic layer was dried over anhydrous $Na_2SO_4$ and filtered. The EtOAc solvent was swapped into Toluene (0.1 M) by the addition of toluene followed by removal of the ethyl acetate in vacuo. Care was taken not to concentrate the toluene. The toluene acyl azide solution was heated at reflux conditions under $N_2$ atmosphere for 4 h to give the desired isocyanate 3 which was used as a solution in toluene in the next step without further purification.

Formation of urea 4. The crude isocyanate solution in toluene was mixed with different amines (1.5 eq.) and stirred at r.t. for overnight. Isolation of the ureas was done by diluting the reaction mixture with hexanes and stirring for few hours and filtration of the formed precipitate. The solid material was washed with hexanes and dried under high vacuum. The urea products usually do not require further purifications. All products were analyzed by $^1H$ NMR and high-resolution mass spectrometry.

Synthesis of MSU-41422 (Amide) from acyl chloride 2. Acyl chloride 2 (1 eq.) was dissolved in DCM (0.2 M) and 4-chloroaniline (1.2 eq.) was added. The reaction mixture was stirred at r.t. for overnight. The reaction mixture was concentrated in vacuo and the residue was purified by flash column chromatography.

Synthesis of MSU-39449. A slurry of 4-chlorophenyl acetic acid (0.10 g, 0.60 mmoles) in 2.0 mL of dichloromethane was treated with oxalyl chloride (0.12 mL, 0.9 mmoles) and 1 drop of dimethylformamide. The mixture (with gas evolution) gradually became homogeneous and was stirred for 30 minutes. The mixture was concentrated in vacuo, diluted with 5 mL of dichloromethane and again concentrated in vacuo, the process repeated three times. The resulting residue was again dissolved in dichloromethane (2 mL) and treated with 5-aminoisoxazole (0.030 g., 0.36 mmoles), followed by pyridine (0.48 mL, 0.6 mmoles). The mixture was then allowed to stir overnight. The mixture was then quenched with 1.0 N HCl and extracted with dichloromethane. The organic layers were combined, washed with saturated $KHCO_3$, dried with $Na_2SO_4$ and concentrated in vacuo. MPLC chromatography ($SiO_2$, 100% dichloromethane to 3% methanol/dichloromethane) to provide a solid (0.023 g).

1,3-bis(1,2-oxazol-5-yl)urea (MSU-39444). $^1H$ NMR (500 MHz, DMSO-$d_6$) δ 10.54 (s, 2H), 8.44 (d, J=1.9 Hz, 2H), 6.11 (d, J=2.0 Hz, 2H). HRMS (ESI) m/z calculated for $C_7H_6N_4O_3$ [M+H], 195.0513 found 195.0518.

(2-(4-chlorophenyl)-N-(1,2-oxazol-5-yl)acetamide (MSU-39449). $^1H$ NMR (500 MHz, DMSO-$d_6$) δ 11.91 (s, 1H), 8.41 (s, 1H), 7.39 (d, J=2.0 Hz, 2H), 7.35 (d, J=2.0 Hz, 2H), 6.19 (s, 1H), 3.73 (s, 2H). HRMS (ESI) m/z calculated for $C_{11}H_{10}ClN_2O_2$ [M−H], 235.0269; found 235.1989.

1-(3-chlorophenyl)-3-(1,2-oxazol-5-yl)urea (MSU-39445). $^1H$-NMR (500 MHz, DMSO-$d_6$) δ 10.41 (s, 1H), 9.14 (s, 1H), 8.40 (d, J=2.0 Hz, 1H), 7.82-7.58 (m, 1H), 7.31 (dd, J=4.9, 1.8 Hz, 2H), 7.07 (dt, J=6.4, 2.3 Hz, 1H), 6.06 (d, J=1.9 Hz, 1H). HRMS (ESI) m/z calculated for $C_{10}H_9ClN_3O_2$[M+H], 238.0378; found 238.0365.

1-(3,4-dichlorophenyl)-3-(1,2-oxazol-5-yl)urea (MSU-39452). $^1H$ NMR (500 MHz, DMSO-$d_6$) δ 10.50 (s, 1H), 9.23 (s, 1H), 8.51-8.28 (m, 1H), 7.86 (d, J 2.5 Hz, 1H), 7.64-7.43 (m, 1H), 7.37 (dd, J=8.9, 2.5 Hz, 1H), 6.26-5.80 (m, 1H). HRMS (ESI) m/z calculated for $C_{10}H_8Cl_2N_3O_2$ [M+H], 271.9989; found 271.9969.

1-(4-methoxyphenyl)-3-(1,2-oxazol-5-yl)urea (MSU-39447). $^1H$ NMR (500 MHz, DMSO-$d_6$) δ 8.83 (s, 1H), 8.43-8.29 (m, 1H), 7.36 (d, J=8.4 Hz, 2H), 6.86 (d, J=8.6 Hz, 2H), 6.00 (d, J=1.9 Hz, 1H), 3.70 (s, 3H). HRMS (ESI) m/z calculated for $C_{11}H_{12}N_3O_3$ [M+H], 234.0874; found 234.0863.

1-(4-chlorophenyl)-1-methyl-3-(1,2-oxazol-5-yl)urea (MSU-39451). $^1$H NMR (500 MHz, DMSO-$d_6$) δ 10.13 (s, 1H), 8.34 (d, J=1.9 Hz, 1H), 7.56-7.41 (m, 2H), 7.41-7.22 (m, 2H), 6.04 (d, J=2.0 Hz, 1H), 3.25 (s, 3H). HRMS (ESI) m/z calculated for $C_{11}H_{11}ClN_3O_2$[M+H], 252.0535; found 252.0596.

5-chloro-N-(1,2-oxazol-5-yl)-2,3-dihydro-1H-indole-1-carboxamide (MSU-39453). $^1$H NMR (500 MHz, DMSO-$d_6$) δ 10.49 (s, 1H), 8.41 (d, J=1.9 Hz, 1H), 7.84 (d, J=8.7 Hz, 1H), 7.27 (dt, J=2.3, 1.1 Hz, 11H), 7.18 (dt, J=8.8, 1.6 Hz, 1H), 6.14 (d, J=1.9 Hz, 1H), 4.13 (dd, J=9.1, 8.2 Hz, 2H), 3.17 (t, J=8.6 Hz, 2H). HRMS (ESI) m/z calculated for $C_{12}H_{11}ClN_3O_2$[M+H], 264.0535; found 264.0552.

1-(6-chloropyridin-3-yl)-3-(1,2-oxazol-5-yl)urea (MSU-39448). $^1$H NMR (500 MHz, DMSO-$d_6$) δ 10.55 (s, 11H), 9.25 (s, 1H), 8.64-8.24 (m, 2H), 7.98 (d, J=8.6 Hz, 1H), 7.45 (d, J=8.6 Hz, 1H), 6.08 (d, J=18.1 Hz, 1H). HRMS (ESI) m/z calculated for $C_9H_8ClN_4O_2$[M+H], 239.0331; found 239.0364.

1-(5-chloropyridin-2-yl)-3-(1,2-oxazol-5-yl)urea (MSU-39450). $^1$H NMR (500 MHz, DMSO-$d_6$) δ 11.00 (s, 1H), 9.66 (s, 1H), 8.42 (d, J=1.9 Hz, 1H), 8.34 (d, J=2.6 Hz, 1H), 7.96-7.79 (m, 1H), 7.73 (d, J=8.9 Hz, 1H), 6.10 (q, J=2.7, 2.2 Hz, 211). HRMS (ESI) m/z calculated for $C_9H_8ClN_4O_2$[M+H], 239.0331; found 239.0356.

1-(5-fluoropyridin-2-yl)-3-(1,2-oxazol-5-yl)urea (MSU-39446). $^1$H NMR (500 MHz, DMSO-$d_6$) δ 10.24 (s, 1H), 8.90 (s, 1H), 8.38 (d, J=1.9 Hz, 1H), 7.54-7.37 (m, 2H), 7.26-7.02 (m, 2H), 6.03 (d, J=2.0 Hz, 1H). HRMS (ESI) m/z calculated for $C_{10}H_9FN_3O_2$[M+H], 222.0674; found 222.0675).

(MSU-41422). $^1$H NMR (500 MHz, Chloroform-d) δ 8.41 (d, J=1.8 Hz, 1H), 8.26 (s, 1H), 7.71-7.52 (m, 211), 7.44-7.33 (m, 2H), 7.06 (d, J=1.8 Hz, 1H). HRMS (ESI) m/z calculated for $C_{10}H_8ClN_2O_2$[M+H], 223.0269; found 223.0265.

3-(5-chloropyridin-2-yl)-1-(4-methylphenyl)urea (MSU-41324). $^1$H NMR (500 MHz, DMSO-$d_6$) δ 9.91 (s, 11H), 9.50 (s, 1H), 8.31 (d, J=2.6 Hz, 11H), 7.85 (dd, J=9.0, 2.7 Hz, 11H), 7.67 (d, J=8.9 Hz, 1H), 7.39-7.30 (m, 2H). HRMS (ESI) m/z calculated for $C_{12}H_{10}Cl_2N_3O$ [M+H], 282.0196; found 282.0182.

MSU-41425. $^1$H NMR (500 MHz, DMSO-$d_6$) δ 8.83 (s, 1H), 7.53-7.39 (m, 2H), 7.39-7.16 (m, 2H).

1-{[1,1'-biphenyl]-4-yl}-3-(1,2-oxazol-5-yl)urea (MSU-41443). $^1$H NMR (500 MHz, DMSO-$d_6$) δ 10.36 (d, J=28.4 Hz, 1H), 9.13 (d, J=45.7 Hz, 1H), 8.40 (d, J=1.9 Hz, 1H), 7.70-7.59 (m, 5H), 7.59-7.49 (m, 3H), 7.43 (t, J=7.7 Hz, 3H), 7.32 (t, J=7.4 Hz, 3H), 6.06 (d, J=1.9 Hz, 1H). HRMS (ESI) m/z calculated for $C_{16}H_{14}N_3O_2$ [M+H], 280.1081; found 280.1083.

1-(4-tert-butylphenyl)-3-(1,2-oxazol-5-yl)urea (MSU-41442). $^1$H NMR (500 MHz, DMSO-$d_6$) δ 10.15 (s, 1H), 8.77 (s, 1H), 8.38 (d, J=1.9 Hz, 1H), 7.44-7.27 (m, 4H), 6.03 (d, J=2.0 Hz, 1H), 1.25 (s, 9H). HRMS (ESI) m/z calculated for $C_{14}H_8N_3O_2$[M+H], 260.1394; found 260.1406.

3-(1,2-oxazol-5-yl)-1-phenylurea (MSU-33189). $^1$H NMR (500 MHz, DMSO-$d_6$) δ 10.20 (s, 1H), 8.85 (s, 1H), 8.39 (d, J=1.9 Hz, 1H), 7.54-7.37 (m, 2H), 7.35-7.21 (m, 2H), 7.02 (t, J=7.4 Hz, 1H), 6.04 (d, J=1.9 Hz, 1H). HRMS (ESI) m/z calculated for $C_{10}H_{10}N_3O_2$[M+H], 204.0768; found 204.0777.

1-(4-chlorophenyl)-3-(1,2-oxazol-5-yl)urea (MSU-33231). $^1$H NMR (500 MHz, DMSO-$d_6$) δ 10.29 (s, 1H), 9.01 (s, 1H), 8.39 (d, J=1.9 Hz, 1H), 7.56-7.41 (m, 2H), 7.41-7.27 (m, 2H), 6.05 (d, J=1.9 Hz, 1H). HRMS (ESI) m/z calculated for $C_{10}H_9ClN_3O_2$[M+H], 238.0378; found 238.0391.

1-benzyl-3-(1,2-oxazol-5-yl)urea (MSU-41462). $^1$H NMR (500 MHz, DMSO-$d_6$) δ 10.18 (s, 1H), 8.31 (d, J=2.0 Hz, 1H), 7.43-7.07 (m, 3H), 6.92 (s, 1H), 5.94 (d, J=1.9 Hz, 1H), 4.30 (d, J=6.0 Hz, 2H). HRMS (ESI) m/z calculated for $C_{11}H_{12}N_3O_2$ [M+H], 218.0924 found 218.0956.

3-(1,2-oxazol-5-yl)-1-[4-(trifluoromethyl)phenyl]urea (MSU-41463). $^1$H NMR (500 MHz, DMSO-$d_6$) δ 10.39 (s, 1H), 9.29 (s, 1H), 8.41 (d, J=1.9 Hz, 1H), 7.67 (d, J=1.0 Hz, 4H), 6.08 (d, J=1.9 Hz, 1H). HRMS (ESI) m/z calculated for $C_{11}H_9F_3N_3O_2$ [M+H], 272.0642; found 272.0653.

1-(4-bromophenyl)-3-(1,2-oxazol-5-yl)urea (MSU-41464). $^1$H NMR (500 MHz, DMSO-$d_6$) δ 10.29 (s, 1H), 9.01 (s, 1H), 8.39 (d, J=1.9 Hz, 2H), 7.50-7.45 (m, 1H), 7.45-7.40 (m, 1H), 6.05 (s, 1H). HRMS (ESI) m/z calculated for $C_{10}H_9BrN_3O_2$[M+H], 281.9873; found 281.9876.

methyl 4-{[(1,2-oxazol-5-yl)carbamoyl]amino}benzoate (MSU-41465). $^1$H NMR (500 MHz, DMSO-$d_6$) δ 10.38 (s, 1H), 9.27 (s, 1H), 8.41 (d, J=2.0 Hz, 1H), 8.00-7.79 (m, 2H), 7.66-7.48 (m, 2H), 6.08 (d, J=1.9 Hz, 1H), 3.81 (s, 3H). HRMS (ESI) m/z calculated for $C_{12}H_{12}N_3O_4$ [M+H], 262.0823; found 262.0827.

3-(1,2-oxazol-5-yl)-1-[4-(phenoxymethyl)phenyl]urea (MSU-41545). $^1$H NMR (500 MHz, DMSO-$d_6$) δ 10.17 (s, 1H), 8.71 (s, 1H), 8.37 (d, J=1.9 Hz, 1H), 7.57-7.14 (m, 5H), 7.11-6.69 (m, 2H), 6.02 (d, J=1.9 Hz, 1H), 5.06 (s, 2H). HRMS (ESI) m/z calculated for $C_{17}H_{16}N_3O_3$ [M+H], 310.1187; found 310.1178.

1-cyclopentyl-3-(1,2-oxazol-5-yl)urea (MSU-41546). $^1$H NMR (500 MHz, DMSO-$d_6$) δ 9.69 (s, 1H), 8.30 (d, J=1.9 Hz, 1H), 6.42 (d, J=7.2 Hz, 1H), 5.91 (d, J=1.9 Hz, 1H), 3.92 (h, J=6.7 Hz, 1H), 1.83 (dq, J=12.8, 6.6, 6.0 Hz, 3H), 1.73-1.46 (m, 5H), 1.46-1.13 (m, 3H). HRMS (ESI) m/z calculated for $C_9H_{14}N_3O_2$ [M+H], 196.1081; found 196.1144.

1-cyclohexyl-3-(1,2-oxazol-5-yl)urea (MSU-42002). $^1$H NMR (500 MHz, DMSO-$d_6$) δ 9.80 (s, 1H), 8.30 (d, J=1.9 Hz, 1H), 6.34 (d, J=7.8 Hz, 1H), 5.90 (d, J=1.9 Hz, 1H), 3.58-3.39 (m, 1H), 1.77 (dt, J=11.1, 3.7 Hz, 1H), 1.64 (dt, J=12.9, 4.1 Hz, 1H), 1.52 (dd, J=10.4, 6.3 Hz, 1H), 1.37-0.93 (m, 3H). HRMS (ESI) m/z calculated for $C_{10}H_{16}N_3O_2$ [M+H], 210.1238; found 210.1282.

3-(1,2-oxazol-5-yl)-1-(2-phenylethyl)urea (MSU-42004). $^1$H NMR (500 MHz, DMSO-$d_6$) δ 10.07 (s, 2H), 8.31 (d, J=2.0 Hz, 1H), 7.37-7.06 (m, 5H), 6.40 (s, 1H), 5.93 (d, J=1.8 Hz, 1H), 3.31 (t, J=7.2 Hz, 2H), 2.74 (t, J=7.2 Hz, 2H). HRMS (ESI) m/z calculated for $C_{12}H_{14}N_3O_2$ [M+H], 232.1081; found 232.1105.

1-(3-bromophenyl)-3-(1,2-oxazol-5-yl)urea (MSU-42003). $^1$H NMR (500 MHz, DMSO-$d_6$) δ 10.36 (s, 1H), 9.06 (s, 1H), 8.40 (d, J=1.9 Hz, 1H), 7.83 (t, J=2.0 Hz, 1H), 7.46-7.03 (m, 3H), 6.07 (d, J=2.0 Hz, 1H). HRMS (ESI) m/z calculated for $C_{10}H_9BrN_3O_2$[M+H], 281.9873; found 281.9915.

3-(2-methylpropyl)-1-(1,2-oxazol-5-yl)urea (MSU-41542). $^1$H NMR (500 MHz, DMSO-$d_6$) δ 10.20-9.49 (m, 1H), 8.30 (d, J=1.9 Hz, 1H), 6.44 (t, J=5.9 Hz, 1H), 5.91 (d, J=1.9 Hz, 1H), 2.93 (t, J=6.3 Hz, 2H), 1.68 (dh, J=13.3, 6.7 Hz, 1H), 0.85 (d, J=6.7 Hz, 6H). HRMS (ESI) m/z calculated for $C_8H_{14}N_3O_2$ [M+Na], 206.0899; found 206.0926.

Example 10: Quantitative Single-Cell Imaging of Mtb in Host Tissues

Figure 15:
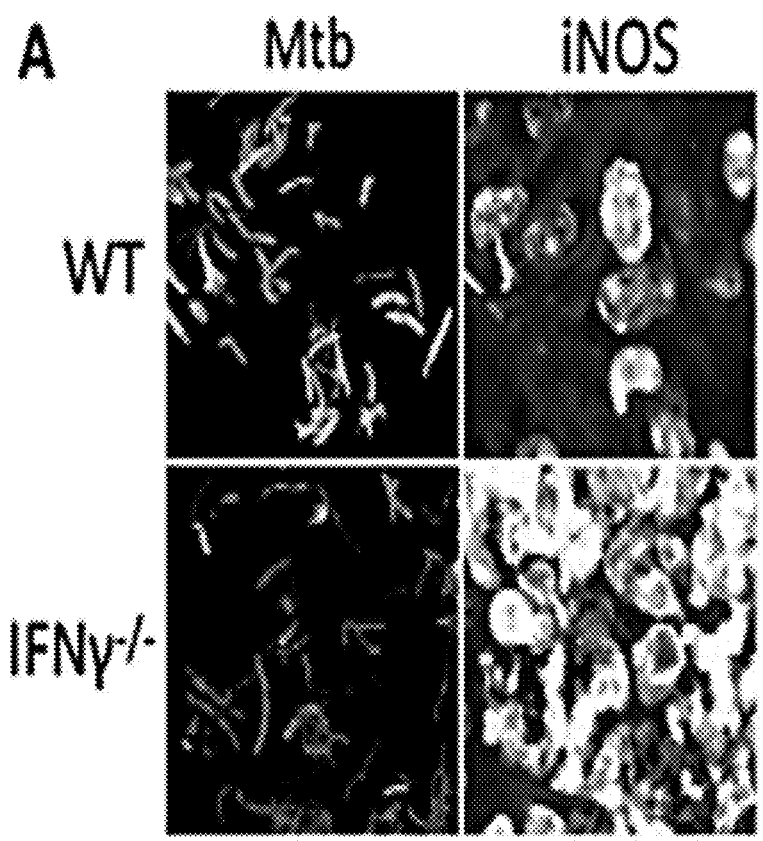
FIG. 15 has three parts, A-C, and shows (A) Mtb hspX':: GFP biosensor GFP fluorescence is more strongly induced in the lungs of WT C57Bl/6J mice as compared to IFNγ$^{-/-}$ mice 28 dpi (left panels). Antibody staining against iNOS (in blue) demonstrates biosensor GFP fluorescence is associated with the presence of iNOS (right panels). (B) Quantification of single cell gene expression in intact lung tissue demonstrates biosensor GFP fluorescence is induced over time and requires IFNγ. (C) Quantification of single cell gene expression demonstrates an association between GFP fluorescence and the presence of iNOS, consistent with the biosensor being regulated by NO.
Figure 15:
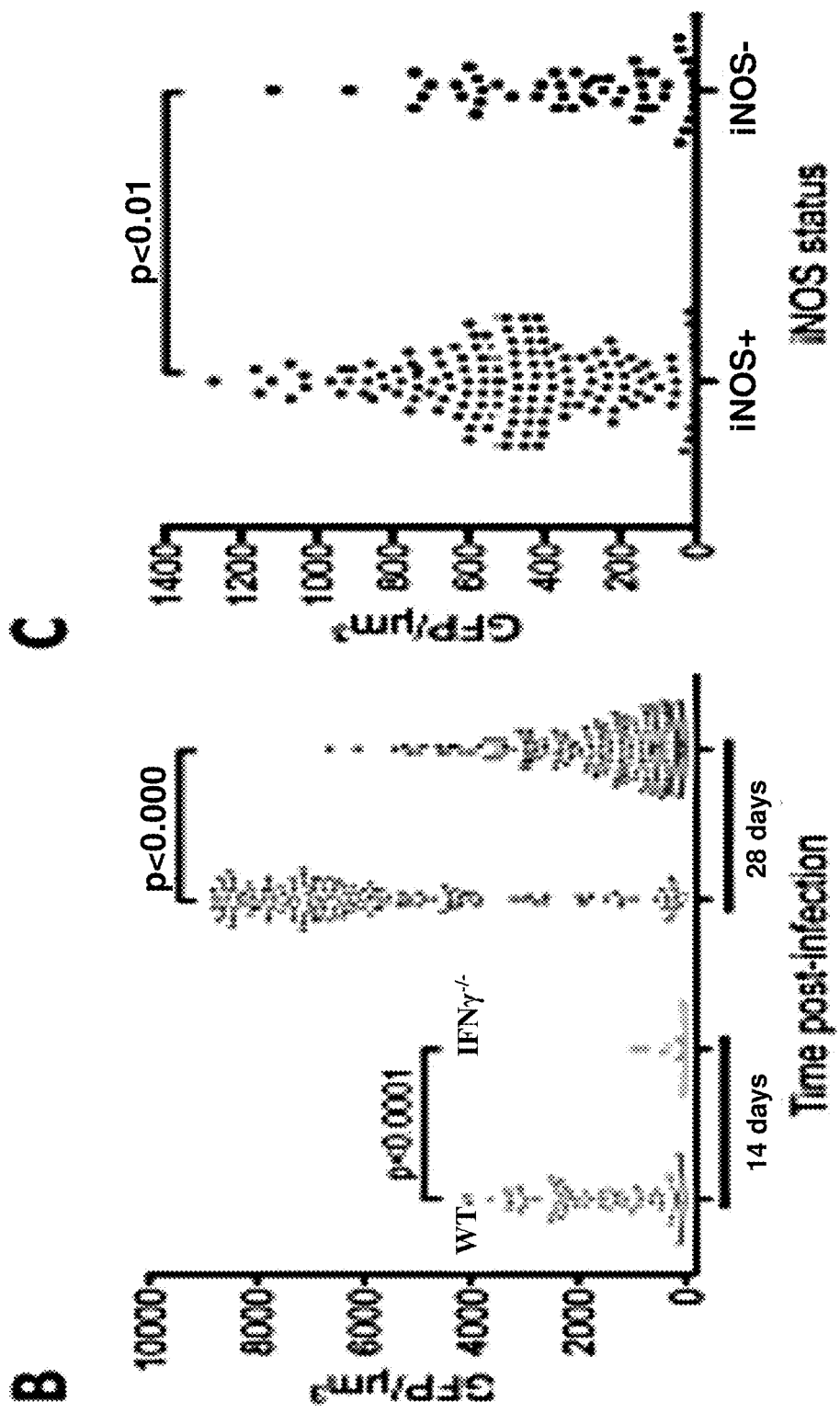

Gene expression studies have shown that DosRST-regulated genes are induced in vivo. However, in vivo, Mtb will encounter a spectrum of environments and immune pressures, that elicit microenvironment-induced alterations of its gene expression. Therefore, traditional in vivo gene expression analyses cannot detect the natural heterogeneity of gene expression within Mtb subpopulations. To address this barrier, the combined use of confocal microscopy, reporter strains and digital image analysis to permit quantitative analysis of single-cell, microenvironment-specific Mtb gene expression in vivo was established. C57Bl/6J wild type (WT) or interferon-$\gamma^{-/-}$ (IFN$\gamma^{-/-}$) mice were infected with the Mtb hspX'::GFP biosensor. This biosensor also carries a constitutively expressed mCherry construct (driven by the smyc$^1$ promoter) to enable normalization of GFP induction. Fourteen and 28 days post infection (dpi), lung tissue was harvested, sectioned and examined by confocal microscopy. Strong induction of GFP fluorescence was observed in WT infected mice (FIG. 15, Part A) that increased as disease progressed (FIG. 15, Part B). Notably, in IFNγ−/− mice with a compromised immune response, biosensor fluorescence was not induced as strongly. Using Volocity software (Perkin Elmer), biosensor induction was quantified and it was observed a significant increase of biosensor fluorescence over time in WT mice and significant difference in biosensor fluorescence between WT and IFNγ$^{-/-}$ mice (FIG. 15, Part B). To begin characterizing the nature of this difference, inducible nitric oxide synthase (iNOS) was stained and statistically significant association between biosensor fluorescence and presence of iNOS was observed (FIG. 15, Part A and 15, Part C). These data demonstrate the feasibility of employing the quantitative in vivo imaging studies.

Example 11: HC104A and HC106A Inhibit DosRST Regulated Genes

Figure 16:
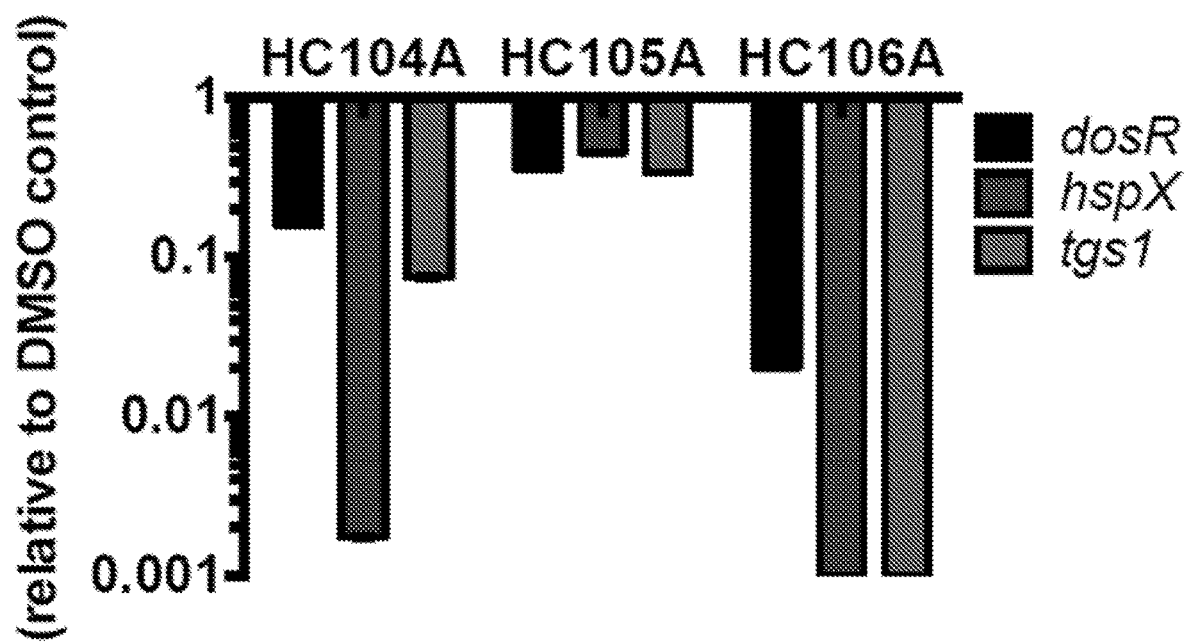
FIG. 16 shows real-time PCR shows inhibition of DosR regulated genes during hypoxia in Mtb treated with 10 μM of the compounds.
Figure 17:
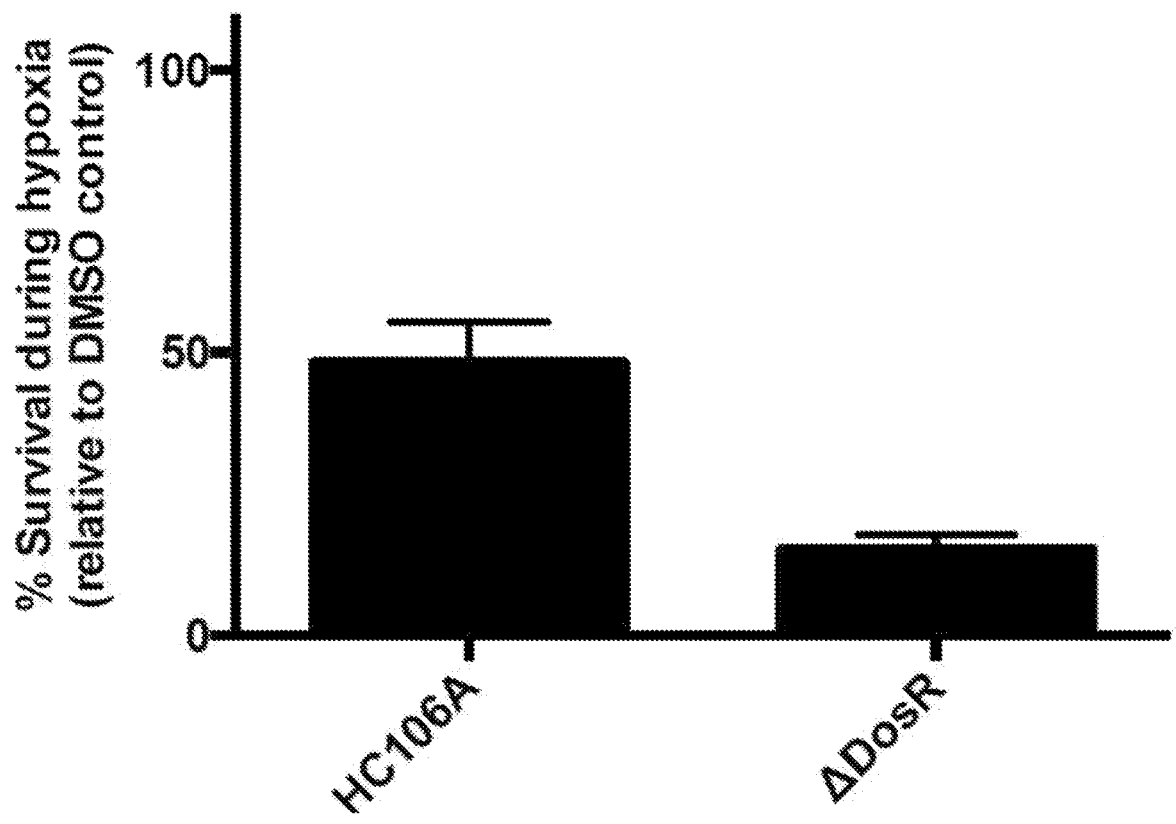
FIG. 17 shows that during hypoxia, treatment with HC106A reduces survival by 50% as compared to a DMSO control. As a control, the dosR mutant control has 80% reduction of survival.

Characterization of additional novel inhibitors of the DosRST pathway HC104A, HC105A and HC106A was carried out. To confirm these compounds inhibit the DosRST pathway, the inhibition DosR regulon genes during hypoxia was examined. HC104A and H106A strongly inhibited hspX and tgs1 gene expression (FIG. 16). Indeed, hspX and tgs1 were repressed to undetectable levels in HC106A treated cells. Based on these data, HC104 and HC106 was prioritized for further study. An initial characterization of HC106A in the hypoxic shift-down model of NRP showed that it reduced survival by 50% relative to a DMSO control (FIG. 17), consistent with the activity observed with the well characterized compounds HC101, HC102, and HC103. Full characterization of HC104 and HC016 inhibition of survival during the hypoxic shift down assay will be examined.

Example 12: HC104A Inhibits DosR DNA-Binding

Figure 18:
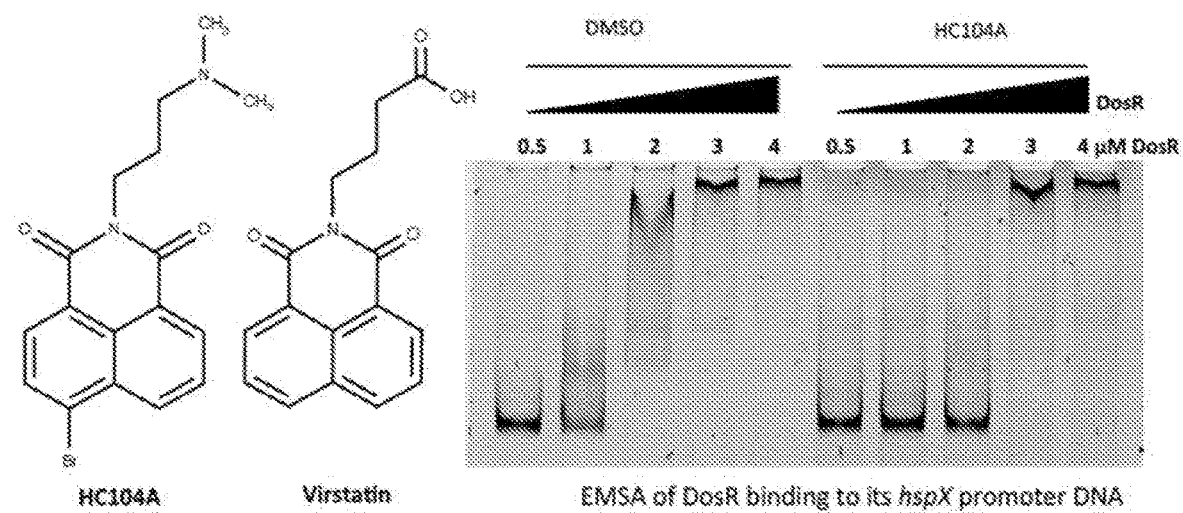
FIG. 18 shows that HC1104A inhibits DosR binding to promoter DNA. HC104A shares a similar scaffold to Virstatin, a known inhibitor of transcription factor dimerization and DNA binding. Inhibition of DosR binding of hspX promoter DNA in the presence of 40 μM HC104A was examined. Inhibition compared to the DMSO control, is observed when 1 and 2 μM of DosR protein is used in the assay. The $IC_{50}$ for inhibition of DosR-DNA binding is ~10 μM (data not shown).

The characterization of artemisinin, HC102A and HC103A showed that the sensor kinase heme or kinase autophosphorylation were vulnerable targets for chemical inhibition of the DosR pathway. HC104A was examined for modulation of heme redox or kinase autophosphorylation activity, inhibitory activity was not observed. This finding suggests HC104A was targeting another aspect of DosRST signaling. Notably, HC104A bears similarity to the compound Virstatin (FIG. 18), which has been shown to interfere with the dimerization of the ToxT transcription factor in *Vibrio cholera*. Therefore, it was hypothesized that HC104A may be functioning by interfering with the dimerization of the response regulator transcription factor DosR and its binding to DNA. A electrophoretic mobility shift assays (EMSA) was conducted with DosR to examine the impact of HC104A on binding of the hspX promoter region DNA. In preliminary results, it was observed that HC104A inhibits the ability of DosR to bind DNA (FIG. 18) and functions with an IC$_{50}$ of ~10 μM (data not shown). Notably, Virstatin did not impact DosR binding of promoter DNA, nor did virstatin inhibit the DosRST pathway in the whole cell Mtb assay (data not shown). These data suggest that HC104A is acting by a novel mechanism, possibly by targeting DosR, although additional experiments need to be undertaken to support this conclusion.

Example 13: HC106A Modulates DosS Heme Via a New Mechanism

Figure 19:
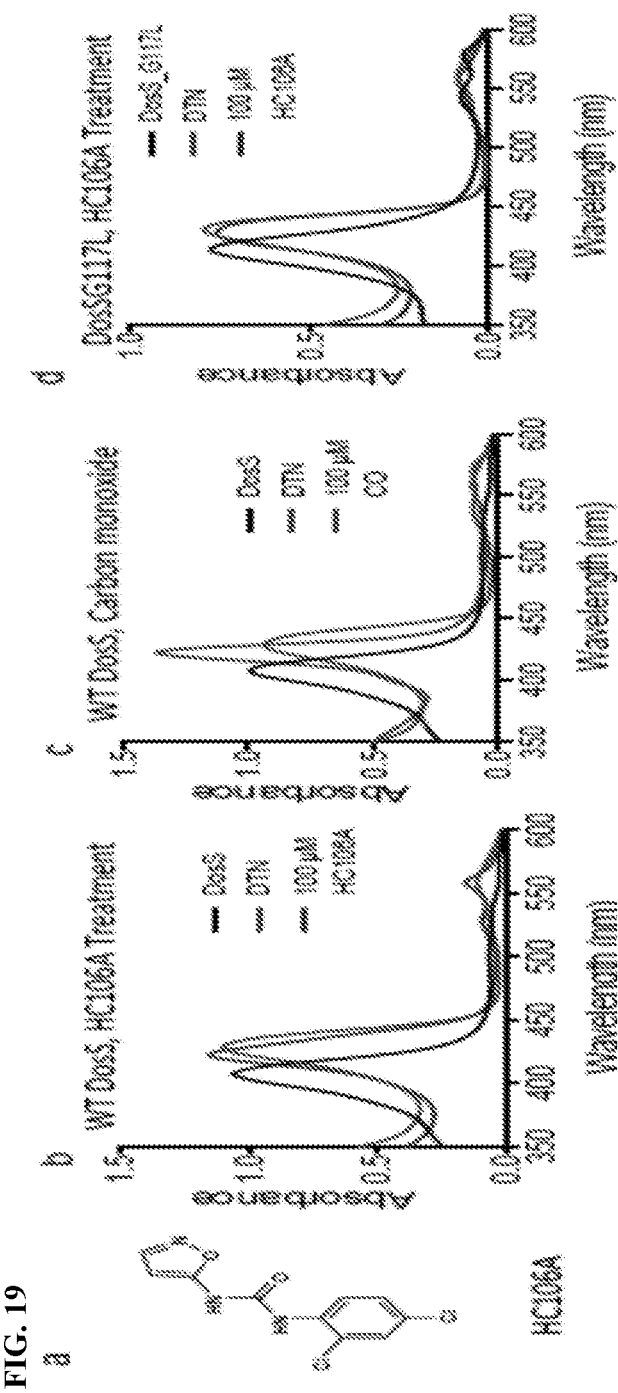
FIG. 19 has four parts, and shows that HC106A modulates DosS heme redox similarly to nitric oxide carbon monoxide. (A) HC106A structure. (B-D). UV-visible spectra of DosS treated with HC106A (B), carbon monoxide (C) or the DosS (G117L) substituted protein treated with HC106A (C).
Figure 19:

HC106A (FIG. 19, Part A) was tested for its ability to modulate DosS heme redox status using a UV-visible spectroscopy assay. HC106A caused a shift of the dithionite (DTN) reduced Fe2+ Soret peak from 430 nm to ~420 nm (FIG. 19, Part B). This shift is neither associated with oxidized or reduced iron. Examination of the literature, revealed that NO and carbon monoxide (CO) causes a shift of the Soret peak to a similar position at 420 nm25. Indeed, a similar shift was observed when DosS was treated with CO (FIG. 19, Part C). Next, it was examined whether amino acid substitutions in the heme exposing channel of DosS resulted in resistance (DosS G117L) and observed that this substitution promoted HC106A resistance in the DosS(G117L) protein (FIG. 19, Part D). Therefore, these data show that HC106A is modulating DosS heme by a mechanism that is distinct from artemisinin, but is accessing the heme via the same G117L dependent channel. Notably, NO/CO induces DosS, however, phenotypically HC106A repressed DosS/T signaling. This suggests that the HC106A/heme interactions are causing a distinct modification of the DosS kinase that potentially locks the kinase in an "off" state. Understanding the molecular basis of this physiology may provide novel insights in the biochemical activation of the DosS/T kinases.

Example 14: Defining Synergistic Interactions Between DosRST Inhibitors

Figure 20:
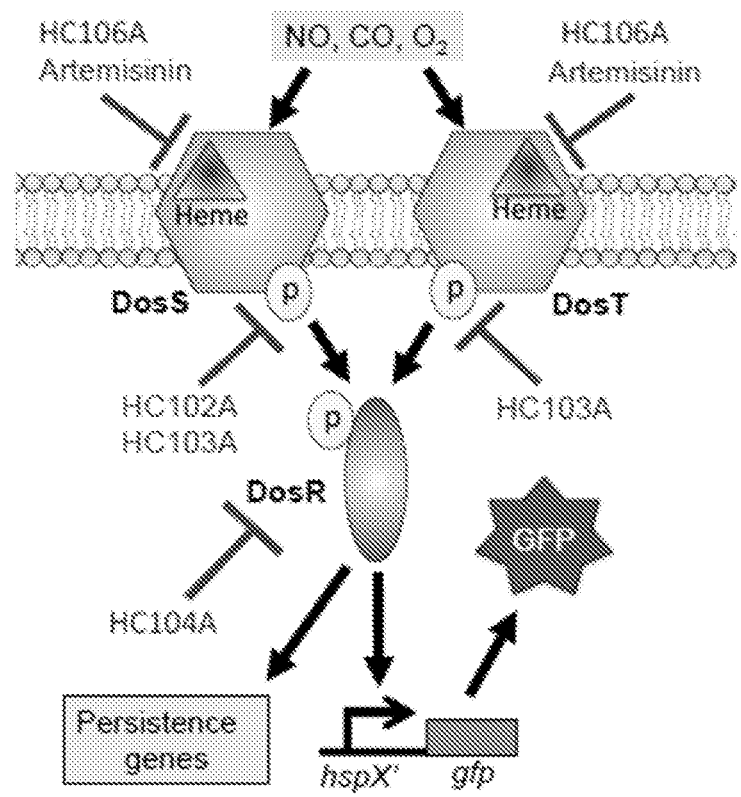
FIG. 20 shows a model for putative different targets of DosRST signaling inhibitors.
Figure 21:
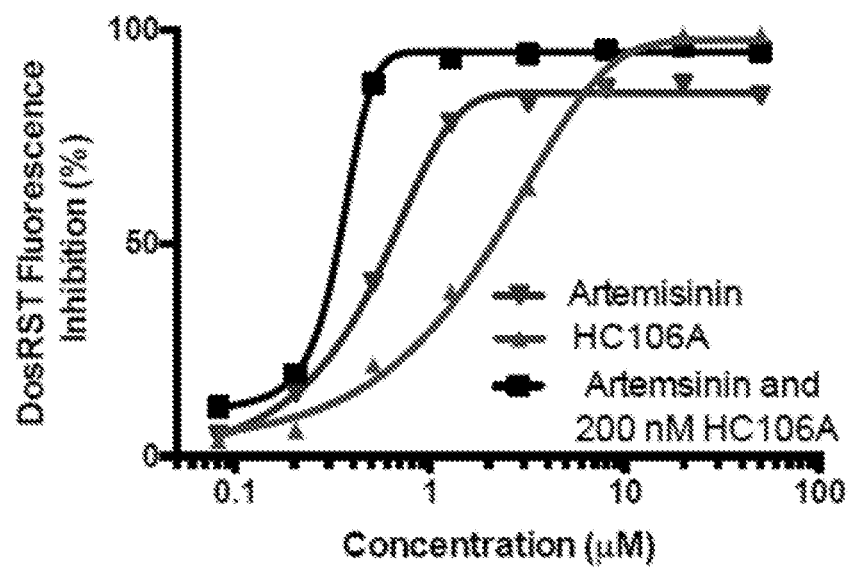
FIG. 21 shows 200 nM HC106A in combination with artemisinin across a dose response curve strongly potentiates inhibition of DosRST signaling in whole cell Mtb.

Currently, inhibitors have been identified with differing potential mechanisms targeted (FIG. 20), including: 1) heme redox modulated by artemisinin and HC106A; 2) Kinase autophosphorylation inhibited by HC102A and HC103A; and 3) DosR DNA-binding inhibited by HC104A. Functional interactions of the compounds were defined similarly to a genetic epistasis study. For example, if HC104A functions to inhibit DosR, it may be observed that HC104A does not improve the function of the other compounds (as it is downstream of DosS and DosT). Even for compounds targeting a similar site (artemisinin and HC106A) it is possible that the interactions may be antagonistic, additive or synergistic depending on the nature of the interaction with DosS/T and the heme. To examine interactions, checkerboard assays analyzing pairwise potentiating interactions between all 6 of the DosRST inhibitors were conducted. In general, additive interactions were observed, except with HC106 and artemisinin, where strong potentiation was observed. For example, addition of 200 nM HC106A (which has no effect on its own) can potentiate 500 nM artemisinin inhibition of DosRST signaling from 40% inhibition to 96% inhibition (FIG. 21). Thus, HC106 and artemisinin exhibit potentiating interactions to inhibit DosRST and combination treatments may be highly potent against whole cell Mtb. Given that HC106 (unoptimized) has activity in whole cells in the low nanomolar level, there is good potential for these compounds to have an excellent selectivity index in vivo.

Example 15: Catalog SAR Studies of HC104 and HC106

A catalog search for HC104 and HC106 was done, where 10 analogs for each series were purchased to develop an early SAR. For HC104A, it was observed that a bromine in the 5-position of is required for activity and that the R2 dimethylamine group is not required (Table 3). For example, HC104B is identical to HC104A except for the removal of the bromine (R1), which results in a complete loss of activity in the whole cell assay. Whereas, replacement of the R2 group with a methyl (HC104G) results in an active compound, although ~10-fold less active than HC104A. Although not highly potent, its ligand efficiency, c Log D and druglikeness are in the range of what would be considered acceptable to good as a starting point for further manipulation. For HC106A (Table 2), catalog SAR work led to a few key understandings around the nature of the series. The simple removal of an ortho chloro on the "A" ring of HC106A leads to enhanced activity ~10-fold, with an EC5050 in the whole cell Mtb assay for DosRST inhibition of ~0.5 µM (HC106F). It was also found that the use of an alternative isomer of the isoxazole had no activity (HC106C).

Figure 22:
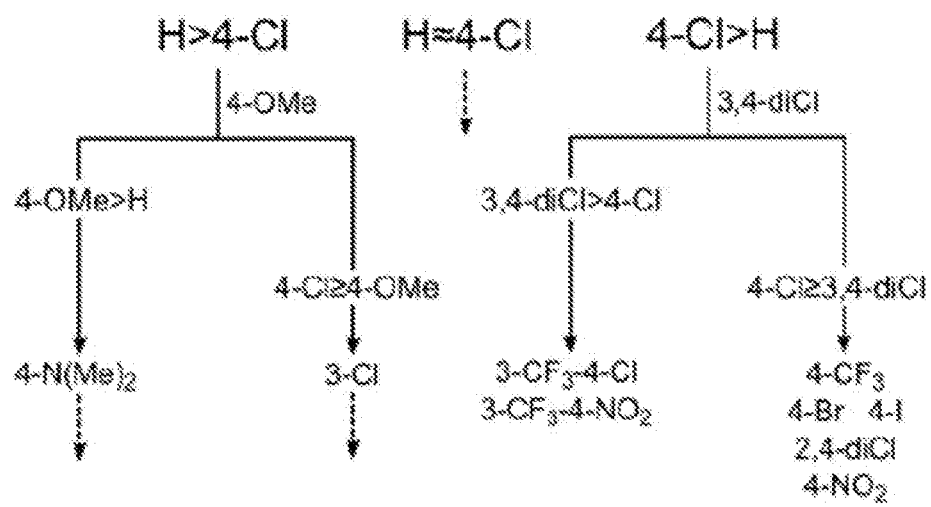
FIG. 22 shows a Topliss Tree is based on Hansch parameters (s and p) for different phenyl substitutions, and the inferred relationship (either positive or negative) between Hansch parameters and potency.

Medicinal chemistry optimizations of HC106. To further understand the SAR of the series, additional analogs were prepared to understand the need of the central urea functionality and whether modifications can be tolerated (Table 4). A pyridyl analog, designed to replace the isoxazole, also demonstrated no activity (the symmetrical 4-chloroaniline derived urea (MSU-41324) has been prepared but yet to be tested). The bis-isoxazole urea (MSU-39444) provides an EC50 of ~2 uM. If the symmetrical 4-chloroaniline is inactive, the isoxazole is essential for binding. Isoxazoles are unique among heterocycles in that they exist in multiple tautomeric forms ((A. J. Bouton, A. R. Katritzky, *Tetrahedron* 1961, 12, 51-55). This is supported by initial NMR studies, and will help define mechanistic insights. The need of one of the —NHs of the urea, capping it with a methyl (MSU-39451), integrating it into a ring for conformational restriction (MSU-39453), and a —CH2- (MSU-39449) was explored. In all cases, reduced activity (0.5-1 log) was observed but not all activity was lost. Thus, HC106A is a potent whole cell inhibitor of the DosRST pathway, with flexibility to be improved via SAR. To further test the SAR, a Topliss Tree evaluation (FIG. 22) of the "A-ring" aniline was performed. To reliably prepare the derivatives, general preparation (Scheme 1) was explored and established. This route is preferred relative to alternative approaches for its cleanliness, yields and ease of purification, usually by trituration. It is also anticipated that it will also allow access into future derivatives. Using HC106F and HC106A as starting points (Table 5), the 3,4-diclorochloro and 3-chloro derivatives (MSU-39452 and MSU-39445, respectively) were prepared. Both the 3- and 4-chloro derivatives demonstrated greater activity than 3,4-dichloro (MSU-39452). Replacing the 4-chlorophenyl ring with pyridyl analogs (MSU-39448 and MSU-39450) lead to diminished activity. Focusing on 4-position derivatives, the fluoro (MSU-39446), bromo (MSU-41464) and methoxy (MSU-39447), as electron p-orbital donating substituents were prepared, the 4-fluoro provides enhanced activity. Testing on bromo (MSU-41464) and methoxy (MSU-39447) will be done. Para-t-butyl and phenyl (MSU-41442), have also been prepared. Electron withdrawing substituents, such as 4-CO2Me (MSU-4165), 4-trifluoromethyl (MSU-41463) and biphenyl (MSU-41443) are awaiting testing.

Example 16: Physical Properties of HC106

The identification of new antibacterial agents and tuberculosis drugs has been associated with the realization that these compounds can occupy a different region of chemical space relative to drugs in most other therapeutic areas. The physical properties of antituberculosis compounds have also been studied and can be grouped into three categories: TB compounds in clinical use; compounds currently in development and compounds in the ChEMBL data base that have been found to have promising anti-TB activity (Table 6). Series HC106 is easily in the range of the characteristics for compounds currently in use, in development and antiTB compounds in the ChEMBL library. Series HC104 needs further exploration to fully assess its suitability. The physicochemical properties of a drug. such as solubility and permeability, impact its oral bioavailability as these factors influence absorption, distribution, metabolism, and excretion. Series HC106 demonstrates reasonably good solubility (Table 3). The melting points of most of the compounds in the series and the corresponding c log P are also supportive. For series HC104, low c log D value of HC104A supports high solubility (as does activity in the whole cell Mtb assay). The ability of an anti-TB drug to reach its target site is greatly hampered by the highly impermeable Mtb cell envelope. Both series (HC104 and HC106) demonstrate excellent whole cell EC50 values suggesting adequate cell wall permeability.

TABLE 6

Comparison of Antibacterial Protein target Chemical Space and Gram-positive Chemical space (includes ribosomal targets); Molecular complexity.

| MW (g/mol) | LogP | TPSA (ang²) | H-bond donors | H-Bond acceptors | #Rotatable bonds | #Aromatic rings |
|---|---|---|---|---|---|---|
| Conventional TB drugs (n = 25)-Average (SD) | | | | | | |
| 361 (220) | −0.5 (3.9) | 91 (107) | 6 (6.4) | 8.3 (5.3) | 5.5 (4.6) | 0.81 (0.87) |
| Current development TB Drugs (n = 13)-Average (SD) | | | | | | |
| 471 (160) | 3 (2.4) | 97 (72) | 2.2 (2) | 7.7 (4.3) | 6.6 (3.8) | 1.93 (1.4) |
| ChEMBL AntiTB (n = 1036)-Average (SD) | | | | | | |
| 410.8 (109.8) | 4.0 (2.3) | 88 (45) | 1.2 (1.4) | 3.1 (1.8) | 5.3 (3.1) | 2.6 (13) |
| Series 104 (Range of current derivatives) | | | | | | |
| 282-361 | cLogP 2.3-3.1 | 37-40 | 0 | 3-4 | 0-4 | 2 |
| Series 106 (Range of current derivatives) | | | | | | |
| 203-280 | cLogP 1.3-3.2 | 63-75 | 2 | 3-4 | 2-3 | 2 |

Example 17: Establishment of the Kramnik Mouse Model

Figure 23:
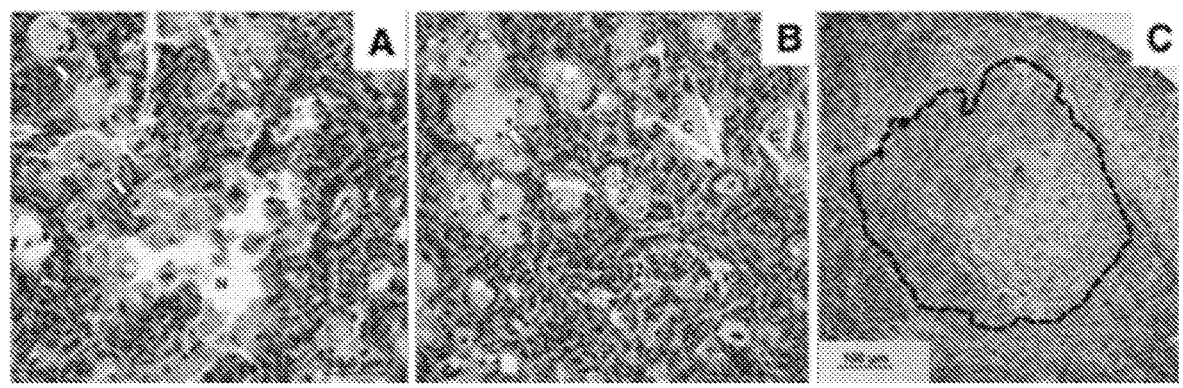
FIG. 23 has three parts, A-C, (A) Mtb infected C3HeB/FeJ Kramnik mice showing ventral necrotic debris and tissue loss [N], amidst foamy MØ, interstitial neutrophilic and multiple multinucleated giant cells (open arrows). (B). Field highlighting the cholesterol cleft formation [C]. (C) Chronic fibrosing pneumonia, with a central region of amorphous necrotic debris, and mixed inflammatory cells outlined by wavy, lamellar, cellular fibrosis (necrosis delineated by line).

C5781/6 and BALB/c murine Mtb infection models do not result in the formation of well-organized caseous necrotic or fibrotic granulomas, a microenvironment in which hypox ia-dependent pathways may play an essential role. In the C3HeB/FeJ "Kramnik" mouse model, infection with Mtb causes formation of granulomas exhibiting hypoxic, caseous necrosis. Using an intranasal inoculum of 250 CFUs of Mtb Erdman strain, it was consistently observed specific hallmarks of Kramnik mouse pathology following 14 weeks of infection, including: fibrotic, necrotizing granulomas, giant-multinucleated cells, foamy M0 and cholesterol clefts (FIG. 23).

REFERENCES

1. Boon, C. and T. Dick, How *Mycobacterium tuberculosis* goes to sleep: the dormancy survival regulator DosR a decade later. Future Microbiol, 2012. 7(4): p. 513-8.
2. Rustad, T. R., et al., Hypoxia: a window into *Mycobacterium tuberculosis* latency. Cell Microbiol, 2009. 11(8): p. 1151-9.
3. Wayne, L. G. and C. D. Sohaskey, Nonreplicating persistence of *Mycobacterium tuberculosis*. Annu Rev Microbiol, 2001. 55: p. 139-63.
4. Mehra, S., et al., The DosR Regulon Modulates Adaptive Immunity and Is Essential for *Mycobacterium tuberculosis* Persistence. Am J Respir Crit Care Med, 2015. 191 (10): p. 1185-96.
5. Hudock, T. A., et al., Hypoxia Sensing and Persistence Genes Are Expressed during the Intragranulomatous Survival of *Mycobacterium tuberculosis*. Am J Respir Cell Mol Biol, 2017. 56(5): p. 637-647.
6. Dasgupta, N., et al., Characterization of a two-component system, devR-devS, of *Mycobacterium tuberculosis*. Tuber Lung Dis, 2000. 80(3): p. 141-59.
7. Park, H. D., et al., Rv3133c/dosR is a transcription factor that mediates the hypoxic response of *Mycobacterium tuberculosis*. Mol Microbiol, 2003. 48(3): p. 833-43.
8. Saini, D. K., et al., DevR-DevS is a bona fide two-component system of *Mycobacterium tuberculosis* that is hypoxia-responsive in the absence of the DNA-binding domain of DevR. Microbiology, 2004. 150(Pt 4): p. 865-75.
9. Voskuil, M. I., et al., Inhibition of respiration by nitric oxide induces a *Mycobacterium tuberculosis* dormancy program. J Exp Med, 2003. 198(5): p. 705-13.
10. Kumar, A., et al., Heme oxygenase-1-derived carbon monoxide induces the *Mycobacterium tuberculosis* dormancy regulon. J Biol Chem, 2008. 283(26): p. 18032-9.
11. Lee, J. M., et al., 02- and NO-sensing mechanism through the DevSR two-component system in *Mycobacterium smegmatis*. J Bacteriol, 2008. 190(20): p. 6795-804.
12. Sousa, E. H., et al., DosT and DevS are oxygen-switched kinases in *Mycobacterium tuberculosis*. Protein Sci, 2007. 16(8): p. 1708-19.
13. Kumar, A., et al., *Mycobacterium tuberculosis* DosS is a redox sensor and DosT is a hypoxia sensor. Proc Natl Acad Sci USA, 2007. 104(28): p. 11568-73.
14. Ioanoviciu, A., et al., DevS, a heme-containing two-component oxygen sensor of *Mycobacterium tuberculosis*. Biochemistry, 2007. 46(14): p. 4250-60.
15. Kim, M. J., et al., Different roles of DosS and DosT in the hypoxic adaptation of Mycobacteria. J Bacteriol, 2010. 192(19): p. 4868-75.
16. Rao, S. P., et al., The protonmotive force is required for maintaining ATP homeostasis and viability of hypoxic, nonreplicating *Mycobacterium tuberculosis*. Proc Natl Acad Sci USA, 2008. 105(33): p. 11945-50.
17. Adams, K. N., et al., Drug tolerance in replicating mycobacteria mediated by a macrophage-induced efflux mechanism. Cell, 2011. 145(1): p. 39-53.
18. Grant, S. S., et al., Eradication of bacterial persisters with antibiotic-generated hydroxyl radicals. Proc Natl Acad Sci USA, 2012. 109(30): p. 12147-52.
19. Leistikow, R. L., et al., The *Mycobacterium tuberculosis* DosR regulon assists in metabolic homeostasis and enables rapid recovery from nonrespiring dormancy. J Bacteriol, 2010. 192(6): p. 1662-70.
20. Converse, P. J., et al., Role of the dosR-dosS two-component regulatory system in *Mycobacterium tuberculosis* virulence in three animal models. Infect Immun, 2009. 77(3): p. 1230-7.
21. Gautam, U.S., S. Mehra, and D. Kaushal, In-Vivo Gene Signatures of *Mycobacterium tuberculosis* in C3HeB/FeJ Mice. PLoS One, 2015. 10(8): p. e0135208.
22. Gautam, U.S., et al., DosS Is required for the complete virulence of *Mycobacterium tuberculosis* in mice with classical granulomatous lesions. Am J Respir Cell Mol Biol, 2015. 52(6): p. 708-16.
23. Baek, S. H., A. H. Li, and C. M. Sassetti, Metabolic regulation of mycobacterial growth and antibiotic sensitivity. PLoS Biol, 2011. 9(5): p. e1001065.
24. Zheng, H., et al., Inhibitors of *Mycobacterium tuberculosis* DosRST signaling and persistence. Nat Chem Biol, 2017. 13(2): p. 218-225.
25. Daniel, J., et al., Induction of a novel class of diacylglycerol acyltransferases and triacylglycerol accumulation in *Mycobacterium tuberculosis* as it goes into a dormancy-like state in culture. J Bacteriol, 2004. 186(15): p. 5017-30.
26. Sirakova, T. D., et al., Identification of a diacylglycerol acyltransferase gene involved in accumulation of triacylglycerol in *Mycobacterium tuberculosis* under stress. Microbiology, 2006. 152(Pt 9): p. 2717-25.
27. Hung, D. T., et al., Small-molecule inhibitor of *Vibrio cholerae* virulence and intestinal colonization. Science, 2005. 310(5748): p. 670-4.
28. Chou, T. and N. Martin, CompuSyn for Drug Combinations: PC Software and User's Guide: A Computer Program for Quantitation of Synergism and Antagonism in Drug Combinations, and the Determination of IC50 and ED50 and LD50 Values, in ComboSyn, Paramus, N J. 2005.
29. Chou, T. C. and P. Talalay, Quantitative analysis of dose-effect relationships: the combined effects of multiple drugs or enzyme inhibitors. Adv Enzyme Regul, 1984. 22: p. 27-55.
30. Boulton, A. J. and A. R. Katritzky, The tautomerism of heteroaromatic compounds with five-membered rings—I: 5-hycroxyisoxazoles-isoxazol-5-ones. Tetrahedron, 1961. 12(1): p. 41-50.
31. Lee, H. N., et al., Protein-protein interactions between histidine kinases and response regulators of *Mycobacterium tuberculosis* H37Rv. J Microbiol. 2012. 50(2): p. 270-7.
32. Honaker, R. W., et al., Unique roles of DosT and DosS in DosR regulon induction and *Mycobacterium tuberculosis* dormancy. Infect Immun, 2009. 77(8): p. 3258-63.
33. Baker, J. J., B. K. Johnson, and R. B. Abramovitch, Slow growth of *Mycobacterium tuberculosis* at acidic pH is regulated by phoPR and host-associated carbon sources. Mol Microbiol, 2014. 94(1): p. 56-69.

34. Johnson, B. K., et al., SPARTA: Simple Program for Automated reference-based bacterial RNA-seq Transcriptome Analysis. BMC Bioinformatics, 2016. 17: p. 66.
35. Johnson, B. K. and R. B. Abramovitch, Macrophage infection models for *Mycobacterium tuberculosis*. Methods Mol Biol, 2015. 1285: p. 329-41.
36. Schneider, C. A., W. S. Rasband, and K. W. Eliceiri, NIH Image to ImageJ: 25 years of image analysis. Nat Methods, 2012. 9(7): p. 671-5.
37. Mak, P. A., et al., A high-throughput screen to identify inhibitors of ATP homeostasis in non-replicating *Mycobacterium tuberculosis*. ACS Chem Biol, 2012. 7(7): p. 1190-7.
38. Vashist, A., et al., The alpha10 helix of DevR, the *Mycobacterium tuberculosis* dormancy response regulator, regulates its DNA binding and activity. Febs j, 2016. 283(7): p. 1286-99.
39. Chou, T. C., Drug combination studies and their synergy quantification using the Chou-Talalay method. Cancer Res, 2010. 70(2): p. 440-6.

INCORPORATION BY REFERENCE

The contents of all references, patent applications, patents, and published patent applications, as well as the Figures, cited throughout this application are hereby incorporated by reference.

EQUIVALENTS

While the present disclosure has been described with reference to the specific embodiments thereof, it should be understood by those skilled in the art that various changes may be made and equivalents may be substituted without departing from the true spirit and scope of the disclosure. In addition, many modifications may be made to adapt a particular situation, material, composition of matter, process, process step or steps, to the objective, spirit and scope of the present disclosure. All such modifications are intended to be within the scope of the disclosure.

What is claimed is:

1. A bacterial growth inhibitor having a structure of Formula I or a pharmaceutically acceptable salt thereof:

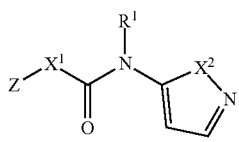

wherein
$X^1$ is $NR^2$;
$X^2$ is O;
$R^1$ and $R^2$ are each independently H; and
Z is an aryl substituted with cycloalkyl, alkoxy, aryl, heteroaryl, acyl, 3-halo, 4-halo, 3,4-halo, sulfone, sulfonate, hydroxy, amide, and amino.

2. The compound of claim 1, wherein Z is

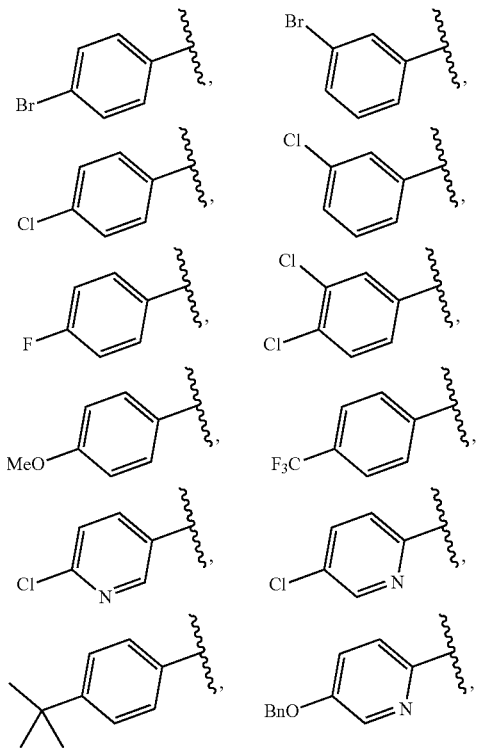

-continued

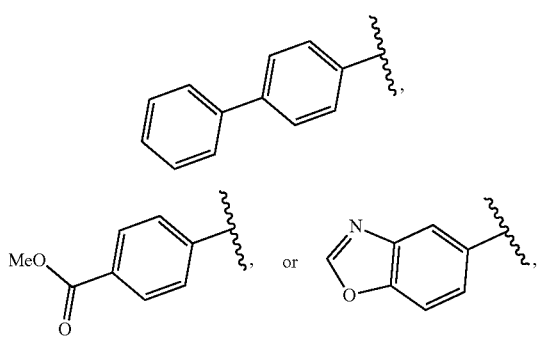

3. A compound selected from

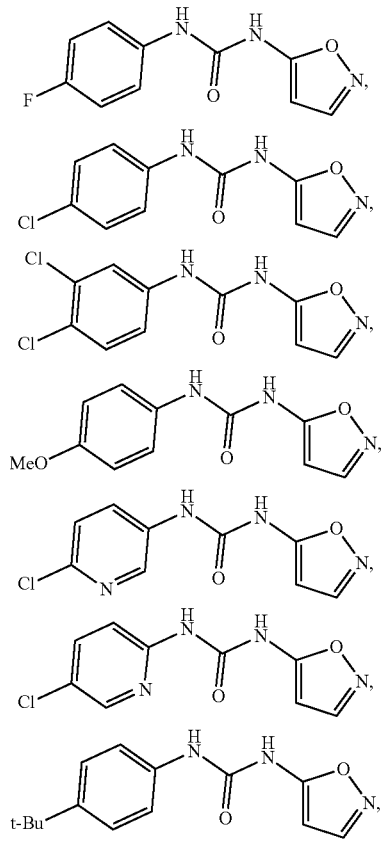

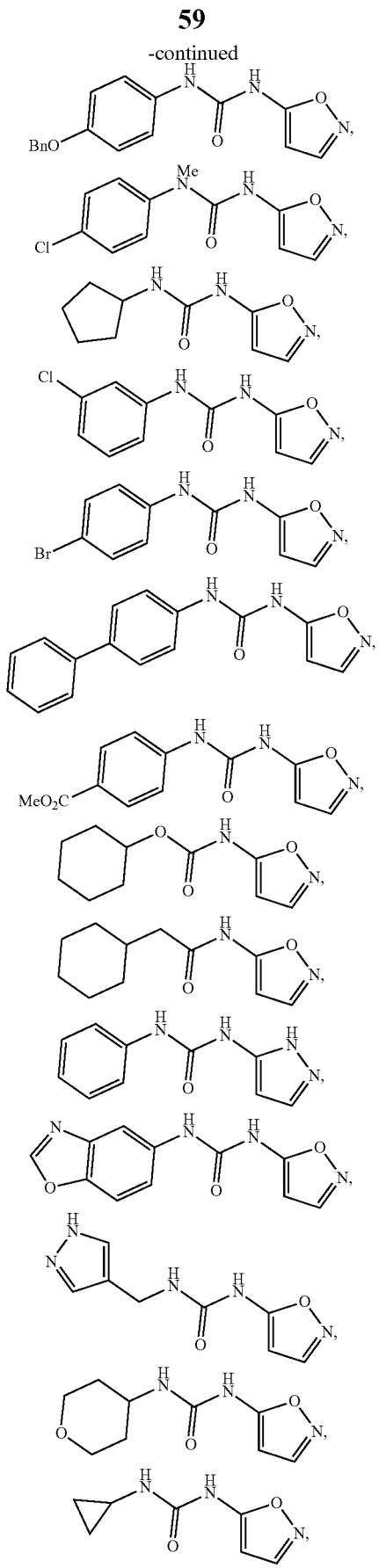

4. A method for inhibiting growth of one or more bacterial cells, the method comprising contacting the one or more bacterial cells with an effective amount of a compound of claim 1 to thereby inhibit the growth of the one or more bacterial cells.

5. A method for treating a subject who is infected with bacterial cells, the method comprising administering to the subject an effective amount of a compound of claim 1 to thereby treat the infection.

6. The method of claim 4, wherein the bacteria utilize environmental heme-based sensor proteins to sense environmental signals.

7. The method of claim 4, wherein the DorRST two component regulatory system is conserved in the bacterial cells, and wherein the compound inhibits DosRST signaling, inhibits of DosST sensor kinase activity, modulates DosST heme, or inhibits DosR DNA binding.

8. The method of claim 4, wherein the bacteria or bacterial cells are *Mycobacterium*, and *Mycobacterium* are tolerant to several anti-mycobacterial drugs.

9. The method of claim 4, wherein the method further comprises administering artemisinin.

10. The method of claim 5, wherein the infection is tuberculosis or a non-tuberculosis *Mycobacterium*.

11. The method of claim 9 wherein, administering the compound and artemisinin provide a synergistic effect in reducing the infection.

* * * * *